(12) United States Patent
Tanoury et al.

(10) Patent No.: US 8,946,425 B2
(45) Date of Patent: Feb. 3, 2015

(54) PROCESSES AND INTERMEDIATES FOR PRODUCING AZAINDOLES

(71) Applicant: Vertex Pharmaceuticals Incorporated, Boston, MA (US)

(72) Inventors: Gerald J. Tanoury, Marlborough, MA (US); Young Chun Jung, Lexington, MA (US); Derek Magdziak, Medford, MA (US); Adam Looker, Newton, MA (US); Billie J. Kline, Kingston, MA (US); Václav Jurčík, Kingston, MA (US); Beatriz Dominguez Olmo, Bury St Edmunds (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/314,158

(22) Filed: Jun. 25, 2014

(65) Prior Publication Data

US 2014/0309421 A1    Oct. 16, 2014

Related U.S. Application Data

(62) Division of application No. 13/940,421, filed on Jul. 12, 2013, now Pat. No. 8,796,453, which is a division of application No. 13/541,504, filed on Jul. 3, 2012, now Pat. No. 8,513,414.

(60) Provisional application No. 61/636,296, filed on Apr. 20, 2012, provisional application No. 61/504,351, filed on Jul. 5, 2011.

(51) Int. Cl.
    C07D 471/04    (2006.01)
    C07F 5/02      (2006.01)
    C07D 239/42    (2006.01)

(52) U.S. Cl.
    CPC .............. *C07F 5/025* (2013.01); *C07D 471/04* (2013.01); *C07D 239/42* (2013.01)
    USPC .......................................................... 546/113

(58) Field of Classification Search
    USPC .......................................................... 546/113
    See application file for complete search history.

(56) References Cited

U.S. PATENT DOCUMENTS

| 7,507,826 B2 | 3/2009 | Salituro et al. |
| 7,767,816 B2 | 8/2010 | Farmer et al. |
| 8,129,387 B2 | 3/2012 | Charrier et al. |
| 8,450,489 B2 | 5/2013 | Farmer et al. |
| 8,513,414 B2 | 8/2013 | Tanoury et al. |
| 2002/0052386 A1 | 5/2002 | Armistead et al. |
| 2002/0065270 A1 | 5/2002 | Moriarty et al. |
| 2005/0208582 A1 | 9/2005 | Ohi et al. |
| 2012/0165307 A1 | 6/2012 | Farmer et al. |
| 2012/0258958 A1 | 10/2012 | Salituro et al. |
| 2013/0303764 A1 | 11/2013 | Tanoury et al. |

FOREIGN PATENT DOCUMENTS

| WO | 99/21859 | 5/1999 |
| WO | 03/000688 | 1/2003 |
| WO | 03/091246 | 11/2003 |
| WO | 2005/095400 | 10/2005 |
| WO | 2006/127587 | 11/2006 |
| WO | 2007/084557 | 7/2007 |
| WO | 2013/006634 | 1/2013 |
| WO | 2013/070606 | 5/2013 |

OTHER PUBLICATIONS

International Search Report issued for PCT Application No. PCT/US2005/010846 Dated Aug. 19, 2005.
International Search Report issued for PCT Application No. PCT/US2007/001225 Dated Jul. 20, 2007.
International Search Report issued for PCT Application No. PCT/US2012/045431 dated Feb. 5, 2013.

*Primary Examiner* — Kristin Vajda
(74) *Attorney, Agent, or Firm* — Honigman Miller Schwartz and Cohn LLP; Andrew N. Weber; Jonathan P. O'Brien

(57) ABSTRACT

The present invention relates to processes and intermediates for the preparation of compounds useful as inhibitors of Janus kinases (JAK).

22 Claims, 4 Drawing Sheets

PROCESSES AND INTERMEDIATES FOR PRODUCING AZAINDOLES

CROSS REFERENCE TO RELATED APPLICATION

The present U.S. patent application is a divisional of U.S. application Ser. No. 13/940,421, filed on Jul. 12, 2013, which is a divisional of U.S. application Ser. No. 13/541,504, filed on Jul. 3, 2012, which claims the benefit of U.S. application Ser. No. 61/504,351, filed on Jul. 5, 2011, and U.S. application Ser. No. 61/636,296, filed on Apr. 20, 2012. Each of these applications is hereby incorporated by reference in its entirety.

TECHNICAL FIELD OF THE INVENTION

The present invention relates to processes and intermediates for the preparation of compounds useful as inhibitors of Janus kinases (JAK).

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Compounds described as kinase inhibitors, particularly the JAK family kinases, are disclosed in WO 2005/095400 and WO 2007/084557 the entire contents of each of which are incorporated herein by reference. Also disclosed in these publications are processes and intermediates for the preparation of these compounds. There remains however, a need for economical processes for the preparation of these compounds.

SUMMARY OF THE INVENTION

The present invention relates to processes and intermediates that are useful for generating JAK inhibitors.

The present invention provides a process for preparing a compound of Formula I:

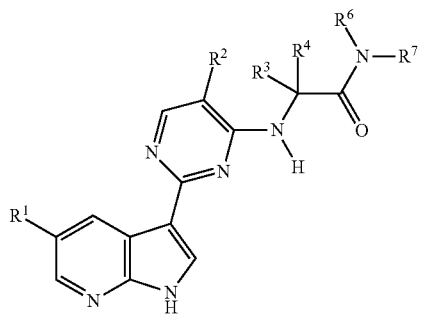

I or a pharmaceutically acceptable salt thereof, wherein $R^1$ is —H, —Cl or —F; $R^2$ is —H or —F; $R^3$ is —$C_{1-4}$ aliphatic optionally substituted with 1-5 occurrences of $R^5$; $R^4$ is —$C_{1-2}$ alkyl optionally substituted with 1-3 occurrences of $R^5$; or $R^3$ and $R^4$ are taken together to form a 3-7 membered carbocyclic or heterocyclic saturated ring optionally substituted with 1-5 occurrences of $R^5$; each $R^5$ is independently selected from halogen, —$OCH_3$, —OH, —$NO_2$, —$NH_2$, —SH, —$SCH_3$, —$NHCH_3$, —CN, or unsubstituted —$C_{1-2}$ aliphatic, or two $R^5$ groups, together with the carbon to which they are attached, form a cyclopropyl ring; $R^6$ is —H or unsubstituted —$C_{1-2}$ alkyl; and $R^7$ is a —$CH_2CR_3$ or —$(CH_2)_2CR_3$ wherein each R is independently —H or —F; comprising the step of: i) reacting a compound of Formula 1 with a hydrochloride salt of a compound Formula 2

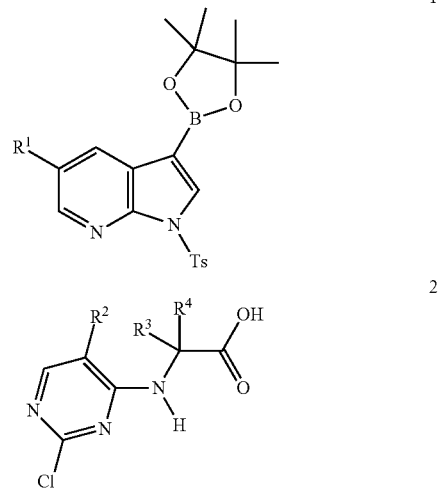

in the presence of water, an organic solvent, a base, and a transition metal catalyst to generate a compound of Formula I.

In some embodiments, the organic solvent of step i) is an aprotic solvent. For example, the aprotic solvent of step i) is acetonitrile, toluene, N,N-dimethylformamide, N,N-dimethylacetamide, acetone, methyl tert-butyl ether, or any combination thereof.

In some embodiments, the organic solvent of step i) is a protic solvent. For example, the protic solvent of step i) is an alcohol selected from methanol, propanol, isopropanol, butanol, tert-butanol, or any combination thereof.

In some embodiments, the base of step i) is an inorganic base. For example, the inorganic base of step i) comprises tripotassium phosphate, dipotassium hydrogen phosphate, dipotassium carbonate, disodium carbonate, trisodium phosphate, disodium hydrogen phosphate, or any combination thereof. In other examples, the inorganic base of step i) comprises an alkali metal hydroxide such as NaOH, KOH, or any combination thereof.

In some embodiments, the transition metal catalyst of step i) is a palladium catalyst. For example, the palladium catalyst of step i) comprises palladium(II)acetate, tetrakis(triphenylphosphine)palladium(0), tris(dibenzylideneacetone)dipalladium(0), or any combination thereof. In other implementations, the palladium catalyst is generated in situ, and the reaction of step i) occurs in the presence of a phosphine ligand (e.g., triphenylphosphine). And in other examples, the palladium catalyst of step i) comprises

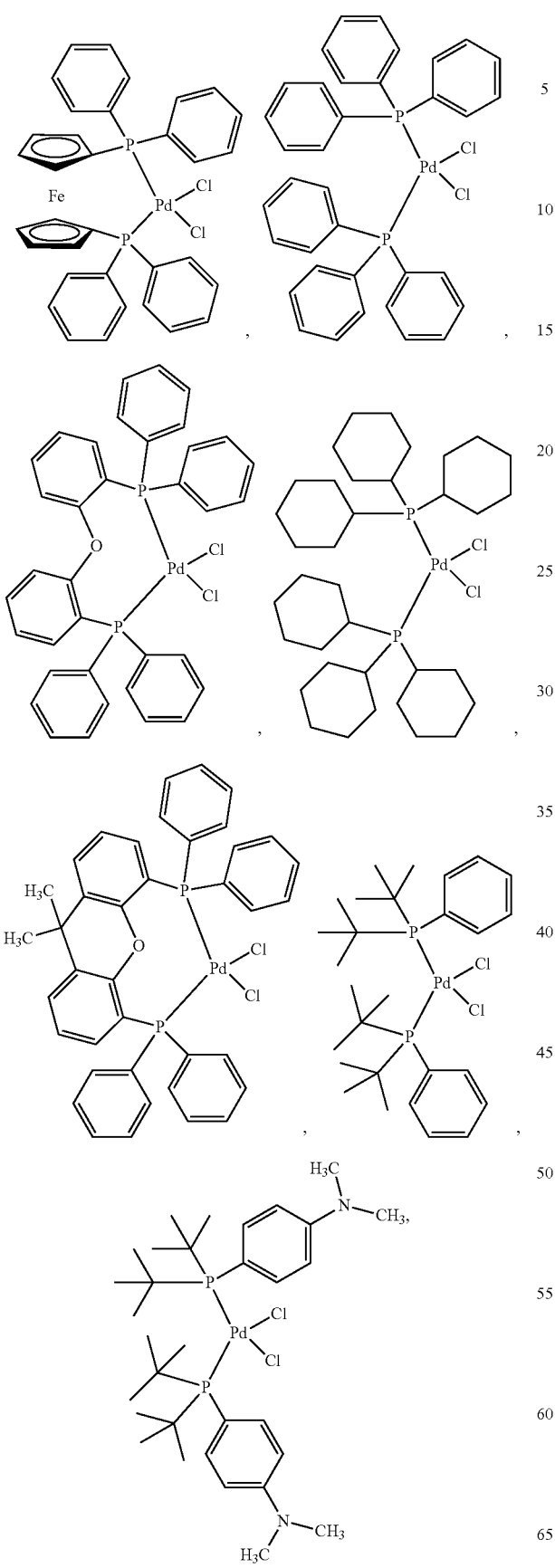

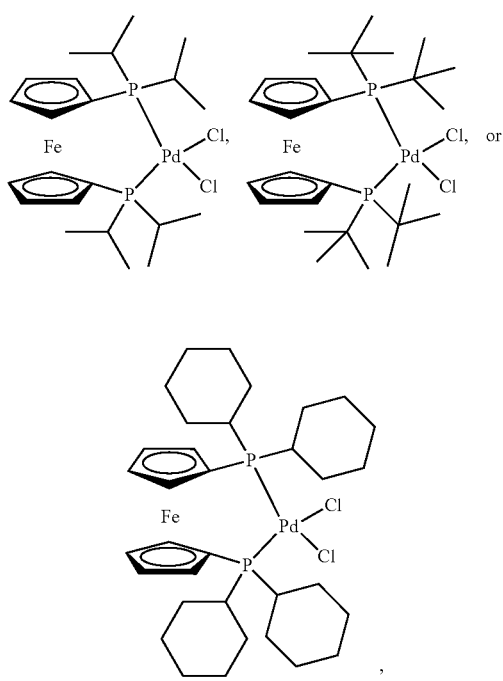

or any combination thereof.

In some embodiments, the reaction of step i) is performed at a temperature between about 50° C. and about 110° C. (e.g., between about 60° C. and about 95° C. or between about 70° C. and about 80° C.)

In some embodiments, the reaction of step i) is performed with agitation. For example, the reaction is performed in a vessel containing a stir bar or mixer that agitates the reaction mixture.

In some embodiments, the reaction of step i) occurs in about 17 hours.

In some embodiments, the reaction of step i) is about 86% complete in about 5 hours.

In some embodiments, the reaction of step i) is about 99% complete in about 17 hours.

Other embodiments further comprise the steps of: ii) deprotecting a compound of Formula 3 to generate a compound of Formula 4:

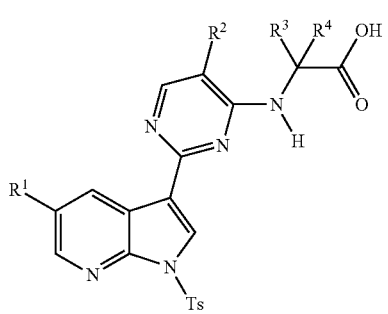

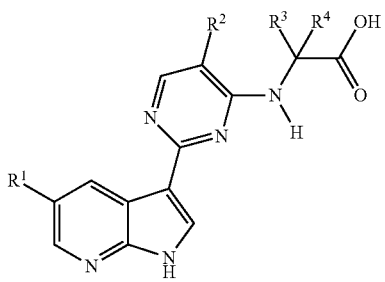

and; iii) reacting the compound of Formula 4 with HNR⁶R⁷ in the presence of a coupling agent and an organic solvent to generate the compound of Formula I.

In some embodiments, step ii) comprises deprotecting the compound of Formula 3 in the presence of a base. For example, the base of step ii) comprises an inorganic base. In some examples, the inorganic base of step ii) is an alkali metal hydroxide such as NaOH, KOH, or any combination thereof.

In some embodiments, HNR⁶R⁷ is 2,2,2-trifluoroethylamine.

In some embodiments, the reaction of step iii) is performed in the presence of an organic base. In some examples, the organic base of step iii) comprises a tertiary amine. For example, the tertiary amine of step iii) comprises N,N-diisopropylethylamine, triethylamine, or any combination thereof.

In some embodiments, the coupling agent of step iii) comprises propylphosphonic anhydride.

In some embodiments, the organic solvent of step iii) comprises a halogenated hydrocarbon, an alkyl substituted tetrahydrofuran, or any combination thereof. For example, the organic solvent of step iii) comprises an alkyl substituted tetrahydrofuran such as 2-methyltetrahydrofuran. In other examples, the organic solvent of step iii) comprises a halogenated hydrocarbon such as dichloromethane or dichloroethane.

Some embodiments further comprise the steps of: iva) reacting a compound of Formula 5 with bromine in an organic solvent to generate a compound of Formula 6:

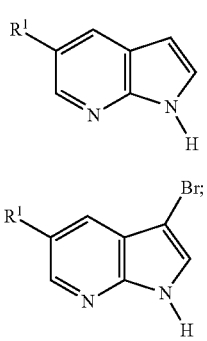

va) reacting the compound of Formula 6 with p-toluenesulfonyl chloride to generate a compound of Formula 7:

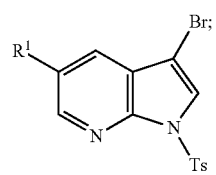

vi) reacting the compound of Formula 7 with triisopropyl borate, in the presence of an organic solvent and a strong lithium base to generate a compound of Formula 8:

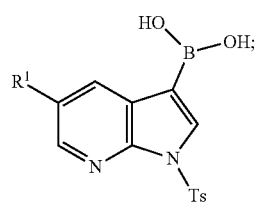

and vii) esterifying the compound of Formula 8 with pinacolate alcohol in an organic solvent to generate a compound of Formula 1.

Some embodiments further comprise the steps of: ivb) reacting a compound of Formula 5 with p-toluenesulfonyl chloride to generate a compound of Formula 9:

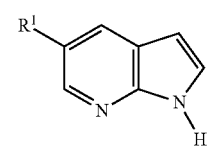

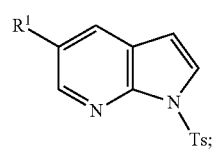

vb) reacting the compound of Formula 9 with N-bromosuccinimide to generate a compound of Formula 7:

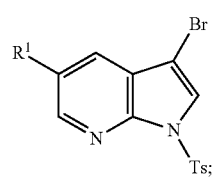

vi) reacting the compound of Formula 7 with triisopropyl borate, in the presence of an organic solvent and a strong lithium base to generate a compound of Formula 8:

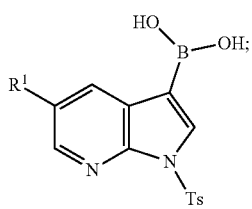

8 and vii) esterifying the compound of Formula 8 with pinacolate alcohol in an organic solvent to generate a compound of Formula 1.

Some embodiments further comprise the step of: viiia) reacting a compound of Formula 10, wherein $R^8$ is a —$C_{1-4}$ alkyl, with a compound of Formula 11:

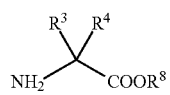

10

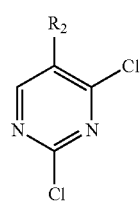

11 in the presence of an organic base and an organic solvent to generate a mixture comprising a compound of Formula 12 and a compound of Formula 13:

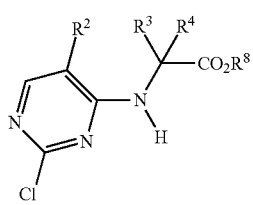

12

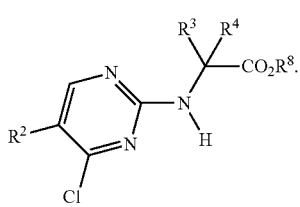

13

Some embodiments further comprise the steps of: ixa) deprotecting the compound of Formula 12 and the compound of Formula 13 in the presence of an inorganic acid to generate a mixture comprising a compound of Formula 2 and a compound of Formula 14:

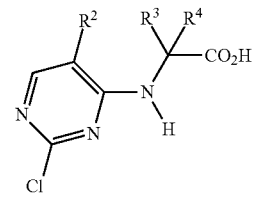

2

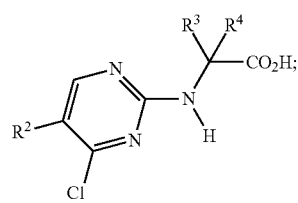

14 xa) reacting the mixture comprising the compound of Formula 2 and the compound of Formula 14 with HCl in the presence of an organic solvent to generate the hydrochloride salts of the compound of Formula 2 and the compound of Formula 14; and xia) recrystallizing the mixture of the hydrochloride salts of the compound of Formula 2 and the compound of Formula 14 to generate the hydrochloride salt of the compound of Formula 2.

Some alternative embodiments further comprising the steps of: viiib) reacting a compound of Formula 11 with an acid salt of a compound of Formula 15 in the presence of a solvent and a base to generate the compound Formula 2:

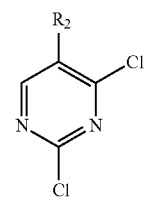

11

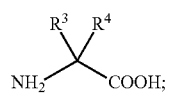

15 and ixb) reacting the compound of Formula 2 with HCl to generate the hydrochloride salt of the compound of Formula 2.

In some embodiments, the base of step viiib) is an inorganic base selected from tripotassium phosphate, dipotassium hydrogen phosphate, dipotassium carbonate, disodium carbonate, trisodium phosphate, disodium hydrogen phosphate, or any combination thereof.

In some embodiments, the solvent of step viiib) comprises water.

In some embodiments, the solvent of step viiib) further comprises an alcohol selected from methanol, ethanol, propanol, iso-propanol, butanol, tert-butanol, or any combination thereof.

In some embodiments, the reaction of step viiib) is performed at a temperature of from about 70° C. to about 120° C. (e.g., 80° C. to about 100° C.).

The present invention also provides a process for preparing a compound of Formula 4:

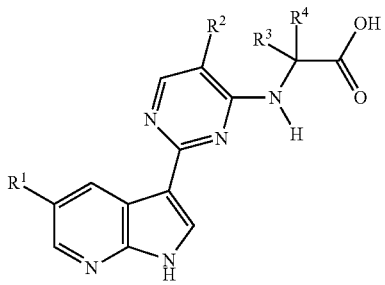

wherein $R^1$ is —H, —Cl or —F; $R^2$ is —H or —F; $R^3$ is —$C_{1-4}$ aliphatic optionally substituted with 1-5 occurrences of $R^5$; $R^4$ is —$C_{1-2}$ alkyl optionally substituted with 1-3 occurrences of $R^5$; or $R^3$ and $R^4$ are taken together to form a 3-7 membered carbocyclic or heterocyclic saturated ring optionally substituted with 1-5 occurrences of $R^5$; each $R^5$ is independently selected from halogen, —$OCH_3$, —OH, —$NO_2$, —$NH_2$, —SH, —$SCH_3$, —$NHCH_3$, —CN, or unsubstituted —$C_{1-2}$ aliphatic, or two $R^5$ groups, together with the carbon to which they are attached, form a cyclopropyl ring; comprising the step of: ia) reacting a compound of Formula 1 with a hydrochloride salt of a compound Formula 2,

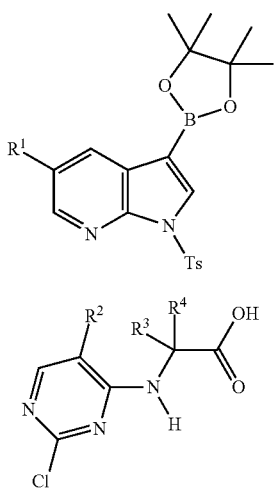

in the presence of water, an organic solvent, a base, and a palladium (Pd) catalyst selected from

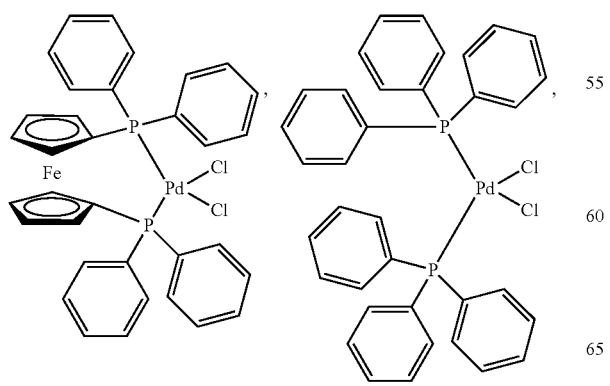

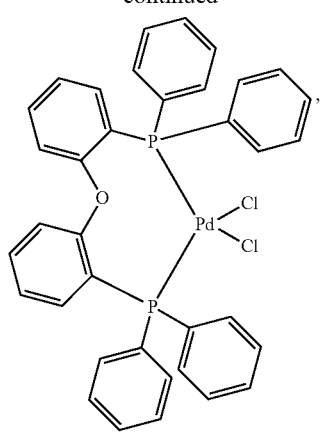

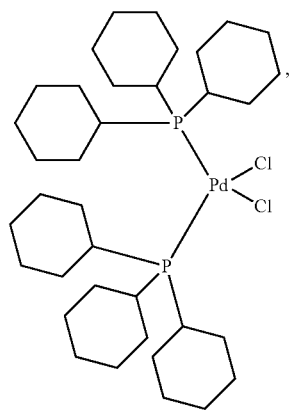

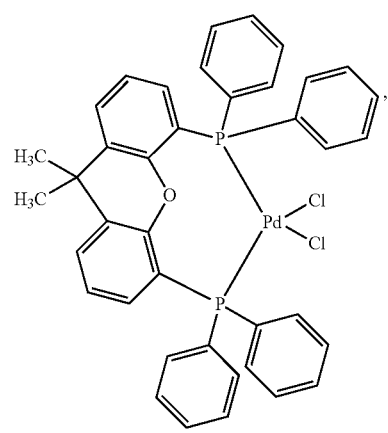

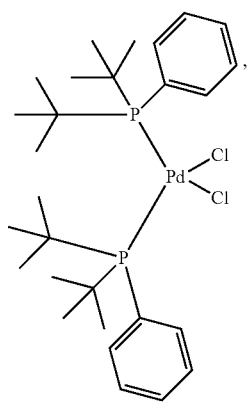

-continued

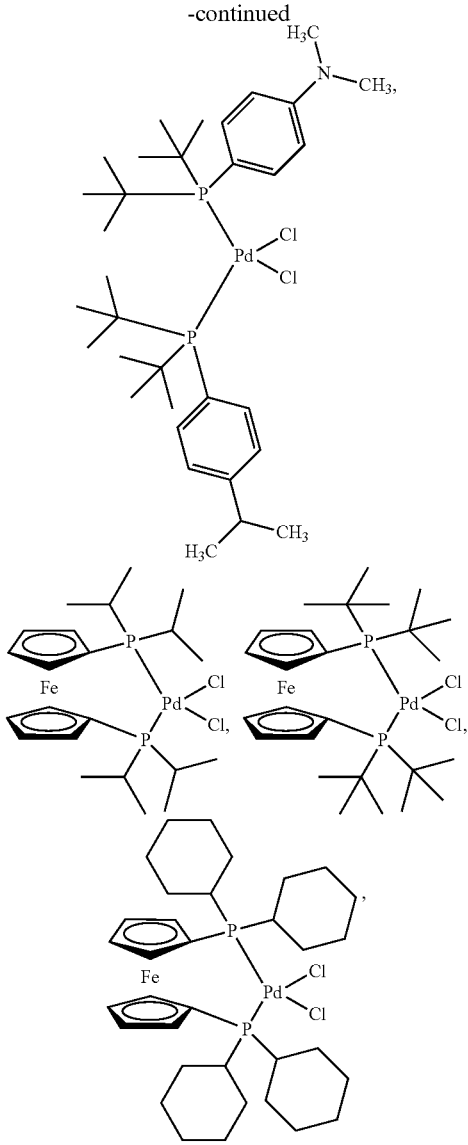

or any combination thereof, to generate a compound of Formula 3, and

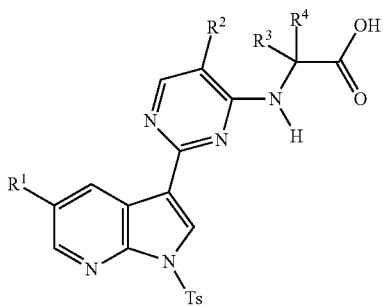

ii) deprotecting the compound of Formula 3 to generate the compound of Formula 4.

In some embodiments, the organic solvent of step ia) is an alcohol. For example, the alcohol of step ia) is selected from methanol, ethanol, propanol, isopropanol, butanol, tert-butanol, or any combination thereof.

In some embodiments, the base of step ia) is an inorganic base. For example, the inorganic base of step ia) is an alkali metal hydroxide such as NaOH, KOH, or any combination thereof.

In some embodiments, the reaction of step ia) is performed at a temperature between about 50° C. and about 110° C. (e.g., between about 60° C. and about 95° C. or between about 70° C. and about 80° C.).

In some embodiments, step ia) is performed with agitation. For example, the reaction is performed in a vessel containing a stir bar that agitates the reaction mixture.

In some embodiments, the reaction of step ia) occurs in about 17 hours.

In some embodiments, the reaction of step ia) is about 86% complete in about 5 hours.

In some embodiments, the reaction of step ia) is about 99% complete in about 17 hours.

In some embodiments, the deprotection of step ii) is performed in the presence of a base. In some examples, the base of step ii) is an inorganic base. In other examples, the inorganic base of step ii) is an alkali metal hydroxide such as KOH, NaOH, or any combination thereof.

Some embodiments further comprise the steps: viiib) reacting a compound of Formula 11 with an acid salt of a compound of Formula 15 in the presence of a solvent and a base to generate the compound Formula 2

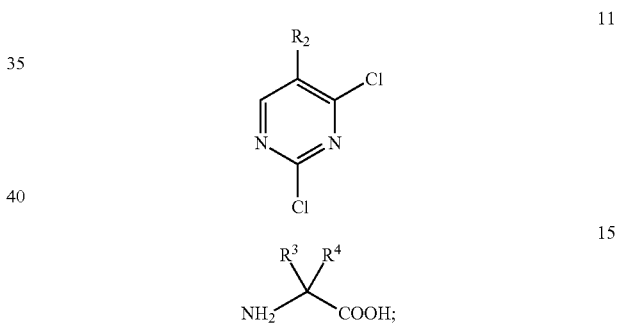

and ixb) reacting the compound of Formula 2 with HCl to generate the hydrochloride salt of the compound of Formula 2.

In some embodiments, the base of step viiib) is an inorganic base selected from tripotassium phosphate, dipotassium hydrogen phosphate, dipotassium carbonate, disodium carbonate, trisodium phosphate, disodium hydrogen phosphate, or any combination thereof.

In some embodiments, the solvent of step viiib) comprises water.

In some embodiments, the solvent of step viiib) further comprises an alcohol selected from methanol, ethanol, propanol, iso-propanol, butanol, tert-butanol, or any combination thereof.

In some embodiments, the reaction of step viiib) is performed at a temperature of from about 70° C. to about 120° C. (e.g., from about 80° C. to about 100° C.).

The present invention also provides a process for preparing a compound of Formula 1:

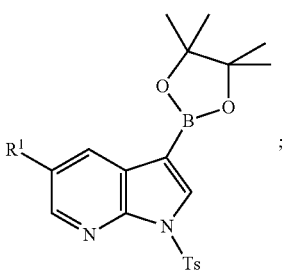

or a pharmaceutically acceptable salt thereof, wherein $R^1$ is —H, —Cl, or —F; comprising the steps of: iva) reacting a compound of Formula 5 with bromine in an organic solvent to generate a compound of Formula 6:

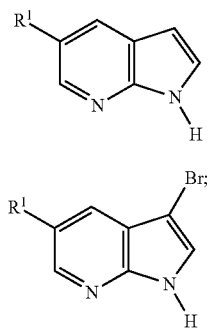

va) reacting the compound of Formula 6 with p-toluenesulfonyl chloride to generate a compound of Formula 7:

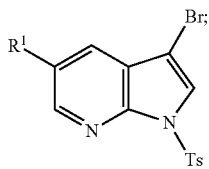

vi) reacting the compound of Formula 7 with triisopropyl borate, in the presence of an organic solvent and a strong lithium base to generate a compound of Formula 8:

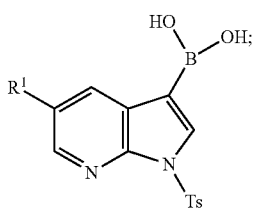

and vii) esterifying the compound of Formula 8 with pinacolate alcohol in an organic solvent to generate a compound of Formula 1.

In some embodiments, the organic solvent of step iva) is an aprotic solvent. For example, the aprotic solvent of step iva) is dimethylformamide.

In some embodiments, the reaction of step iva) is performed at a temperature of about −5° C. to about 30° C. (e.g., about 0° C. to about 10° C.).

In some embodiments, the reaction of step va) is performed in the presence of sodium hydride.

In some embodiments, the reaction of step va) is performed at a temperature of about 0° C. to about 30° C. (e.g., about 5° C. to about 25° C. or about 10° C. to about 20° C.).

In some embodiments, the strong lithium base of step vi) is n-butyl lithium.

In some embodiments, the reaction of step vi) is performed at a temperature of about −100° C. to about −70° C. (e.g., about −90° C. to about −80° C.).

In some embodiments, the organic solvent of step vii) is a halogenated hydrocarbon. For example, the halogenated hydrocarbon of step vii) is dichloromethane or dichloroethane.

In some embodiments, the esterification reaction in step vii) is performed at a temperature of about 0° C. to about 60° C. (e.g., about 10° C. to about 40° C. or about 20° C. to about 30° C.).

In some embodiments, the compound of Formula 5 is selected from

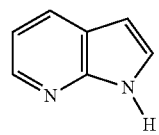

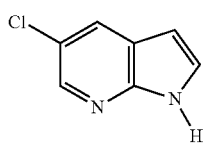

1H-pyrrolo[2,3-b]pyridine (5a) or 5-chloro-1H-pyrrolo[2,3-b]pyridine (5b).

In some embodiments, the compound of Formula 6 is selected from

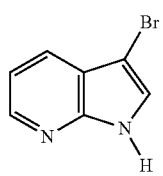

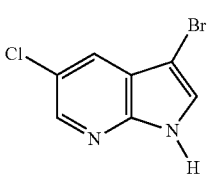

3-bromo-1H-pyrrolo[2,3-b]pyridine (6a) or 3-bromo-5-chloro-1H-pyrrolo[2,3-b]pyridine (6b); the compound of Formula 7 is selected from

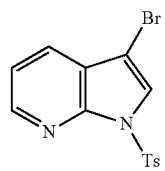

7a

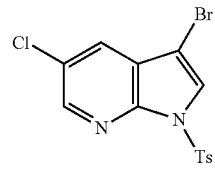

7b 3-bromo-1-tosyl-1H-pyrrolo[2,3-b]pyridine (7a) or 3-bromo-5-chloro-1-tosyl-1H-pyrrolo[2,3-b]pyridine (7b); the compound of Formula 8 is selected from

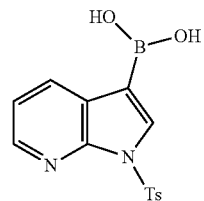

8a

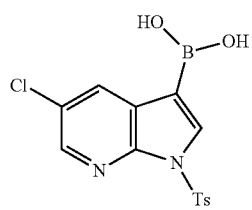

8b 1-tosyl-1H-pyrrolo[2,3-b]pyridin-3-ylboronic acid (8a) or 5-chloro-1-tosyl-1H-pyrrolo[2,3-b]pyridin-3-ylboronic acid (8b); and the compound of Formula 1 is selected from

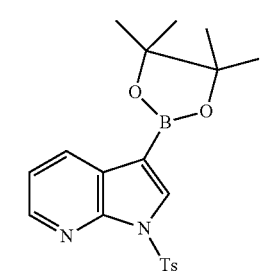

1a

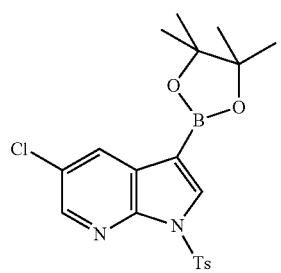

1b 3-(4,4,5,5-tetramethyl-1,3,2-dioxaborolan-2-yl)-1-tosyl-1H-pyrrolo[2,3-b]pyridine (1a) or 5-chloro-3-(4,4,5,5-tetramethyl-1,3,2-dioxaborolan-2-yl)-1-tosyl-1H-pyrrolo[2,3-b]pyridine (1b).

The present invention also provides a process for preparing a compound of Formula 1:

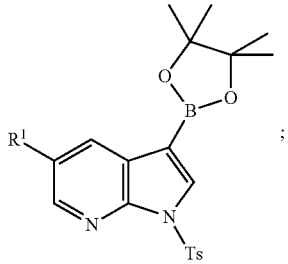

1 or a pharmaceutically acceptable salt thereof, wherein $R^1$ is —H, —Cl, or —F; comprising the steps of: ivb) reacting a compound of Formula 5 with p-toluenesulfonyl chloride to generate a compound of Formula 9:

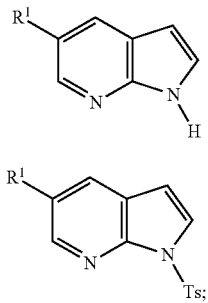

5

9 vb) reacting the compound of Formula 9 with N-bromosuccinimide to generate a compound of Formula 7:

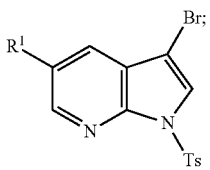

7 vi) reacting a compound of Formula 7 with triisopropyl borate, in the presence of an organic solvent and a strong lithium base to generate a compound of Formula 8:

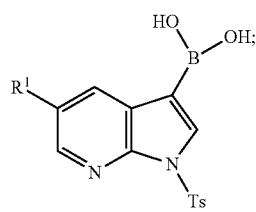

8 and vii) esterifying a compound of Formula 8 with pinacolate alcohol in an organic solvent to generate a compound of Formula 1.

In some embodiments, the reaction of step ivb) is performed in the presence of sodium hydride.

In some embodiments, the strong lithium base of step vi) is n-butyl lithium.

In some embodiments, the reaction of step vi) is performed at a temperature of about −100° C. to about −70° C. (e.g., about −90° C. to about −80° C.).

In some embodiments, the organic solvent of step vii) is a halogenated hydrocarbon such as any of those halogenated hydrocarbons described herein.

In some embodiments, the esterification reaction of step vii) is performed at a temperature of about 0° C. to about 60° C. (e.g., about 10° C. to about 40° C. or about 20° C. to about 30° C.).

In some embodiments, the compound of Formula 9 is selected from

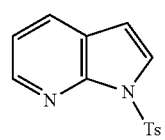
9a

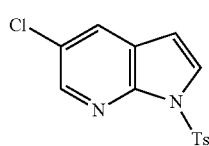
9b 1-tosyl-1H-pyrrolo[2,3-b]pyridine (9a) or 5-chloro-1-tosyl-1H-pyrrolo[2,3-b]pyridine (9b); the compound of Formula 7 is selected from

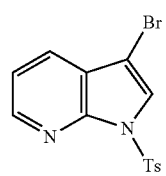
7a

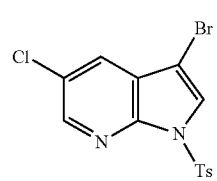
7b 3-bromo-1-tosyl-1H-pyrrolo[2,3-b]pyridine (7a) or 3-bromo-5-chloro-1-tosyl-1H-pyrrolo[2,3-b]pyridine (7b); the compound of Formula 8 is selected from

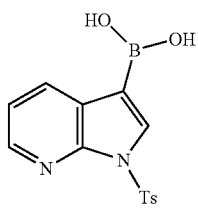
8a

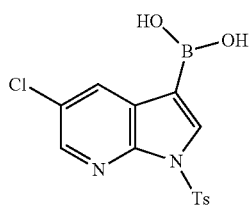
8b 1-tosyl-1H-pyrrolo[2,3-b]pyridin-3-ylboronic acid (8a) or 5-chloro-1-tosyl-1H-pyrrolo[2,3-b]pyridin-3-ylboronic acid (8b); and the compound of Formula 1 is selected from

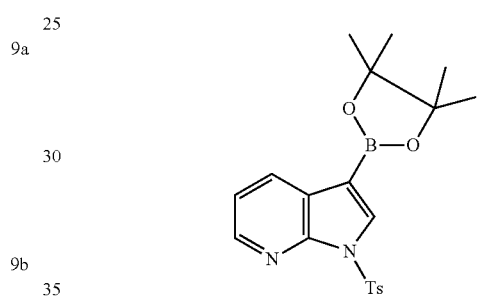
1a

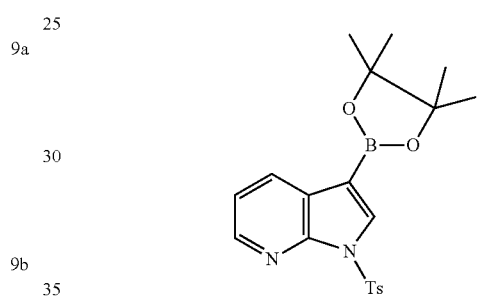
1b 3-(4,4,5,5-tetramethyl-1,3,2-dioxaborolan-2-yl)-1-tosyl-1H-pyrrolo[2,3-b]pyridine (1a) or 5-chloro-3-(4,4,5,5-tetramethyl-1,3,2-dioxaborolan-2-yl)-1-tosyl-1H-pyrrolo[2,3-b]pyridine (1b).

The present invention also provides a process for preparing a compound of Formula 2:

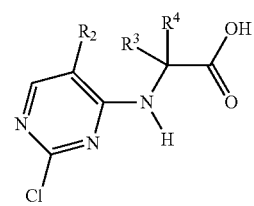
2 wherein $R^2$ is —H or —F; $R^3$ is —$C_{1-4}$ aliphatic optionally substituted with 1-5 occurrences of $R^5$; $R^4$ is —$C_{1-2}$ alkyl optionally substituted with 1-3 occurrences of $R^5$; or $R^3$ and $R^4$ are taken together to form a 3-7 membered carbocyclic or heterocyclic saturated ring optionally substituted with 1-5 occurrences of $R^5$; each $R^5$ is independently selected from halogen, —OCH$_3$, —OH, —NO$_2$, —NH$_2$, —SH, —SCH$_3$, —NHCH$_3$, —CN, or unsubstituted —C$_{1-2}$ aliphatic, or two $R^5$ groups, together with the carbon to which they are attached, form a cyclopropyl ring; comprising the steps: viiia) reacting a compound of Formula 10, wherein $R^8$ is a —C$_{1-4}$ alkyl, with a compound of Formula 11:

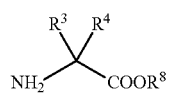

10

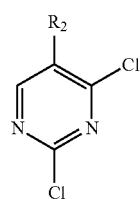

11 in the presence of an organic base and an organic solvent to generate a mixture comprising a compound of Formula 12 and a compound of Formula 13:

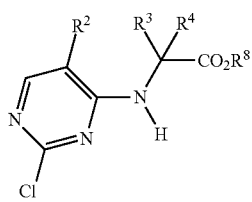

12

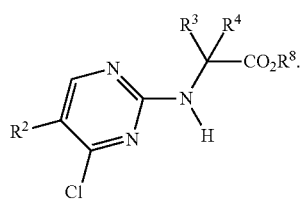

13

Some embodiments further comprising the steps of: ixa) deprotecting the compound of Formula 12 and the compound of Formula 13 in the presence of an inorganic acid to generate a mixture comprising a compound of Formula 2 and a compound of Formula 14:

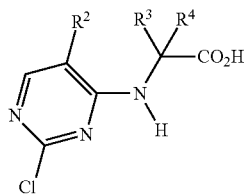

2

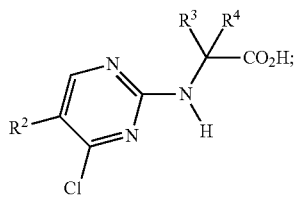

14 xa) reacting the mixture comprising the compound of Formula 2 and the compound of Formula 14 with HCl in the presence of an organic solvent to generate hydrochloride salts of the compound of Formula 2 and the compound of Formula 14; and xia) recrystallizing the mixture comprising the HCl salts of the compound of Formula 2 and the compound of Formula 14 to generate the hydrochloride salt of the compound of Formula 2.

In some embodiments, the compound of Formula 10 is selected from

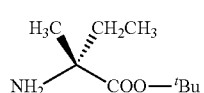

10a

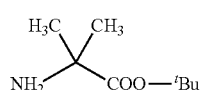

10b (R)-tert-butyl 2-amino-2-methylbutanoate (10a) or tert-butyl 2-amino-2-methylpropanoate (10b); the compound of Formula 11 is selected from

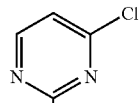

11a

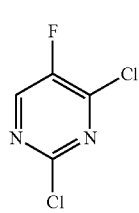

11b 2,4-dichloropyrimidine (11a) or 2,4-dichloro-5-fluoropyrimidine (11b); the compound of Formula 12 is selected from

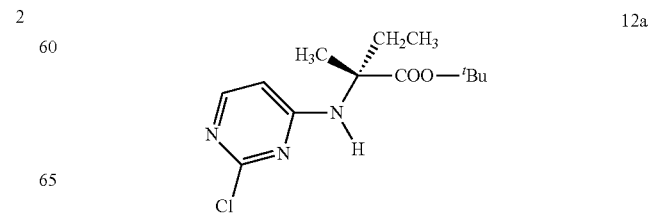

12a

-continued

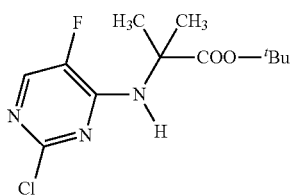
12b (R)-tert-butyl 2-(2-chloropyrimidin-4-ylamino)-2-methylbutanoate (12a) or tert-butyl 2-(2-chloro-5-fluoropyrimidin-4-ylamino)-2-methylpropanoate (12b); and the compound of Formula 13 is selected from

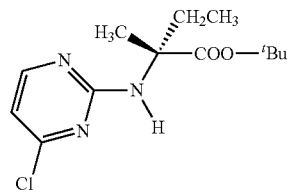
13a

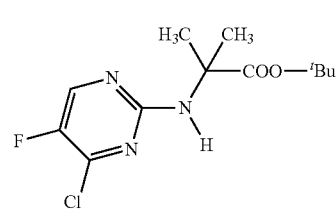
13b (R)-tert-butyl 2-(4-chloropyrimidin-2-ylamino)-2-methylbutanoate (13a) or tert-butyl 2-(4-chloro-5-fluoropyrimidin-2-ylamino)-2-methylpropanoate (13b).

In some embodiments, the compound of Formula 14 is selected from

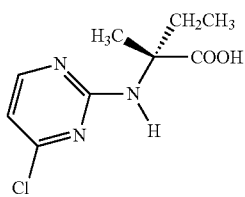
14a

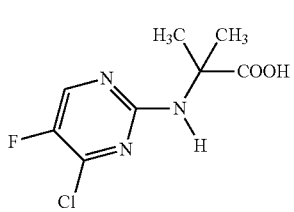
14b (R)-2-(4-chloropyrimidin-2-ylamino)-2-methylbutanoic acid (14a) or 2-(4-chloro-5-fluoropyrimidin-2-ylamino)-2-methylpropanoic acid (14b); and the compound of Formula 2 is selected from

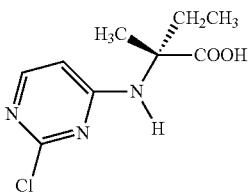
2a

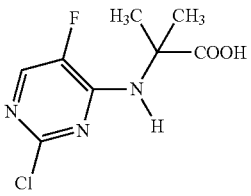
2b (R)-2-(2-chloropyrimidin-4-ylamino)-2-methylbutanoic acid (2a) or 2-(2-chloro-5-fluoropyrimidin-4-ylamino)-2-methylpropanoic acid (2b).

The present invention also provides a process for preparing a compound of Formula 2 comprising the steps:

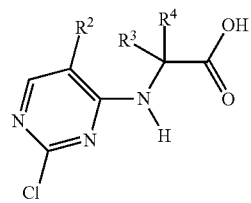
2 wherein $R^2$ is —H or —F; $R^3$ is —$C_{1-4}$ aliphatic optionally substituted with 1-5 occurrences of $R^5$; $R^4$ is —$C_{1-2}$ alkyl optionally substituted with 1-3 occurrences of $R^5$; or $R^3$ and $R^4$ are taken together to form a 3-7 membered carbocyclic or heterocyclic saturated ring optionally substituted with 1-5 occurrences of $R^5$; each $R^5$ is independently selected from halogen, —$OCH_3$, —OH, —$NO_2$, —$NH_2$, —SH, —$SCH_3$, —$NHCH_3$, —CN, or unsubstituted —$C_{1-2}$ aliphatic, or two $R^5$ groups, together with the carbon to which they are attached, form a cyclopropyl ring; comprising the steps: viiib) reacting a compound of Formula 11 with an acid salt of a compound of Formula 15 in the presence of a solvent and a base to generate the compound Formula 2

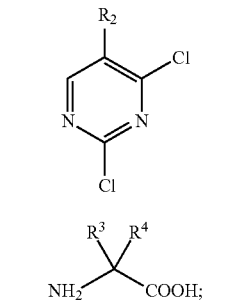

11

15 and
ixb) reacting the compound of Formula 2 with HCl to generate the hydrochloride salt of the compound of Formula 2.

In some embodiments, the acid salt of a compound of Formula 15 is a hydrochloride salt of the compound of Formula 15.

In some embodiments, the base of step viiib) is an inorganic base selected from tripotassium phosphate, dipotassium hydrogen phosphate, dipotassium carbonate, disodium carbonate, trisodium phosphate, disodium hydrogen phosphate, or any combination thereof.

In some embodiments, the solvent of step viiib) comprises water.

In some embodiments, the solvent of step viiib) further comprises an alcohol selected from methanol, ethanol, propanol, iso-propanol, butanol, tert-butanol, or any combination thereof.

In some embodiments, the reaction of step viiib) is performed at a temperature of from about 70° C. to about 120° C. (e.g., from about 80° C. to about 100° C.).

In some embodiments, the compound of Formula 11 is selected from

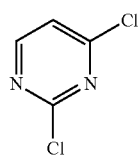

11a

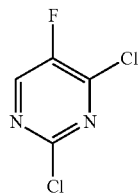

11b 2,4-dichloropyrimidine (11a) or 2,4-dichloro-5-fluoropyrimidine (11b); the compound of Formula 15 is selected from

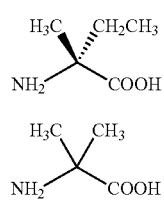

15a

15b

D-isovaline (15a) or 2-amino-2-methylpropanoic acid (15b); and the compound of Formula 2 is selected from

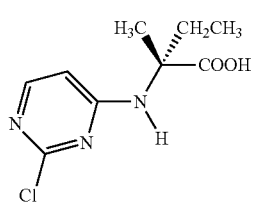

2a

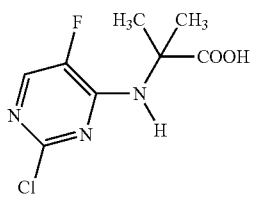

2b (R)-2-(2-chloropyrimidin-4-ylamino)-2-methylbutanoic acid (2a) or 2-(2-chloro-5-fluoropyrimidin-4-ylamino)-2-methylpropanoic acid (2b).

In some embodiments, the compound of Formula I is:

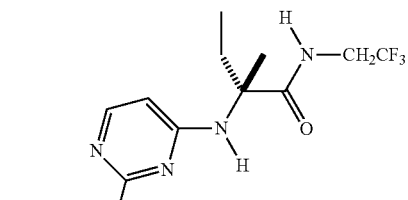

Ia

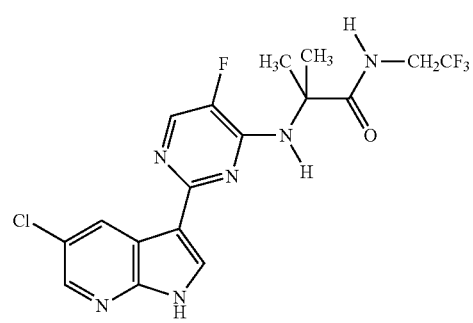

Ib (R)-2-(2-(1H-pyrrolo[2,3-b]pyridin-3-yl)pyrimidin-4-ylamino)-2-methyl-N-(2,2,2-trifluoroethyl)butanamide (Ia) or 2-(2-(5-chloro-1H-pyrrolo[2,3-b]pyridin-3-yl)-5-fluoropyrimidin-4-ylamino)-2-methyl-N-(2,2,2-trifluoroethyl)propanamide (Ib).

The present invention also provides a process for preparing (R)-2-(2-(1H-pyrrolo[2,3-b]pyridin-3-yl)pyrimidin-4-ylamino)-2-methyl-N-(2,2,2-trifluoroethyl)butanamide of Formula Ia:

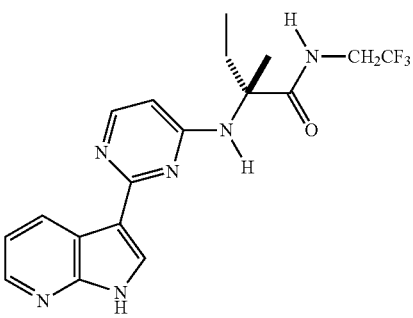

Ia or a pharmaceutically acceptable salt thereof, comprising the step of: i) reacting 3-(4,4,5,5-tetramethyl-1,3,2-dioxaborolan-2-yl)-1-tosyl-1H-pyrrolo[2,3-b]pyridine (1a) with the hydrochloride salt of (R)-2-(2-chloropyrimidin-4-ylamino)-2-methylbutanoic acid (2a),

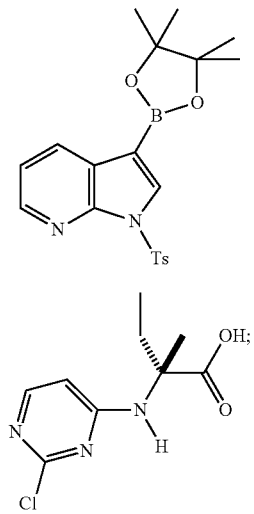

1a

2a in the presence of water, an organic solvent, an inorganic base, and a palladium catalyst to generate (R)-2-methyl-2-(2-(1-tosyl-1H-pyrrolo[2,3-b]pyridin-3-yl)pyrimidin-4-ylamino)butanoic acid of Formula Ia.

Some embodiments further comprise the step of reacting

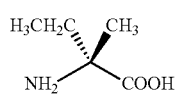

11a 2,4-dichloropyrimidine (11a), and

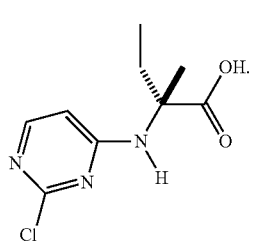

15a

D-isovaline (15a) to generate the hydrochloride salt of (R)-2-(2-chloropyrimidin-4-ylamino)-2-methylbutanoic acid hydrochloride (2a)

2a

The present invention also provides a process for preparing 2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib:

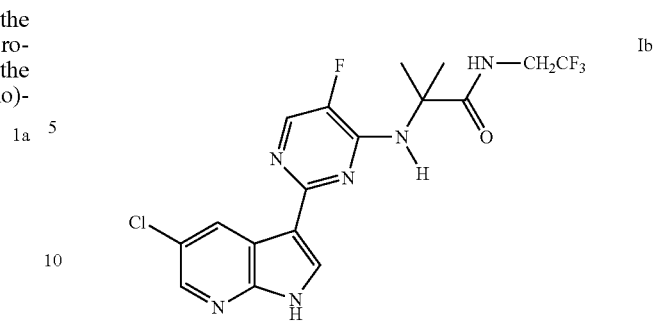

Ib or a pharmaceutically acceptable salt thereof, comprising the step of: i) reacting 5-chloro-3-(4,4,5,5-tetramethyl-1,3,2-dioxaborolan-2-yl)-1-tosyl-1H-pyrrolo[2,3-b]pyridine (1b) with the hydrochloride salt of 2-(2-chloro-5-fluoropyrimidin-4-ylamino)-2-methylpropanoic acid hydrochloride (2b),

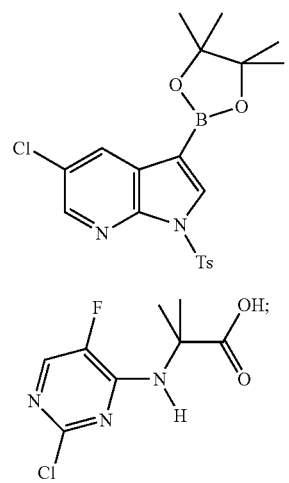

1b

2b in the presence of water, an organic solvent, an inorganic base, and a palladium catalyst to generate 2-(2-(5-chloro-1-tosyl-1H-pyrrolo[2,3-b]pyridin-3-yl)-5-fluoropyrimidin-4-ylamino)-2-methylpropanoic acid of Formula Ib.

Some embodiments further comprise the step of reacting

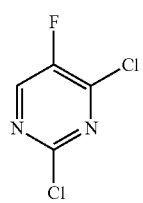

11b 2,4-dichloro-5-fluoropyrimidine (11b), and

15b 2-amino-2-methylpropanoic acid (15b) to generate the hydrochloride salt of 2-(2-chloro-5-fluoropyrimidin-4-ylamino)-2-methylpropanoic acid (2b)

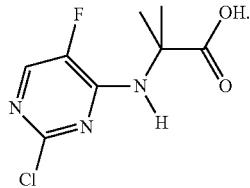

The present invention also provides compounds useful as intermediates in the processes of the present invention.

The present invention also provides a solid form of (R)-2-(2-(1H-pyrrolo[2,3-b]pyridin-3-yl)pyrimidin-4-ylamino)-2-methylbutanoic acid (4a) designated as Form E. In some embodiments, solid Form E is characterized by one or more peaks corresponding to 2-theta values measured in degrees of 7.1±0.2, 8.2±0.2, 23.9±0.2, and 24.8±0.2 in an X-ray powder diffraction pattern.

The present invention also provides a solid form of (R)-2-(2-(1H-pyrrolo[2,3-b]pyridin-3-yl)pyrimidin-4-ylamino)-2-methylbutanoic acid (4a) designated as Form B. In some embodiments, the solid Form B is characterized by one or more peaks corresponding to 2-theta values measured in degrees of 9.2±0.2, 18.1±0.2, 19.1±0.2, and 32.0±0.2 in an X-ray powder diffraction pattern. In other embodiments, solid Form B is further characterized by one or more peaks corresponding to 2-theta values measured in degrees of 21.4±0.2, 30.1±0.2, 29.9±0.2, and 26.1±0.2 in an X-ray powder diffraction pattern.

The present invention also provides a solid form of (R)-2-(2-(1H-pyrrolo[2,3-b]pyridin-3-yl)pyrimidin-4-ylamino)-2-methyl-N-(2,2,2-trifluoroethyl)butanamide (Ia) designated as Form A. In some embodiments, solid Form A is characterized by one or more peaks corresponding to 2-theta values measured in degrees of 23.7±0.2, 11.3±0.2, 19.3±0.2, and 15.4±0.2 in an X-ray powder diffraction pattern. In other embodiments, solid Form A is further characterized by one or more peaks corresponding to 2-theta values measured in degrees of 28.9±0.2 and 21.5±0.2 in an X-ray powder diffraction pattern.

DETAILED DESCRIPTION OF THE INVENTION

Figure 1:
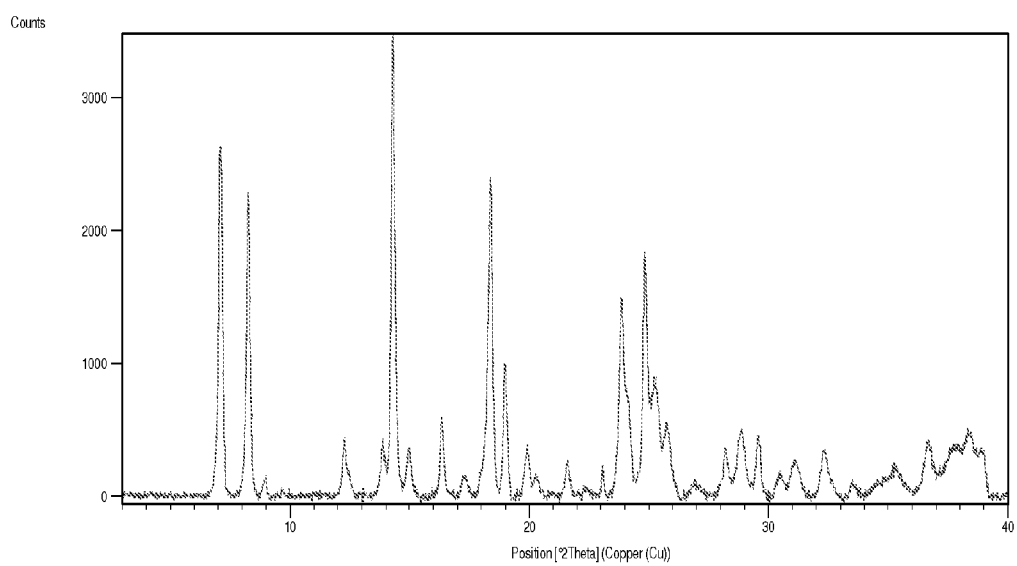
FIG. 1 is an XRPD pattern of Form E of Compound (4a).

The present invention provides a process for preparing a compound of Formula I:

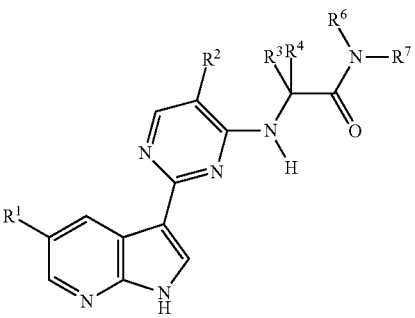

or a pharmaceutically acceptable salt thereof, wherein:
$R^1$ is —H, —Cl or —F;
$R^2$ is —H or —F;
$R^3$ is —$C_{1-4}$ aliphatic optionally substituted with 1-5 occurrences of $R^5$;
$R^4$ is —$C_{1-2}$ alkyl optionally substituted with 1-3 occurrences of $R^5$; or
$R^3$ and $R^4$ are taken together to form a 3-7 membered carbocyclic or heterocyclic saturated ring optionally substituted with 1-5 occurrences of $R^5$;
each $R^5$ is independently selected from halogen, —OCH$_3$, —OH, —NO$_2$, —NH$_2$, —SH, —SCH$_3$, —NHCH$_3$, —CN, or unsubstituted —$C_{1-2}$ aliphatic, or
two $R^5$ groups, together with the carbon to which they are attached, form a cyclopropyl ring;
$R^6$ is —H or unsubstituted —$C_{1-2}$ alkyl; and
$R^7$ is a —CH$_2$CR$_3$ or —(CH$_2$)$_2$CR$_3$ wherein each R is independently —H or —F;
comprising the step of:
i) reacting a compound of Formula 1 with a hydrochloride (HCl) salt of a compound Formula 2

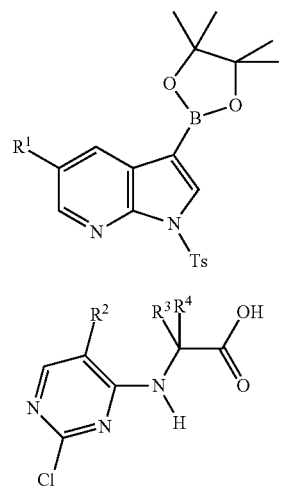

in the presence of water, an organic solvent, a base, and a transition metal (e.g., Pd) catalyst to generate a compound of Formula I.

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$-], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)—when used internally, wherein R$^X$ and R$^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of Rx and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di(such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl; or (haloalkyl)heteroaryl [e.g., trihaloalkylheteroaryl].

A "heteroaraliphatic (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$— where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

In general, the term "substituted," whether preceded by the term "optionally" or not, refers to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Chemical structures and nomenclature are derived from ChemDraw, version 11.0.1, Cambridge, Mass.

It is noted that the use of the descriptors "first", "second", "third", or the like is used to differentiate separate elements (e.g., solvents, reaction steps, processes, reagents, or the like) and may or may not refer to the relative order or relative chronology of the elements described.

As used herein, the term "pharmaceutically acceptable salt" refers to those salts which are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis" 4th Ed, Wuts, P. G. M. and Greene, T. W., Wiley-Interscience, New York: 2006, which is incorporated herein by reference.

Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are benzenesulfonylchloride p-toluenesulfonyl and the like, including, but not limited to, tosyl.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools, probes in biological assays, or JAK inhibitors with improved therapeutic profile.

As used herein, the term "solvent" also includes mixtures of solvents.

II. Synthetic Processes

The present invention provides a process for preparing a compound of Formula I:

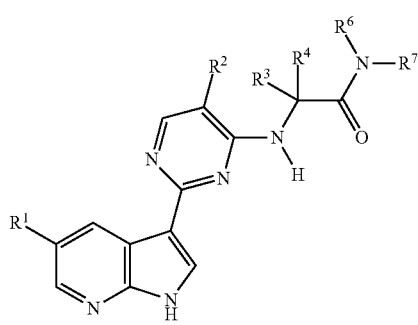

I or a pharmaceutically acceptable salt thereof, wherein:
R$^1$ is —H, —Cl or —F;
R$^2$ is —H or —F;
R$^3$ is —C$_{1-4}$ aliphatic optionally substituted with 1-5 occurrences of R$^5$;
R$^4$ is —C$_{1-2}$ alkyl optionally substituted with 1-3 occurrences of R$^5$; or
R$^3$ and R$^4$ are taken together to form a 3-7 membered carbocyclic or heterocyclic saturated ring optionally substituted with 1-5 occurrences of R$^5$;
each R$^5$ is independently selected from halogen, —OCH$_3$, —OH, —NO$_2$, —NH$_2$, —SH, —SCH$_3$, —NHCH$_3$, —CN, or unsubstituted —C$_{1-2}$ aliphatic, or
two R$^5$ groups, together with the carbon to which they are attached, form a cyclopropyl ring;
R$^6$ is —H or unsubstituted —C$_{1-2}$ alkyl; and
R$^7$ is a —CH$_2$CR$_3$ or —(CH$_2$)$_2$CR$_3$ wherein each R is independently —H or —F;
comprising the step of:
i) reacting a compound of Formula 1 with a compound Formula 2 or a hydrochloride salt of a compound of Formula 2

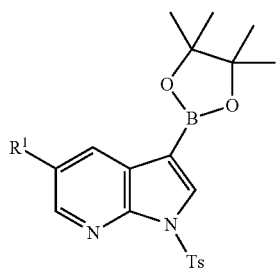

1

-continued

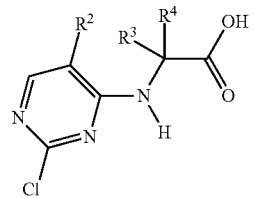

2 in the presence of water, an organic solvent, a base, and a transition metal (e.g., Pd) catalyst to generate a compound of Formula I.

The present invention provides a process for preparing a compound of Formula I:

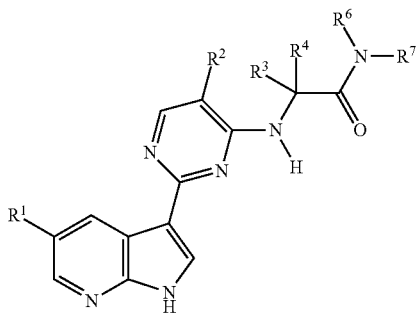

I or a pharmaceutically acceptable salt thereof, wherein:
R$^1$ is —H, —Cl or —F;
R$^2$ is —H or —F;
R$^3$ is —C$_{1-4}$ aliphatic optionally substituted with 1-5 occurrences of R$^5$;
R$^4$ is —C$_{1-2}$ alkyl optionally substituted with 1-3 occurrences of R$^5$; or
R$^3$ and R$^4$ are taken together to form a 3-7 membered carbocyclic or heterocyclic saturated ring optionally substituted with 1-5 occurrences of R$^5$;
each R$^5$ is independently selected from halogen, —OCH$_3$, —OH, —NO$_2$, —NH$_2$, —SH, —SCH$_3$, —NHCH$_3$, —CN, or unsubstituted —C$_{1-2}$ aliphatic, or
two R$^5$ groups, together with the carbon to which they are attached, form a cyclopropyl ring;
R$^6$ is —H or unsubstituted —C$_{1-2}$ alkyl; and
R$^7$ is a —CH$_2$CR$_3$ or —(CH$_2$)$_2$CR$_3$ wherein each R is independently —H or —F;
comprising the steps of:
i) reacting a compound of Formula 1 with a hydrochloride salt of a compound Formula 2

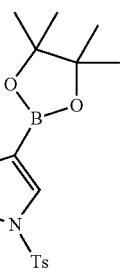

1

-continued

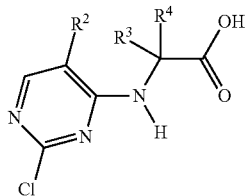

in the presence of water, an organic solvent, a base, and a transition metal catalyst to generate a compound of Formula 3

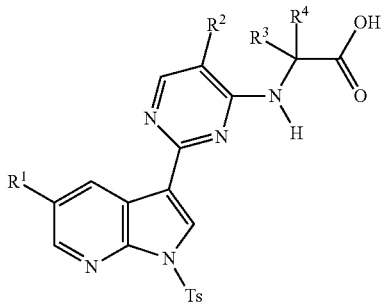

ii) deprotecting the compound of Formula 3 to generate a compound of Formula 4,

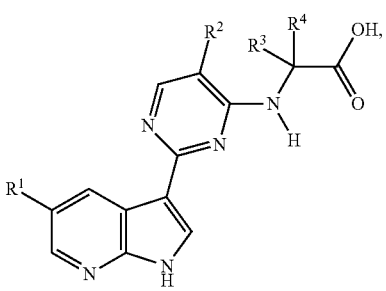

and iii) reacting the compound of Formula 4 with HNR⁶R⁷ in the presence of a coupling agent and an organic solvent to generate the compound of Formula I.

The present invention provides a process for preparing (R)-2-(2-(1H-pyrrolo[2,3-b]pyridin-3-yl)pyrimidin-4-ylamino)-2-methyl-N-(2,2,2-trifluoroethyl)butanamide of Formula Ia:

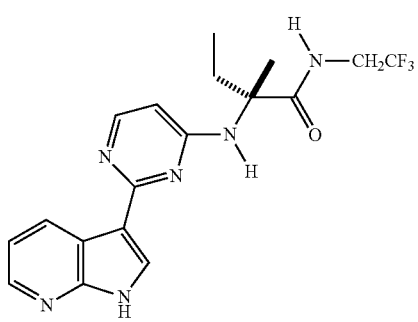

comprising the step of:

i) reacting 3-(4,4,5,5-tetramethyl-1,3,2-dioxaborolan-2-yl)-1-tosyl-1H-pyrrolo[2,3-b]pyridine (1a) and (R)-2-(2-chloropyrimidin-4-ylamino)-2-methylbutanoic acid hydrochloride (2a)

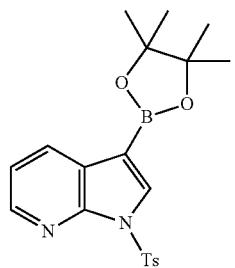

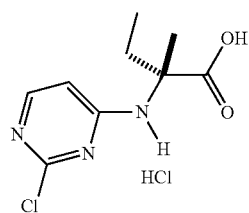

in the presence of water, an organic solvent, an inorganic base, and a transition metal catalyst to generate (R)-2-(2-(1H-pyrrolo[2,3-b]pyridin-3-yl)pyrimidin-4-ylamino)-2-methyl-N-(2,2,2-trifluoroethyl)butanamide of Formula Ia.

The present invention also provides a process for preparing (R)-2-(2-(1H-pyrrolo[2,3-b]pyridin-3-yl)pyrimidin-4-ylamino)-2-methyl-N-(2,2,2-trifluoroethyl)butanamide of Formula Ia:

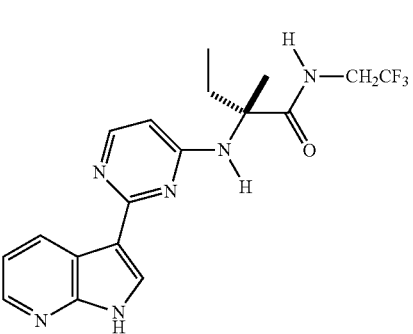

comprising the steps of:

i) reacting 3-(4,4,5,5-tetramethyl-1,3,2-dioxaborolan-2-yl)-1-tosyl-1H-pyrrolo[2,3-b]pyridine (1a) with the hydrochloride (HCl) salt of (R)-2-(2-chloropyrimidin-4-ylamino)-2-methylbutanoic acid hydrochloride (2a),

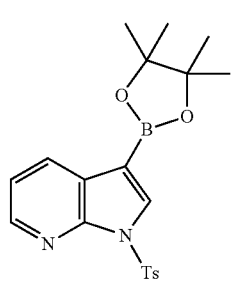

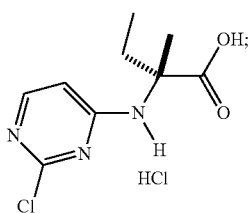

2a in the presence of water, an organic solvent, an inorganic base, and a transition metal (e.g., Pd) catalyst to generate (R)-2-methyl-2-(2-(1-tosyl-1H-pyrrolo[2,3-b]pyridin-3-yl) pyrimidin-4-ylamino)butanoic acid of Formula 3a.

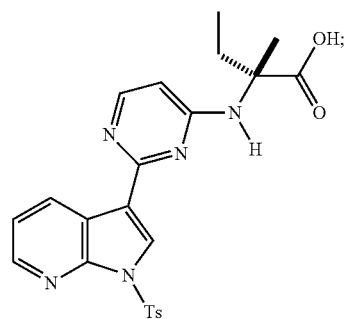

3a ii) deprotecting the compound of Formula 3a under basic conditions to generate (R)-2-(2-(1H-pyrrolo[2,3-b]pyridin-3-yl)pyrimidin-4-ylamino)-2-methylbutanoic of Formula 4a,

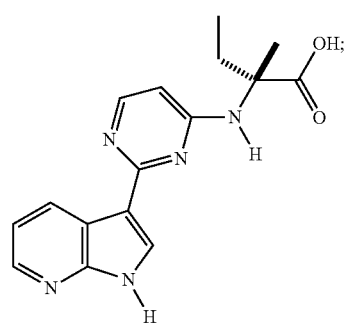

4a and iii) reacting the compound of Formula 4a with 2,2,2-trifluoroethylamine (CF₃CH₂NH₂); in the presence of a coupling agent and an organic solvent to generate the compound of Formula Ia.

The present invention provides for a process for preparing 2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib:

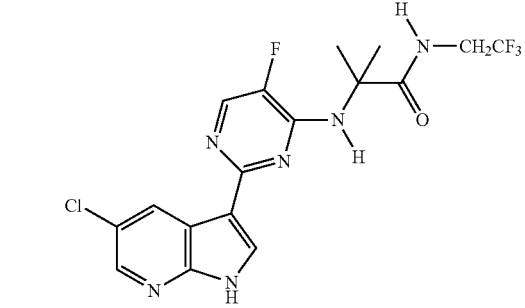

Ib comprising the steps of:

i) reacting 5-chloro-3-(4,4,5,5-tetramethyl-1,3,2-dioxaborolan-2-yl)-1-tosyl-1H-pyrrolo[2,3-b]pyridine (1b) with 2-(2-chloro-5-fluoropyrimidin-4-ylamino)-2-methylpropanoic acid hydrochloride (2b),

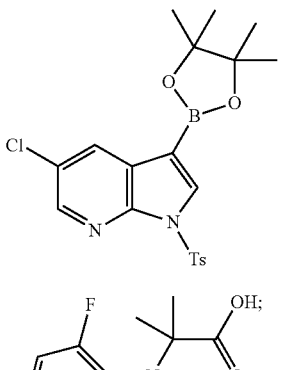

1b

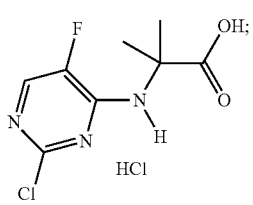

2b in the presence of water, an organic solvent, an inorganic base, and a transition metal catalyst to generate 2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib.

The present invention also provides for a process for preparing 2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib:

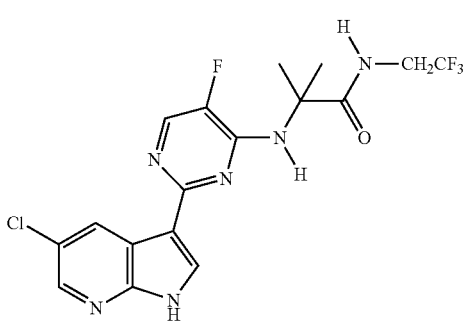

Ib comprising the steps of:

i) reacting or coupling 5-chloro-3-(4,4,5,5-tetramethyl-1,3,2-dioxaborolan-2-yl)-1-tosyl-1H-pyrrolo[2,3-b]pyridine (1b) with 2-(2-chloro-5-fluoropyrimidin-4-ylamino)-2-methylpropanoic acid hydrochloride (2b),

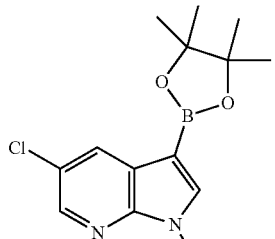

1b

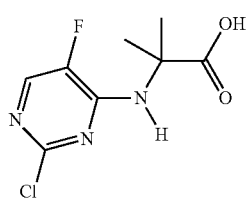

2b in the presence of water, an organic solvent, an inorganic base, and a transition metal catalyst to generate 2-(2-(5-chloro-1-tosyl-1H-pyrrolo[2,3-b]pyridin-3-yl)-5-fluoropyrimidin-4-ylamino)-2-methylpropanoic acid of Formula 3b,

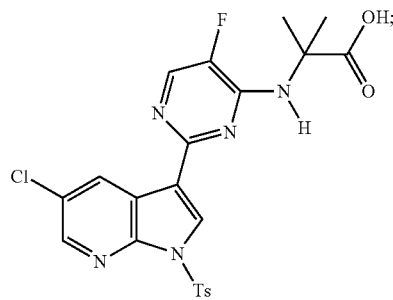

3b ii) deprotecting the compound of Formula 3b under basic conditions to generate 2-(2-(5-chloro-1H-pyrrolo[2,3-b]pyridin-3-yl)-5-fluoropyrimidin-4-ylamino)-2-methylpropanoic acid of Formula 4b

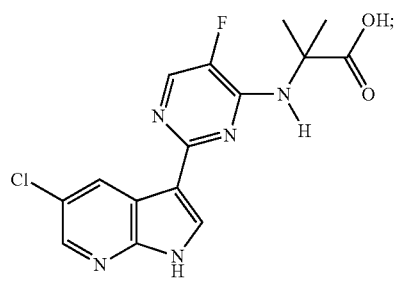

4b and iii) reacting the compound of Formula 4b with 2,2,2-trifluoroethylamine ($CF_3CH_2NH_2$), in the presence of a coupling agent and an organic solvent to generate the compound of Formula Ib.

A. Step i)

In some embodiments, the organic solvent of step i) above is an aprotic solvent. For example, the aprotic solvent of step i) comprises acetonitrile, toluene, N,N-dimethylformamide, N,N-dimethylacetamide, acetone, methyl tert-butyl ether, or any combination thereof. In other examples, the aprotic solvent is acetonitrile.

In some embodiments, the organic solvent of step i) is a protic solvent. For example, the protic solvent comprises ethanol, methanol, isopropanol, or any combination thereof. In other examples, the protic solvent comprises ethanol, isopropanol, or any combination thereof. For instance, the protic solvent comprises isopropanol.

In some embodiments, the base of step i) is an inorganic base. Examples of inorganic bases include tripotassium phosphate, dipotassium hydrogen phosphate, dipotassium carbonate, disodium carbonate, trisodium phosphate, or disodium hydrogen phosphate. In some embodiments, the inorganic base is tripotassium phosphate, dipotassium hydrogen phosphate, trisodium phosphate, or disodium hydrogen phosphate. In other embodiments, the inorganic base is tripotassium phosphate. Other examples of inorganic bases include alkali metal hydroxides such as NaOH, KOH, or any combination thereof.

In some embodiments, the transition metal catalyst in step i) is a palladium catalyst. Examples of palladium catalysts include palladium(II)acetate, tetrakis(triphenylphosphine)palladium(0), tris(dibenzylideneacetone)dipalladium(0), or any combination thereof. In some embodiments, the palladium-based catalyst is palladium(II)acetate. Other examples of palladium catalysts include

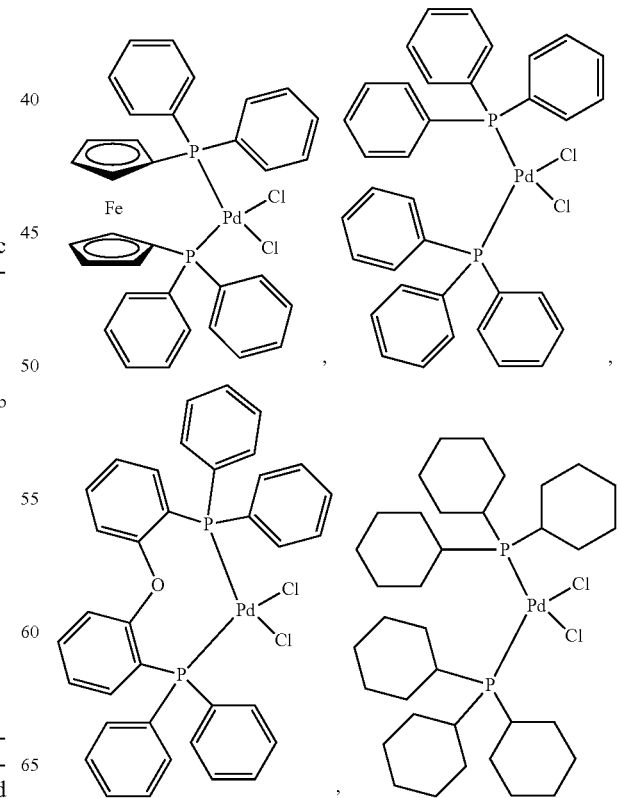

-continued

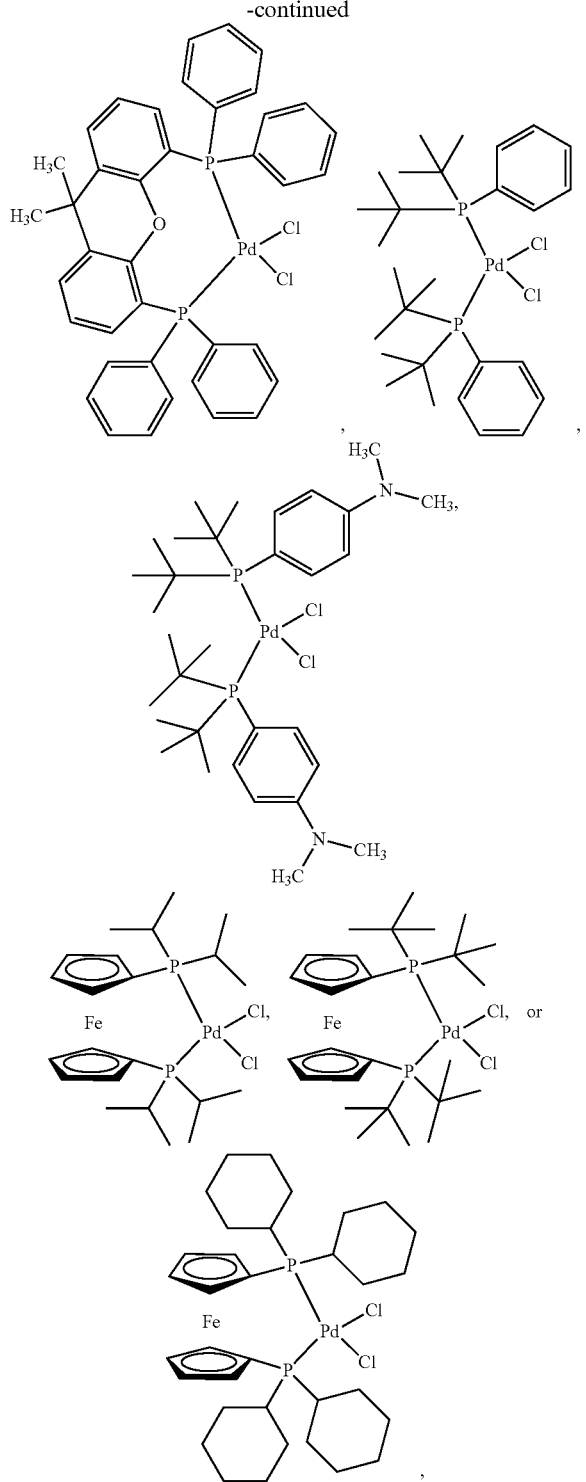

, or any combination thereof.

In some embodiments, the palladium catalyst is formed in situ.

In some embodiments, the water, organic solvent, and inorganic base of step i) combine to comprise a biphasic mixture. In other embodiments, in step i) where the palladium catalyst is formed in situ, this mixture additionally comprises a phosphine ligand. Examples of phosphine ligands include a triarylphosphine ligand or a trialkylphosphine ligand. In some embodiments, the phosphine ligand is a triarylphosphine ligand. For example, the triarylphosphine ligand is triphenylphosphine.

In some embodiments, step i) further comprises adding a catalyst (e.g., a palladium catalyst as described above) and compound of Formula 1 after the reaction has run for a period of more than 1 hour (e.g., about 2 hours or more or about 5 hours).

In some embodiments, step i) further includes adding a catalyst (e.g., a palladium catalyst as described above) and compound of Formula 1 after the reaction is about 86% complete.

In some embodiments, the reaction of step i) is performed at a temperature between about 50° C. and about 110° C. For example, the reaction of step i) is performed at a temperature between about 60° C. and about 95° C. In other embodiments, the reaction of step i) is performed at a temperature between about 70° C. and about 80° C.

In some embodiments, step i) is performed with agitation. For example, the reaction is performed in a vessel containing a stir bar that agitates the reaction mixture.

In some embodiments, the reaction of step i) is completed in about 17 hours.

In some embodiments, the reaction of step i) is about 86% complete in a period of about 5 hours.

In other embodiments, the reaction of step i) is about 99% complete in a period of about 17 hours.

B. Step ii)

In some embodiments, step ii) comprises deprotecting the compound of Formula 3 in the presence of a base. In some examples, the base comprises an inorganic base such as an alkali metal hydroxide. Examples of alkali metal hydroxides include NaOH, KOH, or any combination thereof. In other embodiments, step ii) comprises deprotecting the compound of Formula 3 in the presence of KOH.

In some embodiments, the alkali-metal hydroxide base has a concentration of about 2N to about 6N. In other embodiments, the alkali-metal hydroxide base has a concentration of about 4N. For example, in some embodiments, the concentration of potassium hydroxide is about 3N to about 5N. In other embodiments, the concentration of potassium hydroxide is about 4N.

In some embodiments, the deprotection reaction in step ii) is performed at a temperature between about 60° C. and about 110° C. For example the deprotection reaction in step ii) is performed at a temperature between about 65° C. and about 95° C. In other examples, the deprotection reaction in step ii) is performed at a temperature between about 70° C. and about 80° C.

C. Step iii)

In some embodiments, the coupling agent of step iii) is propylphosphonic anhydride.

In some embodiments, the organic solvent of step iii) comprises a halogenated hydrocarbon, an alkyl substituted tetrahydrofuran, or any combination thereof. For example, the organic solvent comprises an alkyl substituted tetrahydrofuran comprising 2-methyltetrahydrofuran (2-MeTHF).

In some embodiments, the organic solvent of step iii) is a halogenated hydrocarbon. Examples of halogenated hydrocarbons include dichloromethane or dichloroethane. In some embodiments, the halogenated hydrocarbon is dichloromethane.

In some embodiments, the reaction of step iii) is performed in the presence of a base. In some examples, the base is an organic base. In some embodiments, the organic base of step iii) above is a tertiary amine. For example, the organic base in step iii) is N,N-diisopropylethylamine, trimethylamine, or any combination thereof.

In some embodiments, the reaction of step iii) is performed at a temperature of about 40° C. or less. For example, the reaction of step iii) is performed at a temperature of about 35° C. In still other embodiments, the reaction of step iii) is performed at a temperature of about 25° C.

In some embodiments, $HNR^6R^7$ in step iii) is $CF_3(CH_2)_2NH_2$ or $CF_3CH_2NH_2$. In other embodiments, $HNR^6R^7$ in step iii) is $CH_3(CH_2)_2NH_2$ or $CH_3CH_2NH_2$. In still other embodiments, $HNR^6R^7$ in step iii) is $CF_3CH_2NH_2$ or $CH_3CH_2NH_2$. In further embodiments, $HNR^6R^7$ in step iii) is $CF_3CH_2NH_2$.

In some embodiments, the process further comprises the additional step of purifying a compound of Formula 4. For example, after step ii) and before step iii), step iiia) comprises crystallizing a compound of Formula 4. In some embodiments, step iiia) is repeated.

In some embodiments, the crystallization in step iiia) is performed under basic conditions. In other embodiments, the crystallization in step iiia) is performed under acidic conditions. In still other embodiments, the crystallization is performed in basic conditions followed by a subsequent crystallization, which is performed under acidic conditions, or vice versa.

In some embodiments, the process further comprises the additional steps after step ii) and before step iii) of:
  iiia) adding an organic solvent, adjusting the pH of the mixture to <1.0 using concentrated HCl; and
  iiid) drying the solids.

In some embodiments, the process further comprises the additional steps after step ii) and before step iii) of:
  iiia) adding an organic solvent, adjusting the pH of the mixture to <1.0 using concentrated HCl;
  iiib) adding charcoal and filtering;
  iiic) repeating step iiib) two times; and
  iiid) drying the solids.

In some embodiments, the organic solvent in step iiia) is isopropyl acetate.

D. Additional Steps

Some embodiments further comprise comprising the steps of:
  iva) reacting a compound of Formula 5 with bromine in an organic solvent to generate a compound of Formula 6:

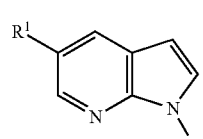

5

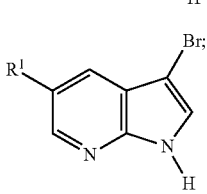

6 va) reacting the compound of Formula 6 with p-toluenesulfonyl chloride to generate a compound of Formula 7:

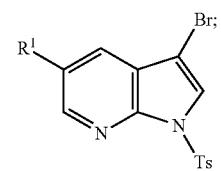

7 vi) reacting the compound of Formula 7 with triisopropyl borate, in the presence of an organic solvent and a strong lithium base to generate a compound of Formula 8:

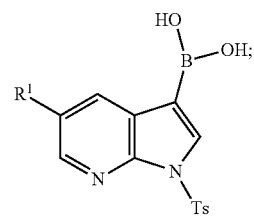

8 and
  vii) esterifying a compound of Formula 8 with pinacolate alcohol in an organic solvent to generate a compound of Formula 1.

Some alternative embodiments further comprise the steps of:
  ivb) reacting a compound of Formula 5 with p-toluenesulfonyl chloride to generate a compound of Formula 9:

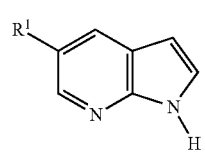

5

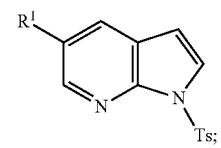

9 vb) reacting the compound of Formula 9 with N-bromosuccinimide to generate a compound of Formula 7:

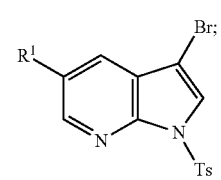

7 vi) reacting the compound of Formula 7 with triisopropyl borate, in the presence of an organic solvent and a strong lithium base to generate a compound of Formula 8:

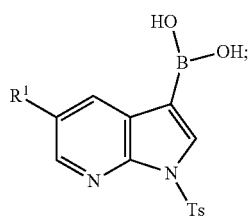

and vii) esterifying the compound of Formula 8 with pinacolate alcohol in an organic solvent to generate a compound of Formula 1.

The present invention also provides for a process for preparing a compound of Formula 1

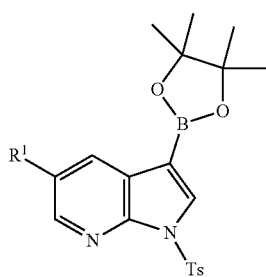

wherein

R¹ is —H, —Cl, or —F;

comprising the steps of:

iva) reacting a compound of Formula 5 with bromine (Br₂) in an organic solvent to generate a compound of Formula 6:

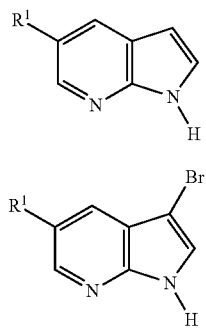

va) reacting the compound of Formula 6 in an organic solvent with an N-protecting group (e.g., p-toluenesulfonyl chloride) to generate a compound of Formula 7 where PG is a protecting group (e.g., Ts):

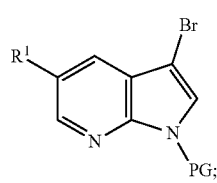

in particular reacting a compound of Formula 6 in an organic solvent with p-toluenesulfonyl chloride to generate a compound of Formula 7:

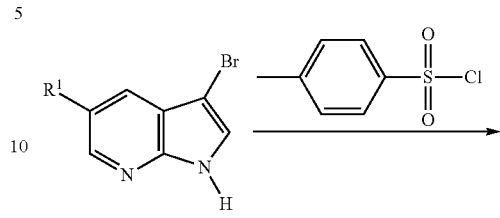

vi) reacting the compound of Formula 7 in an organic solvent with triisopropyl borate, in the presence of a strong lithium base to generate a compound of Formula 8:

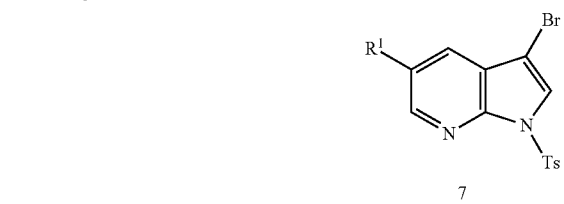

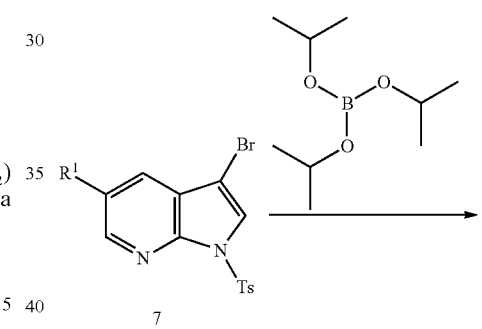

and iv) esterifying the compound of Formula 8 with pinacolate alcohol in an organic solvent to generate a compound of Formula 1:

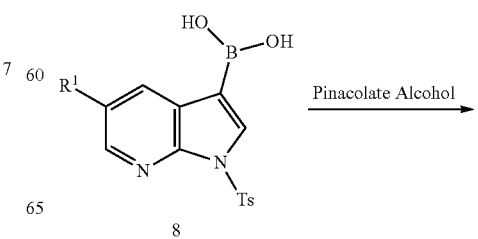

-continued

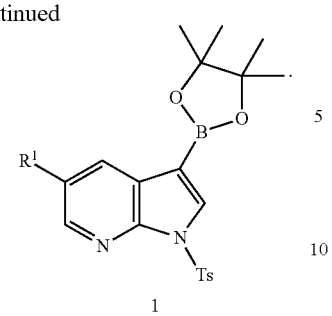

1

The present invention provides for a process for preparing a compound of Formula Ia:

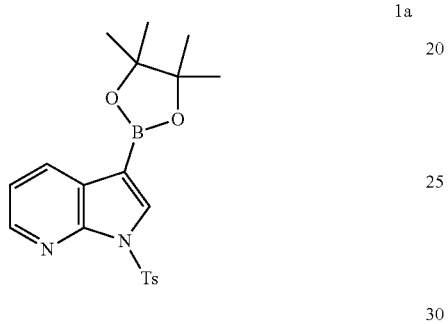

1a comprising the steps of:
iva) reacting 1H-pyrrolo[2,3-b]pyridine (5a) with bromine (Br₂) in an organic solvent to generate 3-bromo-1H-pyrrolo[2,3-b]pyridine (6a)

5a

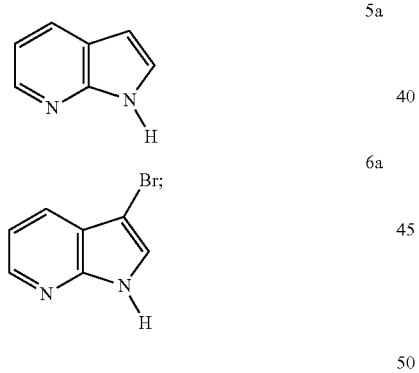

6a va) reacting 3-bromo-1H-pyrrolo[2,3-b]pyridine (6a) in an organic solvent with p-toluenesulfonyl chloride to generate 3-bromo-1-tosyl-1H-pyrrolo[2,3-b]pyridine (7a)

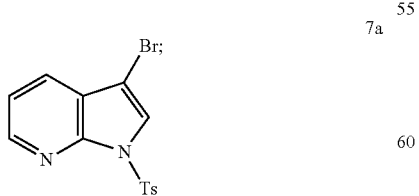

7a vi) reacting 3-bromo-1-tosyl-1H-pyrrolo[2,3-b]pyridine (7a) in an organic solvent with triisopropyl borate in the presence of a strong lithium base to generate 1-tosyl-1H-pyrrolo[2,3-b]pyridin-3-ylboronic acid (8a)

8a and
vii) esterifying 1-tosyl-1H-pyrrolo[2,3-b]pyridin-3-ylboronic acid (8a) with pinacolate alcohol in an organic solvent to generate 3-(4,4,5,5-tetramethyl-1,3,2-dioxaborolan-2-yl)-1-tosyl-1H-pyrrolo[2,3-b]pyridine (1a).

The present invention provides for a process for preparing a compound of Formula Ib:

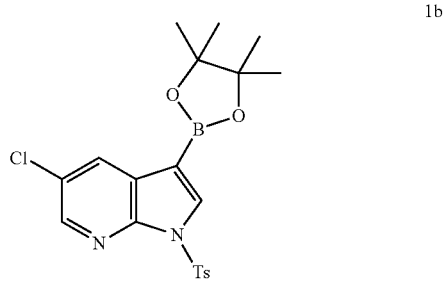 [SMILES: Cc1ccc(S(=O)(=O)n2cc(B3OC(C)(C)C(C)(C)O3)c3cc(Cl)cnc32)cc1]

1b comprising the steps of:
iva) reacting 5-chloro-1H-pyrrolo[2,3-b]pyridine (5b) with bromine (Br₂) in an organic solvent to generate 5-chloro-3-bromo-1H-pyrrolo[2,3-b]pyridine (6b)

5b

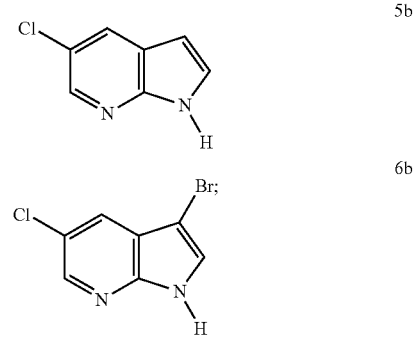

6b va) reacting 5-chloro-3-bromo-1H-pyrrolo[2,3-b]pyridine (6b) in an organic solvent with p-toluenesulfonyl chloride to generate 5-chloro-3-bromo-1-tosyl-1H-pyrrolo[2,3-b]pyridine (7b)

7b vi) reacting 5-chloro-3-bromo-1-tosyl-1H-pyrrolo[2,3-b]pyridine (7b) in an organic solvent with triisopropyl borate in the presence of a strong lithium base to generate 5-chloro-1-tosyl-1H-pyrrolo[2,3-b]pyridin-3-ylboronic acid (8b)

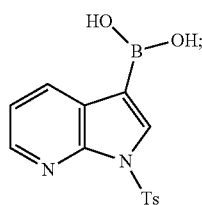

and vii) esterifying 1-tosyl-1H-pyrrolo[2,3-b]pyridin-3-ylboronic acid (8b) with pinacolate alcohol in an organic solvent to generate 5-chloro-3-(4,4,5,5-tetramethyl-1,3,2-dioxaborolan-2-yl)-1-tosyl-1H-pyrrolo[2,3-b]pyridine (1b).

In some embodiments, the organic solvent in step iva) is an aprotic solvent. For example, the aprotic solvent is dimethylformamide.

In some embodiments, the reaction in step iva) is performed at a temperature of about −5° C. to about 30° C. In other embodiments, the reaction is performed at a temperature of about 0° C. to about 10° C.

In some embodiments, the organic solvent in step va) above is an aprotic solvent. In other embodiments, the aprotic solvent is tetrahydrofuran.

In some embodiments, step va) is performed in the presence of sodium hydride.

In some embodiments, the reaction in step va) is performed at a temperature of about 0° C. to about 30° C. In some embodiments, the reaction is performed at a temperature of about 5° C. to about 25° C. In other embodiments, the reaction is performed at a temperature of about 10° C. to about 20° C.

In some embodiments, the strong lithium base in step vi) is n-butyl lithium.

In some embodiments, the reaction in step vi) is performed at a temperature of about −100° C. to about −70° C. In other embodiments, the reaction is performed at a temperature of about −90° C. to about −80° C.

In some embodiments, the organic solvent in step vii) above is a halogenated hydrocarbon. Examples of halogenated hydrocarbons include dichloromethane or dichloroethane. In some embodiments, the halogenated hydrocarbon is dichloromethane.

In some embodiments, the esterification reaction in step vii) is performed at a temperature of about 0° C. to about 60° C. In other embodiments, the esterification reaction in step vii) is performed at a temperature of about 10° C. to about 40° C. In still other embodiments, the esterification reaction in step vii) is performed at a temperature of about 20° C. to about 30° C.

Some embodiments further comprise comprising the step of:

viiia) reacting a compound of Formula 10, wherein $R^8$ is a —$C_{1-4}$ alkyl (e.g., tert-butyl), with a compound of Formula 11

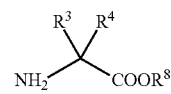

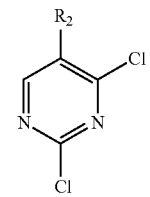

in the presence of an organic base and an organic solvent to generate a mixture comprising a compound of Formula 12 and a compound of Formula 13:

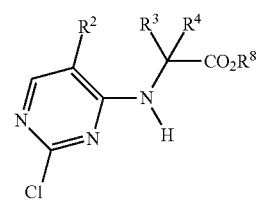

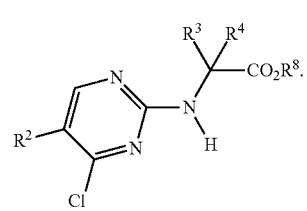

Some embodiments further comprise the steps of:

ixa) deprotecting the compound of Formula 12 and the compound of Formula 13 in the presence of an inorganic acid to generate a mixture comprising the compound of Formula 2 and a compound of Formula 14:

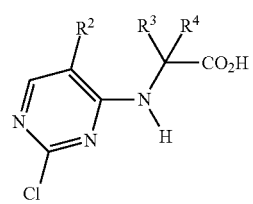

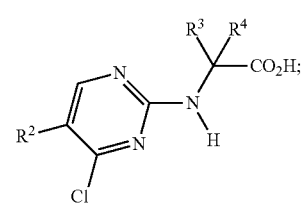

xa) reacting the mixture comprising the compound of Formula 2 and the compound of Formula 14 with HCl in the presence of an organic solvent to generate the hydrochloride salts of the compound of Formula 2 and the compound of Formula 14; and xia) recrystallizing the mixture of the hydrochloride salts of the compound of Formula 2 and the compound of Formula 14 to generate the hydrochloride salt of the compound of Formula 2.

Some alternative embodiments further comprise the steps of:

viiib) reacting a compound of Formula 11 with an acid salt of a compound of Formula 15 in the presence of a solvent and a base to generate the compound Formula 2

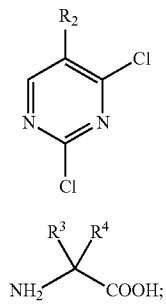

11 and ixb) reacting the compound of Formula 2 with an acid (e.g., HCl) to generate the acid (e.g., hydrochloride) salt of the compound of Formula 2.

In some embodiments, the base of step viiib) is an inorganic base selected from tripotassium phosphate, dipotassium hydrogen phosphate, dipotassium carbonate, disodium carbonate, trisodium phosphate, disodium hydrogen phosphate, or any combination thereof.

In some embodiments, the solvent of step viiib) comprises water.

In some embodiments, the solvent of step viiib) further comprises an alcohol selected from methanol, ethanol, propanol, iso-propanol, butanol, tert-butanol, or any combination thereof.

In some embodiments, the reaction of step viiib) is performed at a temperature of from about 70° C. to about 120° C. In some embodiments, the reaction of step viiib) is performed at a temperature of from about 80° C. to about 100° C.

The present invention also provides a process for preparing an HCl salt of a compound of Formula 2

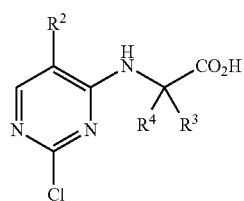

2 wherein $R^2$ is —H or —F;

$R^3$ is —$C_{1-4}$ aliphatic optionally substituted with 1-5 occurrences of $R^5$;

$R^4$ is —$C_{1-2}$ alkyl; or $R^3$ and $R^4$ are taken together to form a 3-7 membered carbocyclic or heterocyclic saturated ring optionally substituted with 1-5 occurrences of $R^5$;

each $R^5$ is independently selected from halogen, —$OCH_3$, —OH, —$NO_2$, —$NH_2$, —SH, —$SCH_3$, —$NHCH_3$, —CN or unsubstituted —$C_{1-2}$ aliphatic, or two $R^5$ groups, together with the carbon to which they are attached, form a cyclopropyl ring;

comprising:

viiia) reacting a compound of Formula 10, wherein $R^8$ is a alkyl (e.g., tert-butyl), with a compound of Formula 11

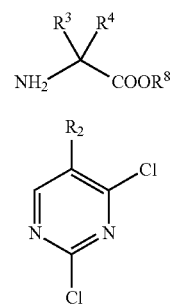

in the presence of an organic base and an organic solvent to generate a mixture comprising a compound of Formula 12 and a compound of Formula 13;

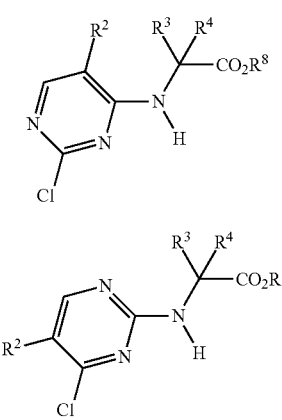

ixa) deprotecting the compound of Formula 12 and the compound of Formula 13 in the presence of an inorganic acid to generate a mixture comprising the compound of Formula 2 and a compound of Formula 14:

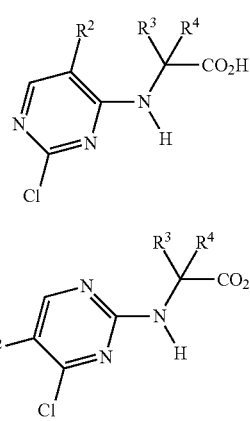

xa) reacting the mixture comprising the compound of Formula 2 and the compound of Formula 14 with HCl in the presence of an organic solvent to generate the hydrochloride salts of the compound of Formula 2 and the compound of Formula 14; and xia) recrystallizing the mixture of the hydrochloride salts of the compound of Formula 2 and the compound of Formula 14 to generate the hydrochloride salt of the compound of Formula 2.

The present invention also provides for a process for preparing an HCl salt of a compound of Formula 2

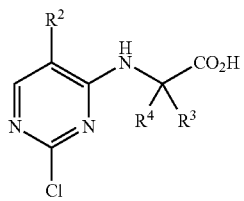

wherein
R² is —H or —F;
R³ is —C$_{1-4}$ aliphatic optionally substituted with 1-5 occurrences of R⁵;
R⁴ is —C$_{1-2}$ alkyl; or
R³ and R⁴ are taken together to form a 3-7 membered carbocyclic or heterocyclic saturated ring optionally substituted with 1-5 occurrences of R⁵;
each R⁵ is independently selected from halogen, —OCH₃, —OH, —NO₂, —NH₂, —SH, —SCH₃, —NHCH₃, —CN or unsubstituted —C$_{1-2}$ aliphatic, or
two R⁵ groups, together with the carbon to which they are attached, form a cyclopropyl ring;
comprising:
viiib) reacting a compound of Formula 11 with a compound of Formula 15 under coupling conditions to generate a compound of Formula 2:

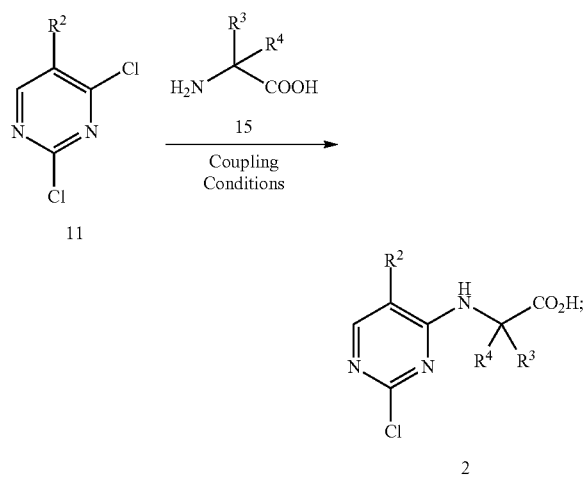

((R)-isomer if 15 is chiral)

and
ixb) reacting the compound of Formula 2 with HCl to generate the hydrochloride salt of the compound of Formula 2.

In some embodiments, the compound of Formula 11 reacts with the compound of Formula 15 under in the presence of a base and an organic solvent.

In other embodiments, the base comprises a carbonate of an alkali earth metal or a hydroxide of an alkali earth metal. For instance, the base comprises potassium carbonate.

In other embodiments, the solvent comprises an alcohol (e.g., methanol, ethanol, propanol, or any combination thereof).

In some embodiments, the HCl salt of the compound of Formula 2 is a compound of Formula 2a:

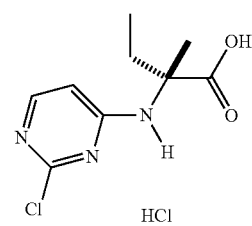

the compound of Formula 11 is 2,4-dichloropyrimidine (11a), and
the compound of Formula 15 is D-isovaline (15a).

In some embodiments, the HCl salt of the compound of Formula 2 is a compound of Formula 2b:

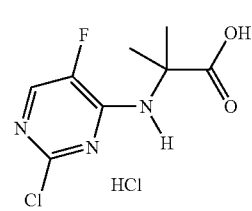

the compound of Formula 11 is 2,4-dichloro-5-fluoropyrimidine (11b), and the compound of Formula 15 is 2-amino-2-methylpropanoic acid (15b).

The present invention provides for a process for preparing a compound of Formula 2a:

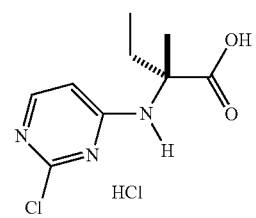

comprising the steps of:
xii) reacting a compound of Formula (16)

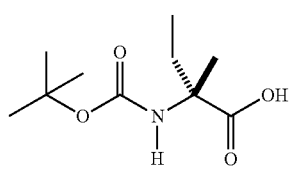

with 2,4-dichloropyrimidine (11a) in the presence of an inorganic acid and an organic solvent to generate a mixture comprising a compound of Formula (2a) and a compound of Formula (14a); and

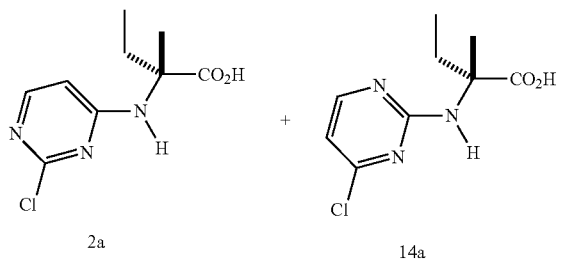

xiii) recrystallizing the mixture comprising the compound of Formula (2a) and the compound of Formula (14a) from an organic solvent to generate the compound of Formula (2a).

The present invention provides for a process for preparing a compound of Formula 2b:

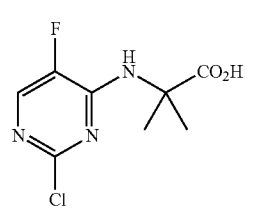

comprising the steps of:

xii) reacting a compound of Formula (17)

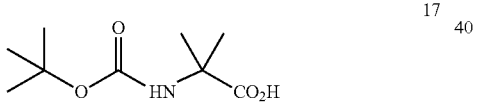

with 5-fluoro-2,4-dichloropyrimidine (11b) in the presence of an inorganic acid and an organic solvent to generate a compound of Formula (2b) and a compound of Formula (14b); and

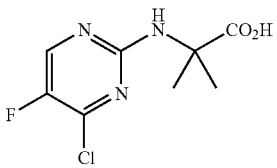

xiii) recrystallizing the mixture of the compound of Formula (2b) and the compound of Formula (14b) from an organic solvent to generate the compound of Formula (2b).

In some embodiments, the organic solvent in step xii) above is dioxane.

In some embodiments, the inorganic acid in step xii) is hydrochloric acid (HCl).

In some embodiments, the reaction in step xii) is performed for between about 6 to about 24 hours.

In some embodiments, the organic solvent in step xiii) is a mixture of ethyl acetate and isopropyl acetate.

In some embodiments, the compounds of Formula 2, Formula 2a and Formula 2b may also be another salt form instead of the HCl salt, including but not limited to an HBr salt or a sulfate salt.

In other embodiments, the compounds of Formula 2, Formula 2a, and Formula 2b may also be the free carboxylic acid form instead of a salt form.

The present invention provides for a process for preparing a compound of Formula 2a:

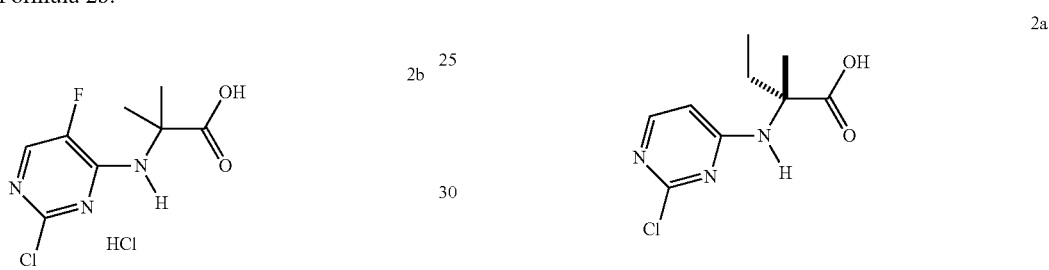

comprising:

reacting 2,4-dichloropyrimidine (11a) with D-isovaline (15a) under coupling conditions to generate the compound of Formula (2a).

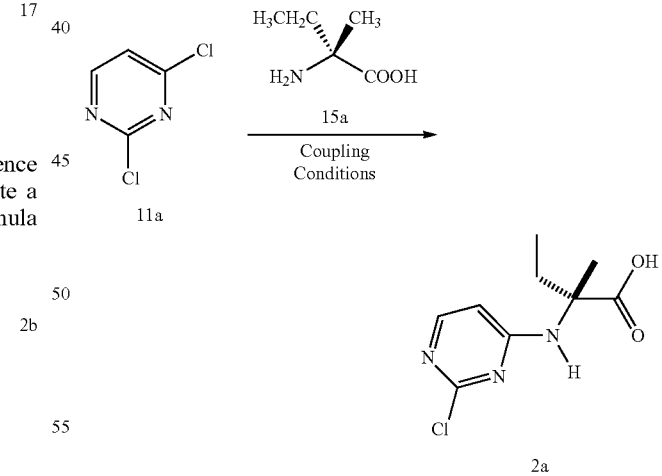

In some embodiments, the compound of Formula 11a reacts with the compound of Formula 15a under in the presence of a base and an organic solvent.

In other embodiments, the base comprises a carbonate of an alkali earth metal or a hydroxide of an alkali earth metal. For instance, the base comprises potassium carbonate.

In other embodiments, the solvent comprises an alcohol (e.g., methanol, ethanol, propanol, or any combination thereof).

The present invention provides for a process for preparing a compound of Formula 2b:

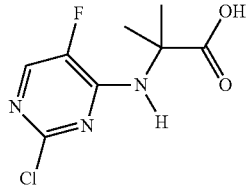
2b comprising:
reacting 2,4-dichloro-5-fluoropyrimidine (11b) with 2-amino-2-methylpropanoic acid (15b) under coupling conditions to the compound of Formula (2b).

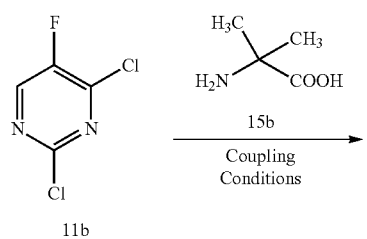

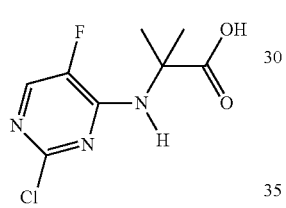
2b

In some embodiments, the compound of Formula 11b reacts with the compound of Formula 15b under in the presence of a base and an organic solvent.

In other embodiments, the base comprises a carbonate of an alkali earth metal or a hydroxide of an alkali earth metal. For instance, the base comprises potassium carbonate.

In other embodiments, the solvent comprises an alcohol (e.g., methanol, ethanol, propanol, or any combination thereof).

In some embodiments of the above processes, the compound of Formula I is:

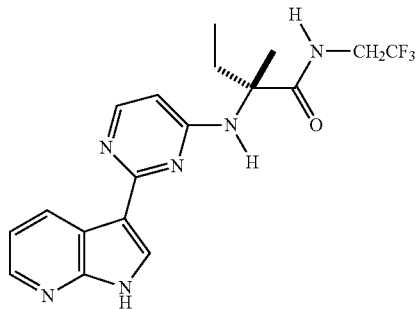
Ia (R)-2-(2-(1H-pyrrolo[2,3-b]pyridin-3-yl)pyrimidin-4-ylamino)-2-methyl-N-(2,2,2-trifluoroethyl)butanamide (Ia);

the compound of Formula 1 is:

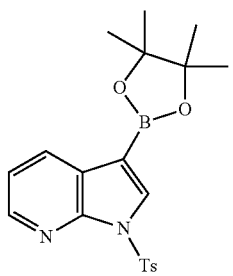
1a 3-(4,4,5,5-tetramethyl-1,3,2-dioxaborolan-2-yl)-1-tosyl-1H-pyrrolo[2,3-b]pyridine (1a);

the HCl salt of the compound of Formula 2 is:

2a (R)-2-(2-chloropyrimidin-4-ylamino)-2-methylbutanoic acid hydrochloride (2a);

the compound of Formula 3 is:

3a (R)-2-methyl-2-(2-(1-tosyl-1H-pyrrolo[2,3-b]pyridin-3-yl)pyrimidin-4-ylamino)butanoic acid (3a);

the compound of Formula 4 is:

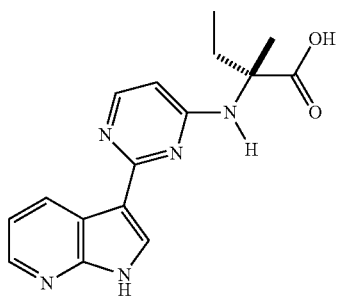
4a (R)-2-(2-(1H-pyrrolo[2,3-b]pyridin-3-yl)pyrimidin-4-ylamino)-2-methylbutanoic acid (4a); and HNR⁶R⁷ is 2,2,2-trifluoroethylamine (CF₃CH₂NH₂).

In some embodiments, the compound of Formula 11 is 2,4-dichloropyrimidine (11a) and the compound of Formula 15 is D-isovaline (15a).

In other embodiments of the above processes, Formula I is:

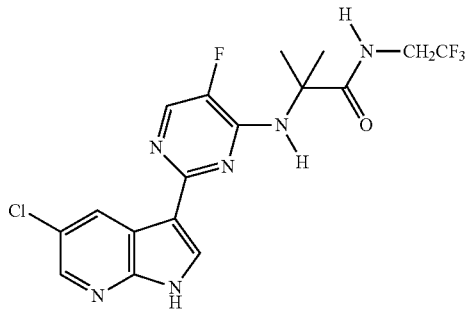

Ib 2-(2-(5-chloro-1H-pyrrolo[2,3-b]pyridin-3-yl)-5-fluoropyrimidin-4-ylamino)-2-methyl-N-(2,2,2-trifluoroethyl)propanamide (Ib);

the compound of Formula 1 is:

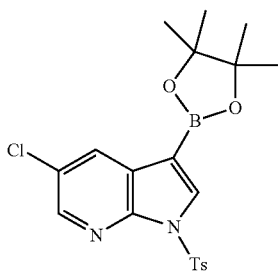

1b 5-chloro-3-(4,4,5,5-tetramethyl-1,3,2-dioxaborolan-2-yl)-1-tosyl-1H-pyrrolo[2,3-b]pyridine (1b);

the HCl salt of the compound of Formula 2 is:

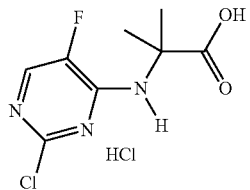

2b 2-(2-chloro-5-fluoropyrimidin-4-ylamino)-2-methylpropanoic acid hydrochloride (2b); the compound of Formula 3 is:

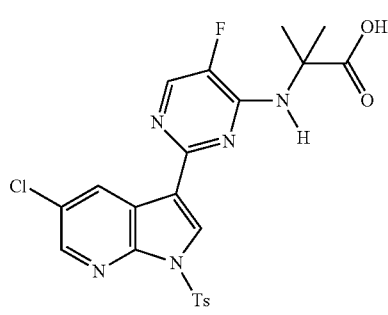

3b 2-(2-(5-chloro-1-tosyl-1H-pyrrolo[2,3-b]pyridin-3-yl)-5-fluoropyrimidin-4-ylamino)-2-methylpropanoic acid (3b);

the compound of Formula 4 is:

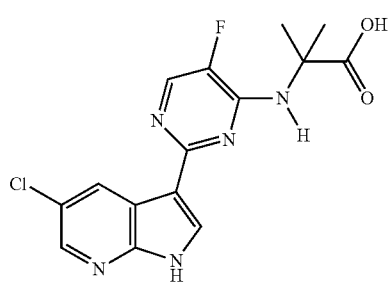

4b 2-(2-(5-chloro-1H-pyrrolo[2,3-b]pyridin-3-yl)-5-fluoropyrimidin-4-ylamino)-2-methylpropanoic acid (4b); and HNR⁶R⁷ is 2,2,2-trifluoroethylamine (CF₃CH₂NH₂).

In some embodiments, the compound of Formula 11 is 2,4-dichloro-5-fluoropyrimidine (11b) and the compound of Formula 15 is 2-amino-2-methylpropanoic acid (15b).

In some embodiments, this invention provides a process for producing a pharmaceutically acceptable salt of compounds of Formulae I, Ia or Ib, which further comprise the step of making a salt of a compound of Formulae I, Ia or Ib.

The present invention also provides a process for preparing a compound of Formula I:

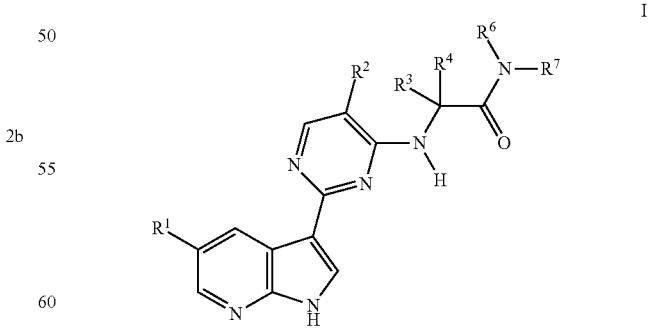

I wherein:
R¹ is —H, —Cl or —F;
R² is —H or —F;
R³ is —C₁₋₄ aliphatic optionally substituted with 1-5 occurrences of R⁵;

$R^4$ is —$C_{1-2}$ alkyl; or $R^3$ and $R^4$ are taken together to form a 3-7 membered carbocyclic or heterocyclic saturated ring optionally substituted with 1-5 occurrences of $R^5$;

each $R^5$ is independently selected from halogen, —$OCH_3$, —OH, —$NO_2$, —$NH_2$, —SH, —$SCH_3$, —$NHCH_3$, —CN, or unsubstituted —$C_{1-2}$ aliphatic, or two $R^5$ groups, together with the carbon to which they are attached, form a cyclopropyl ring;

$R^6$ is —H or unsubstituted —$C_{1-2}$ alkyl; and $R^7$ is a —$CH_2CR_3$ or —$(CH_2)_2CR_3$ wherein each R is independently —H or —F;

comprising the steps of:

iva) reacting a compound of Formula 5 with bromine ($Br_2$) in an organic solvent to generate a compound of Formula 6:

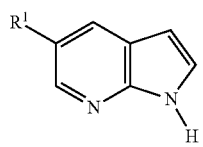

5

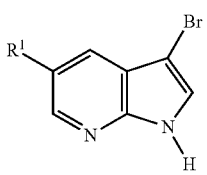

6 va) reacting a compound of Formula 6 in an organic solvent with p-toluenesulfonyl chloride to generate a compound of Formula 7:

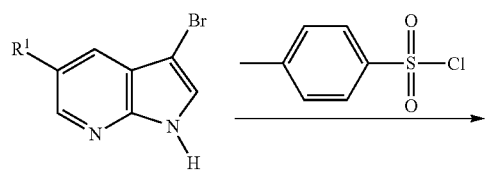

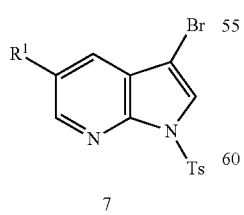

7 vi) reacting a compound of Formula 7 in an organic solvent with triisopropyl borate in the presence of a strong lithium base to generate a compound of Formula 8:

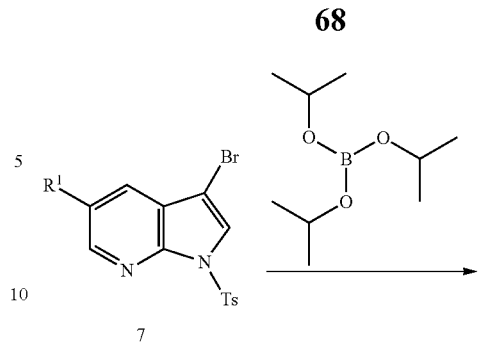

7

8 vii) esterifying the compound of Formula 8 with pinacolate alcohol in an organic solvent to generate a compound of Formula 1:

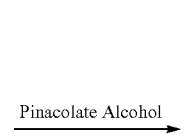

8

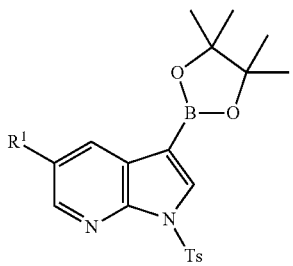

1 viiic) reacting a compound of Formula 10, wherein $R^8$ is $C_{1-4}$ alkyl, with an inorganic base to generate a salt of the compound of Formula 10:

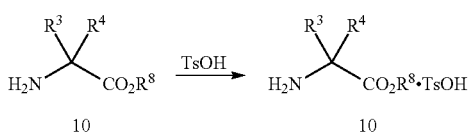

10                    10

((R)-isomer if 10 is chiral)

ixc) reacting the salt of the compound of Formula 10 with a compound of Formula 11 in the presence of an organic base and an organic solvent to generate a mixture of compounds of Formulae 12 and 13:

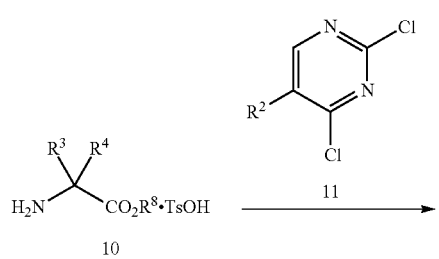
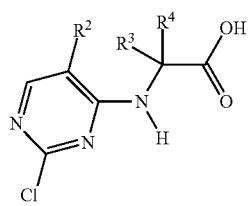

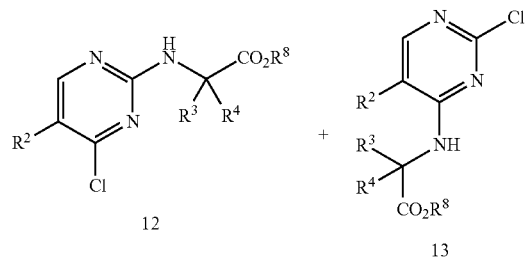

ixa) deprotecting the compound of Formula 12 and the compound of Formula 13 with an inorganic acid in an organic solvent to generate a mixture comprising compounds 2 and 14:

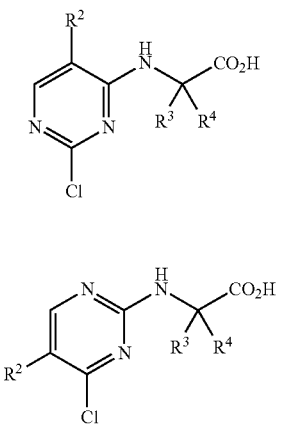

xia) recrystallizing the mixture of compounds comprising Formulae 2 and 14 from an organic solvent to generate a compound of Formula 2;

i) reacting the compound of Formula 1 and the hydrochloride salt of a compound of Formula 2

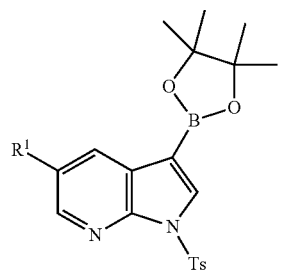

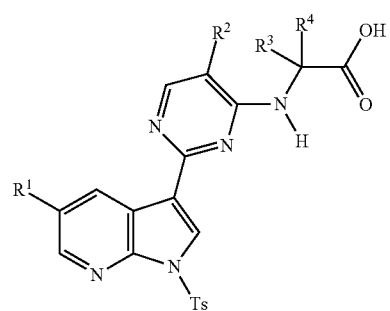

in the presence of water, an organic solvent, an inorganic base, and a transition metal catalyst to generate a compound of Formula 3,

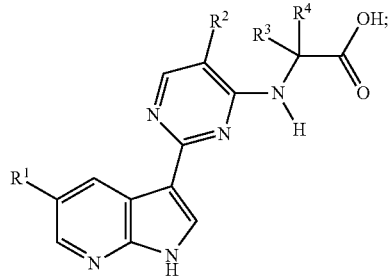

ii) deprotecting the compound of Formula 3 under basic conditions to generate a compound of Formula 4

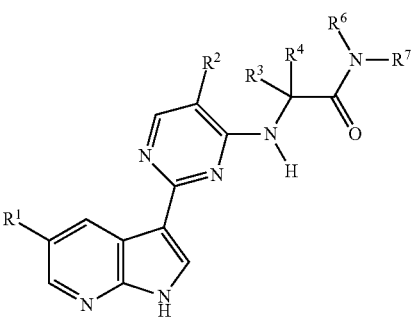

and iii) reacting the compound of Formula 4 with HNR⁶R⁷ in the presence of a coupling agent and an organic solvent to generate the compound of Formula I.

The present invention also provides a process for preparing a compound of Formula I:

wherein:
R¹ is —H, —Cl or —F;
R² is —H or —F;
R³ is —C$_{1-4}$ aliphatic optionally substituted with 1-5 occurrences of R⁵;
R⁴ is —C$_{1-2}$ alkyl; or
R³ and R⁴ are taken together to form a 3-7 membered carbocyclic or heterocyclic saturated ring optionally substituted with 1-5 occurrences of R⁵;
each R⁵ is independently selected from halogen, —OCH₃, —OH, —NO₂, —NH₂, —SH, —SCH₃, —NHCH₃, —CN, or unsubstituted —C$_{1-2}$ aliphatic, or
two R⁵ groups, together with the carbon to which they are attached, form a cyclopropyl ring;
R⁶ is —H or unsubstituted —C$_{1-2}$ alkyl; and
R⁷ is a —CH₂CR₃ or —(CH₂)₂CR₃ wherein each R is independently —H or —F;
comprising the steps of:
ivb) reacting a compound of Formula 5 with p-toluene-sulfonyl chloride in the presence of an organic solvent to generate a compound of Formula 9:

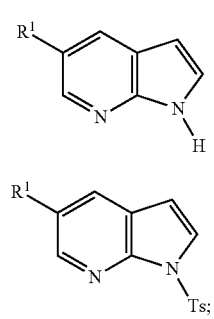

vb) reacting the compound of Formula 9 with N-bromo-succinimide to generate a compound of Formula 7:

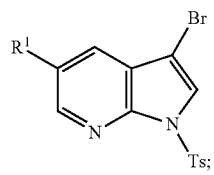

vi) reacting the compound of Formula 7 with triisopropyl borate, in the presence of an organic solvent and a strong lithium base to generate a compound of Formula 8:

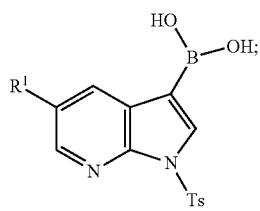

vii) esterifying the compound of Formula 8 with pinacolate alcohol in an organic solvent to generate a compound of Formula 1

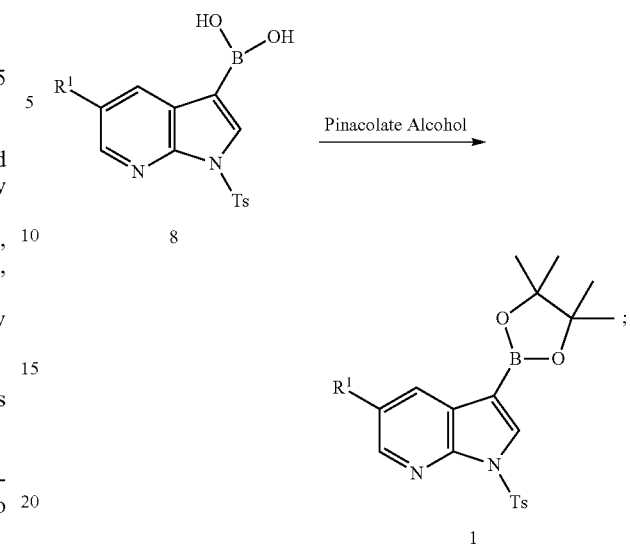

viiib) reacting a compound of Formula 11 with a compound of Formula 15 under coupling conditions to generate a compound of Formula 2:

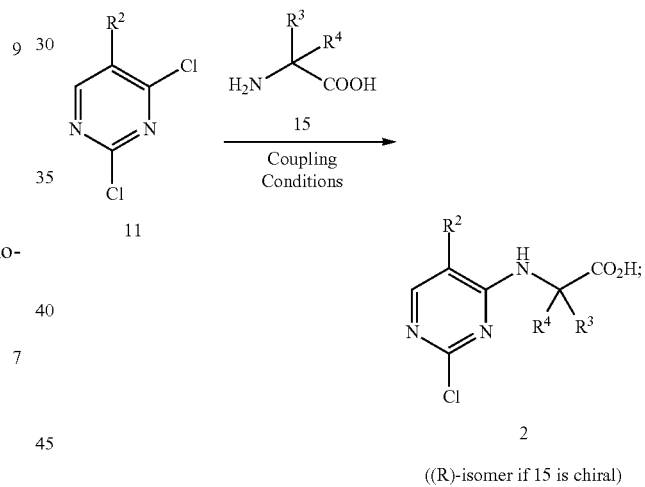

((R)-isomer if 15 is chiral)

ixb) reacting the compound of Formula 2 with HCl to generate the hydrochloride salt of the compound of Formula 2;
i) reacting the compound of Formula 1 and the HCl salt of the compound of Formula 2

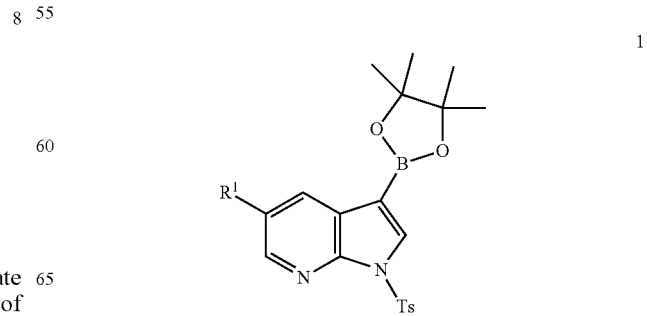

-continued

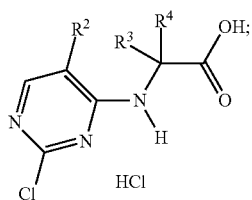
2 in the presence of water, an organic solvent, an inorganic base, and a transition metal catalyst to generate a compound of Formula 3,

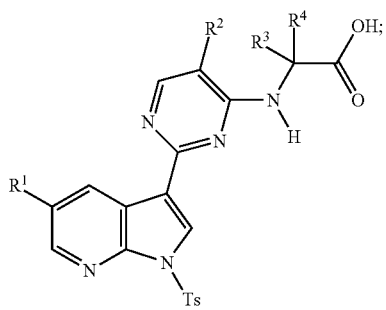
3 ii) deprotecting the compound of Formula 3 under basic conditions to generate a compound of Formula 4

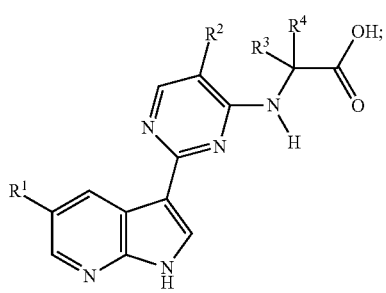
4 and
iii) reacting the compound of Formula 4 with $HNR^6R^7$ in the presence of a coupling agent and an organic solvent to generate the compound of Formula I.

In some embodiments, the organic solvent in step i) is an aprotic solvent.

In other embodiments, the aprotic solvent of step i) is acetonitrile, toluene, N,N-dimethylformamide, N,N-dimethylacetamide, acetone, or methyl tert-butyl ether.

In some embodiments, the organic solvent in step i) is a protic solvent.

In other embodiments, the protic solvent of step i) is ethanol, methanol, or isopropanol.

In some embodiments, the base in step i) is an inorganic base.

In other embodiments, the inorganic base of step i) is tripotassium phosphate, dipotassium hydrogen phosphate, dipotassium carbonate, disodium carbonate, trisodium phosphate, or disodium hydrogen phosphate.

In other embodiments, the inorganic base of step i) is an alkali metal hydroxide such as NaOH, KOH, or any combination thereof.

In some embodiments, the transition metal catalyst in step i) is a palladium-based catalyst.

In other embodiments, the palladium-based catalyst is palladium(II)acetate, tetrakis(triphenylphosphine)palladium(0) or tris(dibenzylideneacetone)dipalladium(0).

In still other embodiments, the palladium-based catalyst is palladium(II)acetate.

In some embodiments, the palladium catalyst is selected from

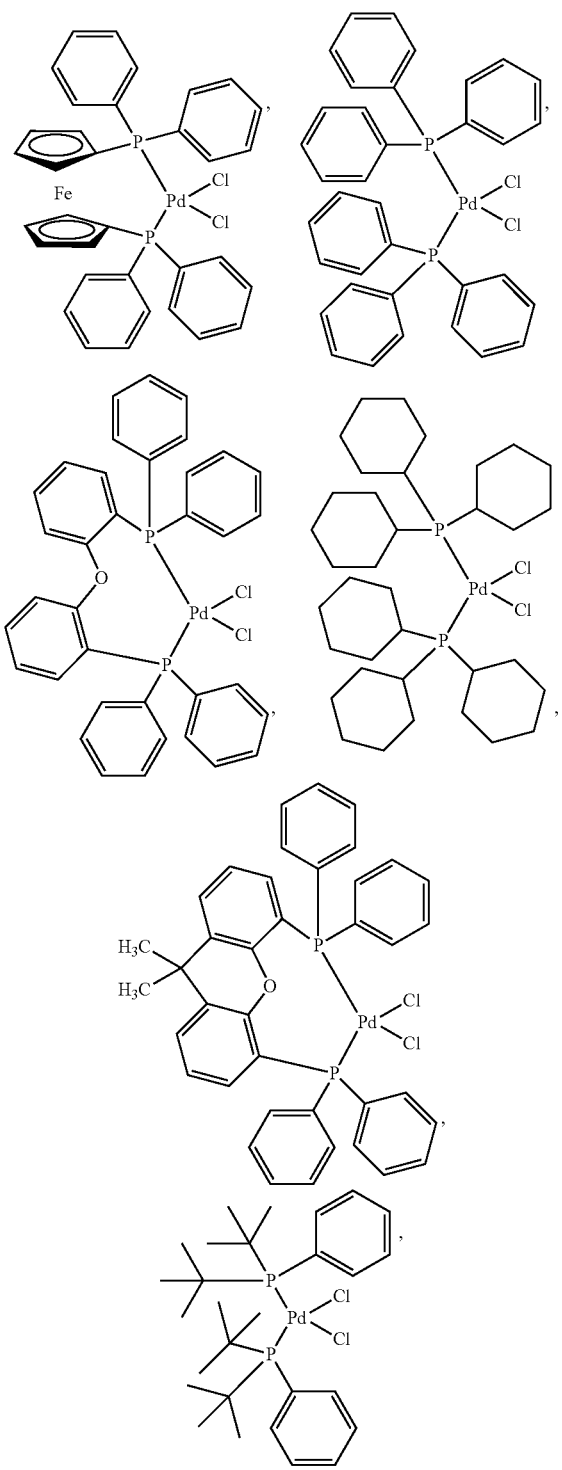

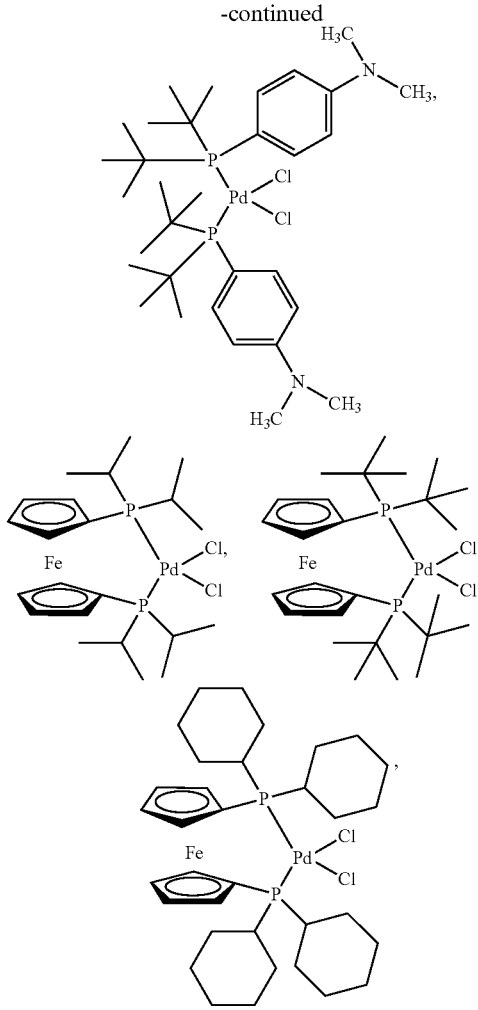

or any combination thereof.

In some embodiments, the reaction of step i) is performed in the presence of a phosphine ligand.

In further embodiments, the phosphine ligand is a triarylphosphine ligand or a trialkylphosphine ligand.

In still further embodiments, the triarylphosphine ligand is triphenylphosphine.

In some embodiments, the reaction of step i) is performed at a temperature between about 50° C. to about 110° C.

In other embodiments, the reaction of step i) is performed at a temperature between about 60° C. to about 95° C.

In still other embodiments, the reaction of step i) is performed at a temperature between about 70° C. to about 80° C.

In some embodiments, step i) is performed with agitation. For example, the reaction is performed in a vessel containing a stir bar that agitates the reaction mixture.

In some embodiments, the reaction of step i) occurs in about 17 hours.

In some embodiments, the reaction is about 86% complete in about 5 hours.

In other embodiments, the reaction is about 99% complete in about 17 hours.

The present invention provides a process for preparing (R)-2-(2-(1H-pyrrolo[2,3-b]pyridin-3-yl)pyrimidin-4-ylamino)-2-methyl-N-(2,2,2-trifluoroethyl)butanamide of Formula Ia:

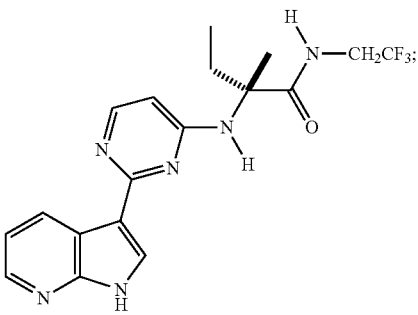

comprising the steps of:
iva) reacting 1H-pyrrolo[2,3-b]pyridine (5a) with bromine ($Br_2$) in the presence of an organic solvent to generate 3-bromo-1H-pyrrolo[2,3-b]pyridine (6a)

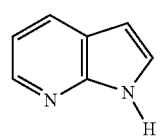

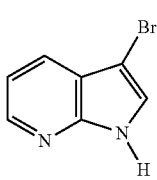

va) reacting 3-bromo-1H-pyrrolo[2,3-b]pyridine (6a) in an organic solvent with p-toluenesulfonyl chloride to generate 3-bromo-1-tosyl-1H-pyrrolo[2,3-b]pyridine (7a)

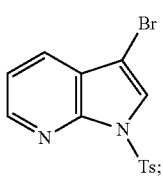

vi) reacting 3-bromo-1-tosyl-1H-pyrrolo[2,3-b]pyridine (7a) with triisopropyl borate in the presence of a strong lithium base in an organic solvent to generate 1-tosyl-1H-pyrrolo[2,3-b]pyridin-3-ylboronic acid (8a)

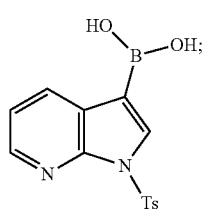

vii) esterifying 1-tosyl-1H-pyrrolo[2,3-b]pyridin-3-ylboronic acid (8a) with pinacolate alcohol in an organic solvent to generate 3-(4,4,5,5-tetramethyl-1,3,2-dioxaborolan-2-yl)-1-tosyl-1H-pyrrolo[2,3-b]pyridine (1a):

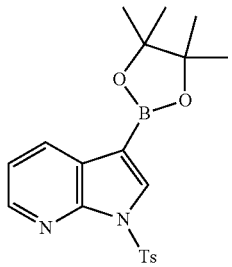

1a viiib) reacting 2,4-dichloropyrimidine (11a) with a hydrochloride salt of D-isovaline (15a) under coupling condition to generate a compound of Formula 2a

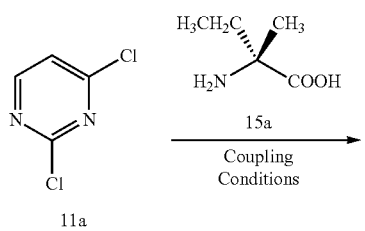

ixb) reacting the compound of Formula 2a with HCl to generate the hydrochloride salt of the compound of Formula 2a;

i) reacting the compound of Formula Ia with the compound of Formula 2a with in the presence of water, an organic solvent, an inorganic base, and a transition metal catalyst to generate a compound of Formula 3a,

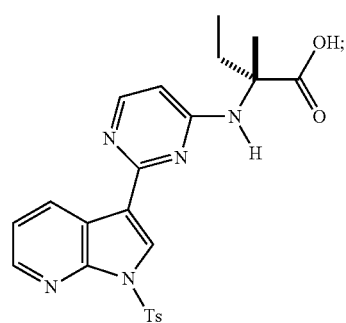

3a ii) deprotecting the compound of Formula 3a under basic conditions to generate a compound of Formula 4a

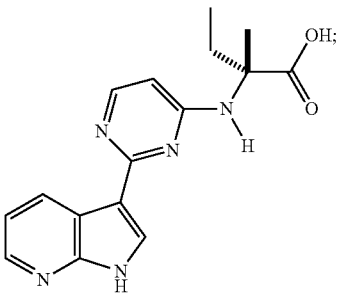

4a and iii) reacting the compound of Formula 4a with 2,2,2-trifluoroethylamine in the presence of a coupling agent and an organic solvent to generate the compound of Formula Ia.

The present invention provides a process for preparing (R)-2-(2-(1H-pyrrolo[2,3-b]pyridin-3-yl)pyrimidin-4-ylamino)-2-methyl-N-(2,2,2-trifluoroethyl)butanamide of Formula Ia:

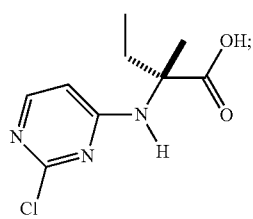

Ia comprising the steps of:

ivb) reacting 1H-pyrrolo[2,3-b]pyridine (5a) with p-toluenesulfonyl chloride in the presence of an organic solvent to generate 1-tosyl-1H-pyrrolo[2,3-b]pyridine (9a)

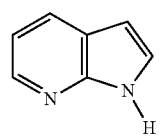

5a

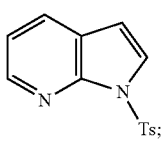

9a vb) reacting 1-tosyl-1H-pyrrolo[2,3-b]pyridine (9a) in an organic solvent with N-bromosuccinimide to generate 3-bromo-1-tosyl-1H-pyrrolo[2,3-b]pyridine (7a)

vi) reacting 3-bromo-1-tosyl-1H-pyrrolo[2,3-b]pyridine (7a) with triisopropyl borate in the presence of a strong lithium base in an organic solvent to generate 1-tosyl-1H-pyrrolo[2,3-b]pyridin-3-ylboronic acid (8a)

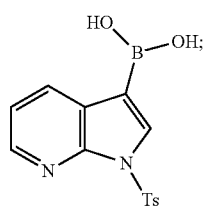

vii) esterifying 1-tosyl-1H-pyrrolo[2,3-b]pyridin-3-ylboronic acid (8a) with pinacolate alcohol in an organic solvent to generate 3-(4,4,5,5-tetramethyl-1,3,2-dioxaborolan-2-yl)-1-tosyl-1H-pyrrolo[2,3-b]pyridine (1a):

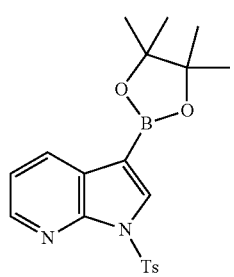

viiib) reacting 2,4-dichloropyrimidine (11a) with a hydrochloride salt of D-isovaline (15a) under coupling condition to generate a compound of Formula 2a

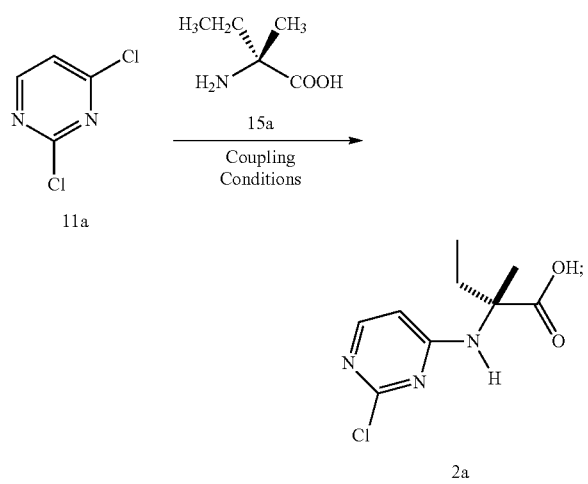

ixb) reacting the compound of Formula 2a with HCl to generate the hydrochloride salt of the compound of Formula 2a;

i) reacting the compound of Formula Ia with the compound of Formula 2a with in the presence of water, an organic solvent, an inorganic base, and a transition metal catalyst to generate a compound of Formula 3a,

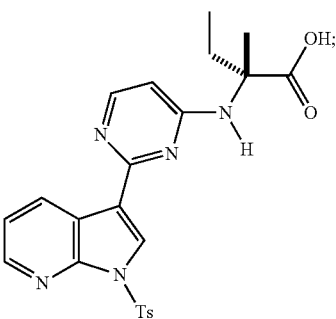

ii) deprotecting the compound of Formula 3a under basic conditions to generate a compound of Formula 4a

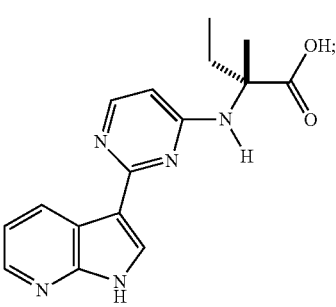

and iii) reacting the compound of Formula 4a with 2,2,2-trifluoroethylamine in the presence of a coupling agent and an organic solvent to generate the compound of Formula Ia.

The present invention provides a process for preparing (2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib:

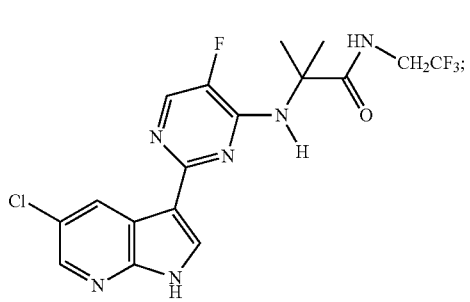

comprising the steps of:

iva) reacting 5-chloro-1H-pyrrolo[2,3-b]pyridine (5b) with bromine (Br$_2$) in an organic solvent to generate 5-chloro-3-bromo-1H-pyrrolo[2,3-b]pyridine (6b)

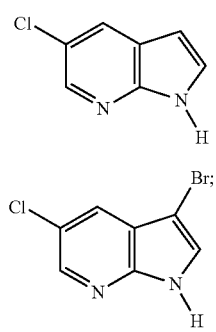

5b

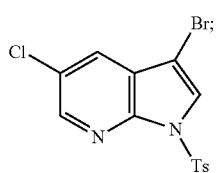

6b va) reacting 5-chloro-3-bromo-1H-pyrrolo[2,3-b]pyridine (6b) in an organic solvent with p-toluenesulfonyl chloride to generate 5-chloro-3-bromo-1-tosyl-1H-pyrrolo[2,3-b]pyridine (7b)

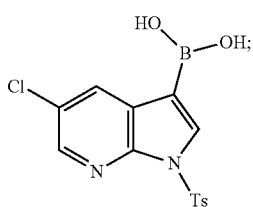

7b vi) reacting 5-chloro-3-bromo-1-tosyl-1H-pyrrolo[2,3-b]pyridine (7b) with triisopropyl borate in the presence of a strong lithium base in an organic solvent to generate 5-chloro-1-tosyl-1H-pyrrolo[2,3-b]pyridin-3-ylboronic acid (8b)

8b

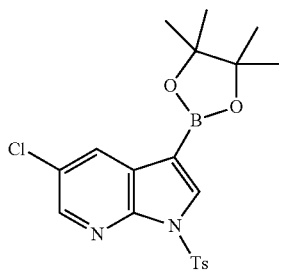

vii) esterifying 1-tosyl-1H-pyrrolo[2,3-b]pyridin-3-ylboronic acid (8b) with pinacolate alcohol in an organic solvent to generate 5-chloro-3-(4,4,5,5-tetramethyl-1,3,2-dioxaborolan-2-yl)-1-tosyl-1H-pyrrolo[2,3-b]pyridine (1b):

1b viiib) reacting 2,4-dichloro-5-fluoropyrimidine (11b) with 2-amino-2-methylpropanoic acid (15b) under coupling condition to generate (2b)

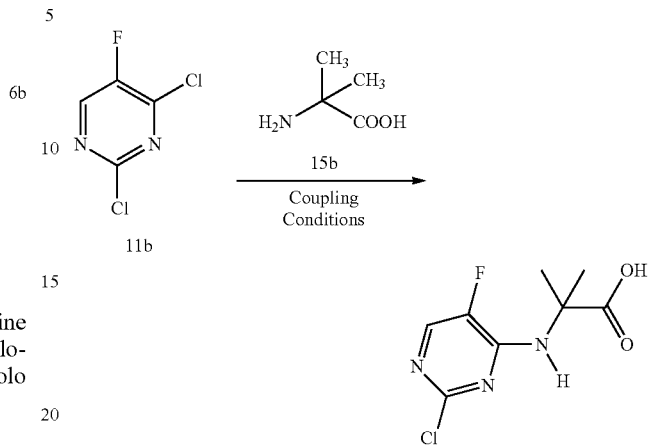

2b ixb) reacting the compound of Formula 2b with HCl to generate the hydrochloride salt of the compound of Formula 2b;

i) reacting the compound of Formula (2b) with the compound of Formula (Ib) in the presence of water, an organic solvent, an inorganic base, and a transition metal catalyst to generate a compound of Formula 3b,

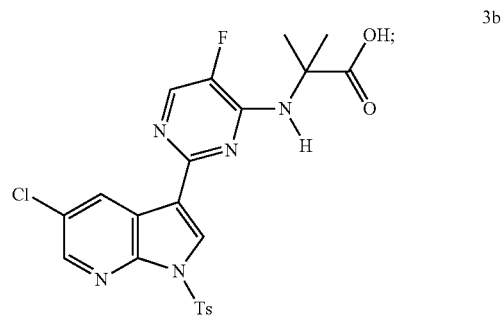 [SMILES: Cc1ccc(S(=O)(=O)n2cc(-c3ncc(F)c(NC(C)(C)C(=O)O)n3)c3cc(Cl)cnc32)cc1]

3b ii) deprotecting the compound of Formula 3b under basic conditions to generate a compound of Formula 4b

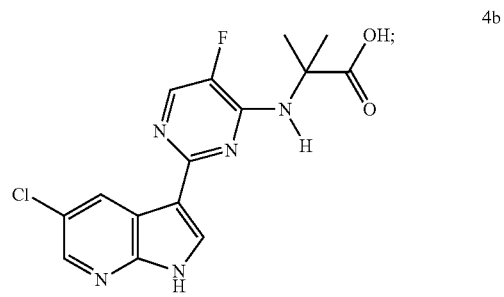 [SMILES: CC(C)(Nc1nc(-c2c[nH]c3ncc(Cl)cc23)ncc1F)C(=O)O]

4b and iii) reacting the compound of Formula 4b with $CF_3(CH_2)NH_2$, in the presence of a coupling agent and an organic solvent to generate the compound of Formula Ib.

The present invention provides a process for preparing (2-(2-(5-chloro-1H-pyrrolo[2,3-b]pyridin-3-yl)-5-fluoropyrimidin-4-ylamino)-2-methyl-N-(2,2,2-trifluoroethyl)propanamide of Formula Ib:

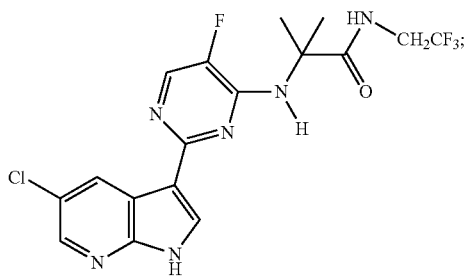

comprising the steps of:

ivb) reacting 5-chloro-1H-pyrrolo[2,3-b]pyridine (5b) with p-toluenesulfonyl chloride in an organic solvent to generate 5-chloro-1-tosyl-1H-pyrrolo[2,3-b]pyridine (9b)

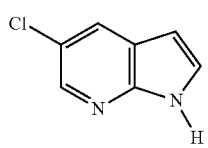

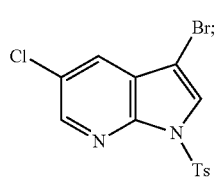

vb) reacting 5-chloro-1-tosyl-1H-pyrrolo[2,3-b]pyridine (9b) in an organic solvent with N-bromosuccinimide to generate 5-chloro-3-bromo-1-tosyl-1H-pyrrolo[2,3-b]pyridine (7b)

vi) reacting 5-chloro-3-bromo-1-tosyl-1H-pyrrolo[2,3-b]pyridine (7b) with triisopropyl borate in the presence of a strong lithium base in an organic solvent to generate 5-chloro-1-tosyl-1H-pyrrolo[2,3-b]pyridin-3-ylboronic acid (8b)

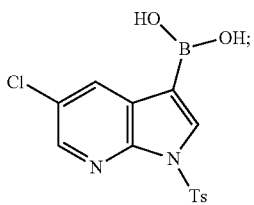

vii) esterifying 1-tosyl-1H-pyrrolo[2,3-b]pyridin-3-ylboronic acid (8b) with pinacolate alcohol in an organic solvent to generate 5-chloro-3-(4,4,5,5-tetramethyl-1,3,2-dioxaborolan-2-yl)-1-tosyl-1H-pyrrolo[2,3-b]pyridine (1b):

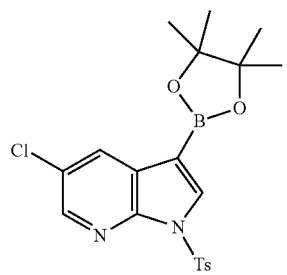

viiib) reacting 2,4-dichloro-5-fluoropyrimidine (11b) with 2-amino-2-methylpropanoic acid (15b) under coupling condition to generate (2b)

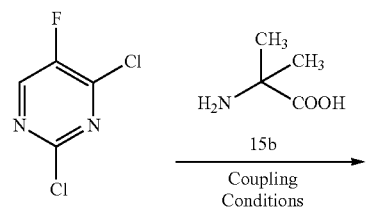

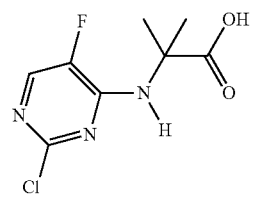

ixb) reacting the compound of Formula 2b with HCl to generate the hydrochloride salt of the compound of Formula 2b;

i) reacting the compound of Formula (2b) with the compound of Formula (Ib) in the presence of water, an organic solvent, an inorganic base, and a transition metal catalyst to generate a compound of Formula 3b, Formula 1 is:

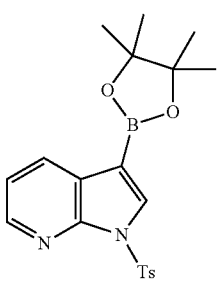

3-(4,4,5,5-tetramethyl-1,3,2-dioxaborolan-2-yl)-1-tosyl-1H-pyrrolo[2,3-b]pyridine (1a);
the HCl salt of Formula 2 is:

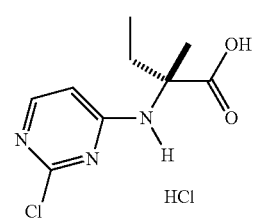

(R)-2-(2-chloropyrimidin-4-ylamino)-2-methylbutanoic acid hydrochloride (2a);
Formula 3 is:

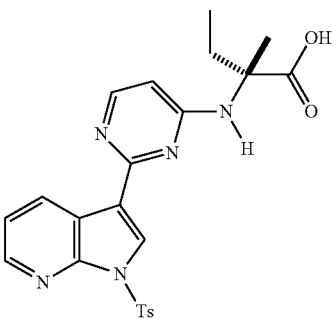

(R)-2-methyl-2-(2-(1-tosyl-1H-pyrrolo[2,3-b]pyridin-3-yl)pyrimidin-4-ylamino)butanoic acid (3a);
Formula 4 is:

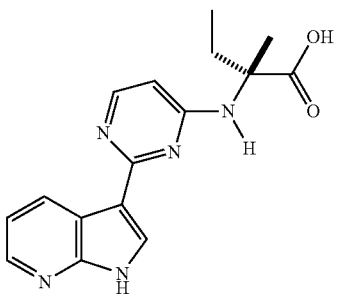

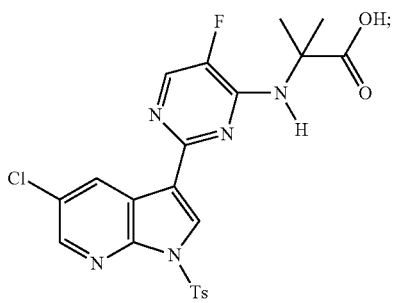

ii) deprotecting the compound of Formula 3b under basic conditions to generate a compound of Formula 4b

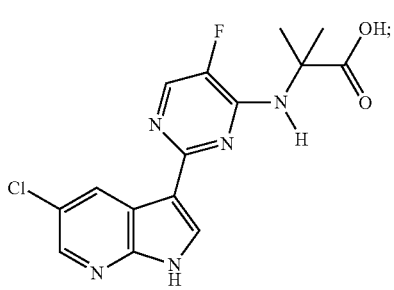

and iii) reacting the compound of Formula 4b with CF$_3$(CH$_2$)NH$_2$, in the presence of a coupling agent and an organic solvent to generate the compound of Formula Ib.

In some embodiments of the above processes, the compound of Formula I is:

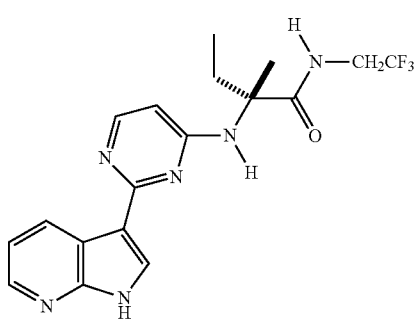

(R)-2-(2-(1H-pyrrolo[2,3-b]pyridin-3-yl)pyrimidin-4-ylamino)-2-methyl-N-(2,2,2-trifluoroethyl)butanamide (Ia);

(R)-2-(2-(1H-pyrrolo[2,3-b]pyridin-3-yl)pyrimidin-4-ylamino)-2-methylbutanoic acid (4a); and $HNR^6R^7$ is 2,2,2-trifluoroethylamine ($CF_3CH_2NH_2$).

In other embodiments of the above processes, the compound of Formula I is:

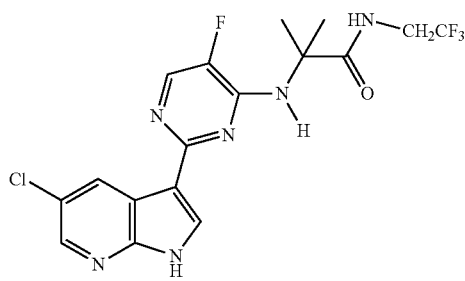

Ib 2-(2-(5-chloro-1H-pyrrolo[2,3-b]pyridin-3-yl)-5-fluoropyrimidin-4-ylamino)-2-methyl-N-(2,2,2-trifluoroethyl)propanamide (Ib);

Formula 1 is:

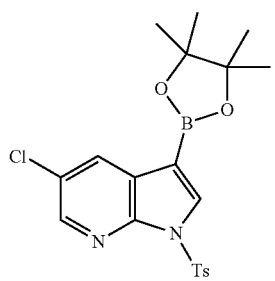

1b 5-chloro-3-(4,4,5,5-tetramethyl-1,3,2-dioxaborolan-2-yl)-1-tosyl-1H-pyrrolo[2,3-b]pyridine (1b);

the HCl salt of Formula 2 is:

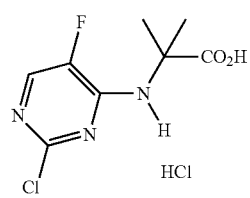

2b 2-(2-chloro-5-fluoropyrimidin-4-ylamino)-2-methylpropanoic acid hydrochloride (2b);

Formula 3 is:

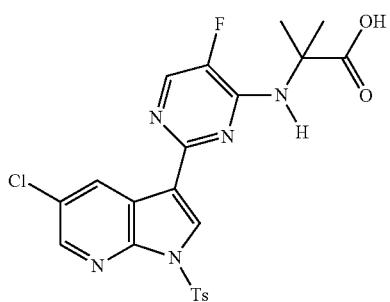

3b 2-(2-(5-chloro-1-tosyl-1H-pyrrolo[2,3-b]pyridin-3-yl)-5-fluoropyrimidin-4-ylamino)-2-methylpropanoic acid (3b);

Formula 4 is:

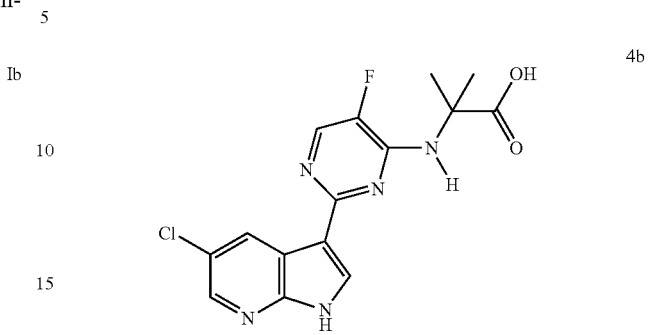

4b 2-(2-(5-chloro-1H-pyrrolo[2,3-b]pyridin-3-yl)-5-fluoropyrimidin-4-ylamino)-2-methylpropanoic acid (4b); and $HNR^6R^7$ is 2,2,2-trifluoroethylamine ($CF_3CH_2NH_2$).

In some embodiments, the organic solvent in step i) is an aprotic solvent.

In other embodiments, the aprotic solvent is acetonitrile, toluene, N,N-dimethylformamide, N,N-dimethylacetamide, acetone, or methyl tert-butyl ether.

In still other embodiments, the aprotic solvent is acetonitrile.

In some embodiments, the organic solvent in step i) is a protic solvent.

In other embodiments, the protic solvent is ethanol, methanol, or isopropanol.

In still other embodiments, the protic solvent is ethanol or isopropanol.

In some embodiments, the base in step i) is an inorganic base.

In other embodiments, the inorganic base is tripotassium phosphate, dipotassium hydrogen phosphate, dipotassium carbonate, disodium carbonate, trisodium phosphate, or disodium hydrogen phosphate.

In still other embodiments, the inorganic base is tripotassium phosphate, dipotassium hydrogen phosphate, trisodium phosphate, or disodium hydrogen phosphate.

In further embodiments, the inorganic base is tripotassium phosphate.

In some embodiments, the transition metal catalyst in step i) is a palladium-based catalyst.

In other embodiments, the palladium-based catalyst is palladium(II)acetate, tetrakis(triphenylphosphine)palladium(0) or tris(dibenzylideneacetone)dipalladium(0).

In still other embodiments, the palladium-based catalyst is palladium(II)acetate.

In some embodiments, the palladium catalyst is selected from

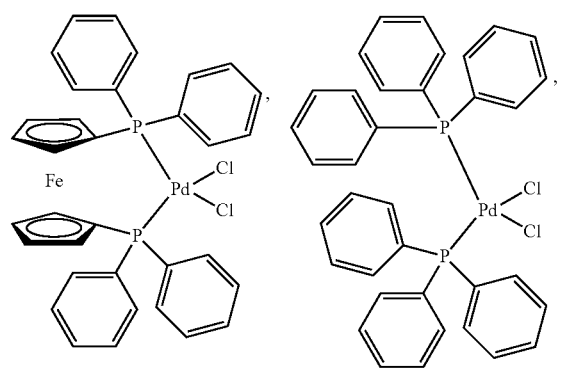
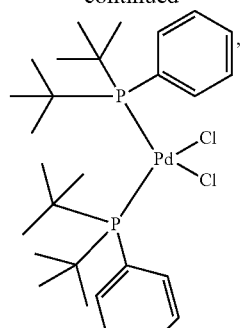
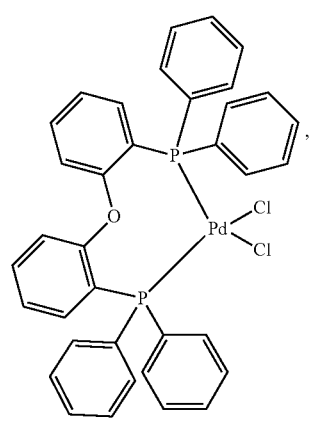
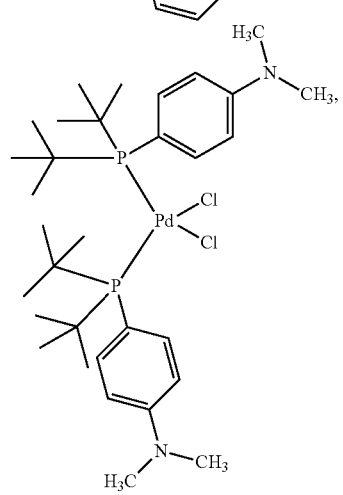
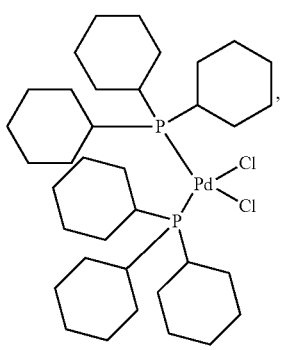
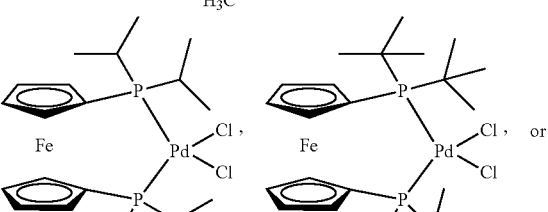
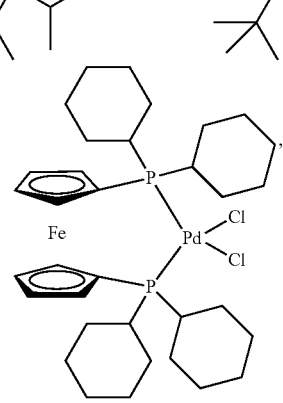
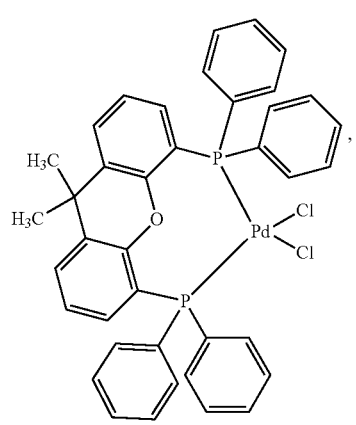

or any combination thereof.

In some embodiments, the reaction of step i) is performed in the presence of a phosphine ligand.

In other embodiments, the phosphine ligand is a triarylphosphine ligand or a trialkylphosphine ligand.

In still other embodiments, the phosphine ligand triarylphosphine ligand is triphenylphosphine.

In some embodiments, the reaction of step i) is performed at between about 50° C. to about 110° C.

In other embodiments, the reaction of step i) is performed at between about 60° C. to about 95° C.

In still other embodiments, the reaction of step i) is performed at between about 70° C. to about 80° C.

In some embodiments, step i) is carried out with agitation.

In some embodiments, the reaction of step i) occurs in about 17 hours.

In some embodiments, the reaction is about 86% complete in about 5 hours.

In other embodiments, the reaction is about 99% complete in about 17 hours.

In some embodiments, an alkali-metal hydroxide base is present in step iii).

In other embodiments, the alkali-metal hydroxide base is selected from sodium hydroxide or potassium hydroxide.

In still other embodiments, the alkali-metal hydroxide base is potassium hydroxide.

In some embodiments, the alkali-metal hydroxide base is about 2N to about 4N.

In other embodiments, the alkali-metal hydroxide base is about 4N.

In some embodiments, the concentration of potassium hydroxide is about 2N to about 4N.

In other embodiments, the concentration of potassium hydroxide is about 4N.

In some embodiments, the deprotection reaction in step iii) is performed at between about 60° C. to about 110° C. In other embodiments, the deprotection reaction is performed between about 65° C. to about 95° C.

In still other embodiments, the deprotection reaction is performed between about 70° C. to about 80° C.

In still other embodiments, the coupling agent of step iii) is propylphosphonic anhydride.

In some embodiments, the organic solvent of step iii) is a halogenated hydrocarbon or alkyl-substituted THF (e.g., 2-MeTHF).

In other embodiments, the halogenated hydrocarbon is dichloromethane or dichloroethane.

In some embodiments, step i) includes an additional step of adding catalyst and compound of Formula 1 after the reaction has run for about 5 hours.

In some embodiments, step i) includes an additional step of adding catalyst and compound of Formula 1 after the coupling reaction is about 86% complete.

In some embodiments, the compounds of Formula 2, Formula 2a and Formula 2b may also be another salt form instead of the HCl salt, including but not limited to an HBr salt or a sulfate salt.

In other embodiments, the compounds of Formula 2, Formula 2a and Formula 2b may also be the free carboxylic acid form instead of a salt form.

In other embodiments, in a compound of any Formulae I, 2, 3 or 4, $R^3$ and $R^4$ are taken together to form a ring selected from:

wherein one or more carbon atoms in said ring are optionally and independently replaced by N, O or S.

In another embodiment, in a compound of any Formulae I, 2, 3, or 4, $R^3$ and $R^4$ are:

In a further embodiment, $R^3$ and $R^4$ are:

In yet a further embodiment, $R^3$ and $R^4$ are:

In still a further embodiment, $R^3$ and $R^4$ are:

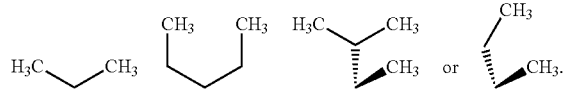

III. Processes and Intermediates

The following definitions describe terms and abbreviations used herein:
Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
MeOH methanol
MTBE methyl tert-butyl ether
DMF N,N-dimethylformamide
DMA N,N-dimethylacetamide
DMSO dimethyl sulfoxide
HOAc acetic acid
TFA trifluoroacetic acid
$Et_3N$ triethylamine
DIPEA diisopropylethylamine
DIEA diisopropylethylamine
$K_2CO_3$ dipotassium carbonate
$Na_2CO_3$ disodium carbonate
NaOH sodium hydroxide
$K_3PO_4$ tripotassium phosphate
HPLC high performance liquid chromatography
Hr or h hours
atm atmospheres
rt or RT room temperature
HCl hydrochloric acid
HBr hydrobromic acid
$H_2O$ water
NaOAc sodium acetate
$H_2SO_4$ sulfuric acid
$N_2$ nitrogen gas
$H_2$ hydrogen gas
$Br_2$ bromine
n-BuLi n-butyl lithium
$Pd(OAc)_2$ palladium(II)acetate
$PPh_3$ triphenylphosphine
rpm revolutions per minute
Equiv. equivalents
Ts tosyl
IPA isopropyl alcohol As used herein, other abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

In one embodiment, the invention provides a process and intermediates for preparing a compound of Formula I as outlined in Scheme I.

Scheme I:

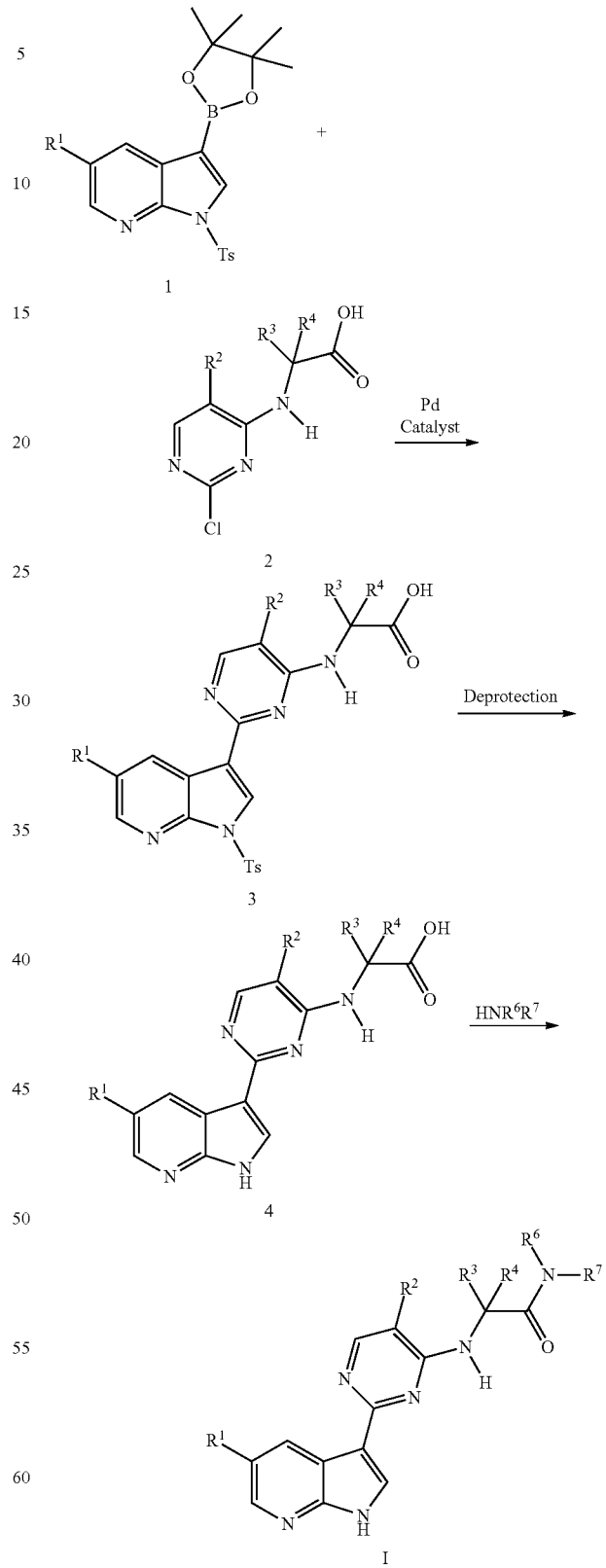

In Scheme I, a compound of Formula 1 is coupled with a compound of Formula 2 via a palladium catalyzed cross coupling reaction to generate a compound of Formula 3. The compound of Formula 3 is deprotected (e.g., via treatment with a base) to generate a compound of Formula 4. The compound of Formula 4 is then coupled with an amine having the formula HNR⁶R⁷ in the presence of a coupling reagent to generate the compound of Formula I, wherein $R^1$, $R^2$, $R^3$, $R^4$, $R^6$, and $R^7$, are defined herein.

Scheme Ia:

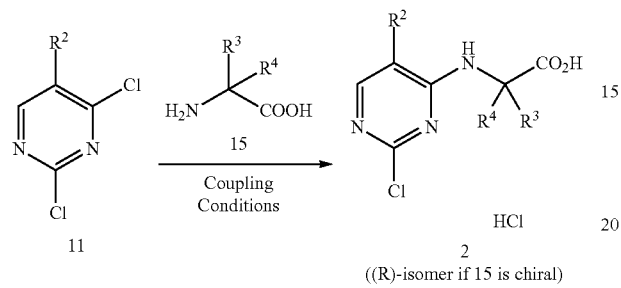

In Scheme 1a, a compound of Formula 11 is reacted with a compound of Formula 15 under coupling conditions to generate the HCl salt of the compound of Formula 2. In Scheme 1a, radicals $R^2$, $R^3$, and $R^4$ are as defined herein.

Scheme Ib:

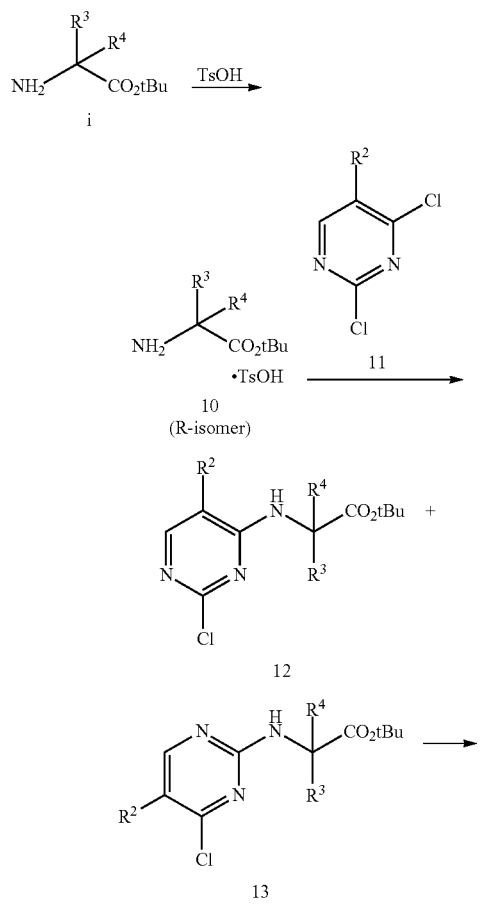

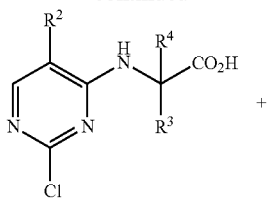

In Scheme 1b, a tosylate salt of a compound of Formula 10 is prepared by mixing a compound of Formula i in an organic solvent (e.g., ethyl acetate) with a solution of an inorganic base (e.g., an alkali metal base such as but not limited to NaOH). Preparation of a mixture of a compound of Formula 12 and a compound of Formula 13 is achieved by reacting a compound of Formula 10 with an organic base (e.g., diisopropylethylamine (DIEA)) in an organic solvent (e.g., isopropyl alcohol) at a suitable temperature (e.g., between about 80° C. and about 110° C.) for a suitable time period (e.g., for between about 30 and about 80 hours). An HCl salt of a compound of Formula 2 and a compound of Formula 14 are prepared by adding an inorganic acid (e.g., HCl) to a mixture of the compound of Formula 12 and the compound of Formula 13, adjusting the pH of the solution to a suitable value (e.g., 3), then adding additional inorganic acid (e.g., HCl) in an organic solvent (e.g., ethyl acetate). The compound of Formula 2 is purified by recrystallization of the mixture of the compound of Formula 2 and the compound of Formula 14 from an organic solvent (e.g., a mixture of ethyl acetate and isopropyl alcohol). In Scheme 1b, radicals $R^2$, $R^3$, and $R^4$ are as defined herein.

Scheme Ic:

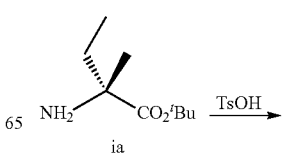

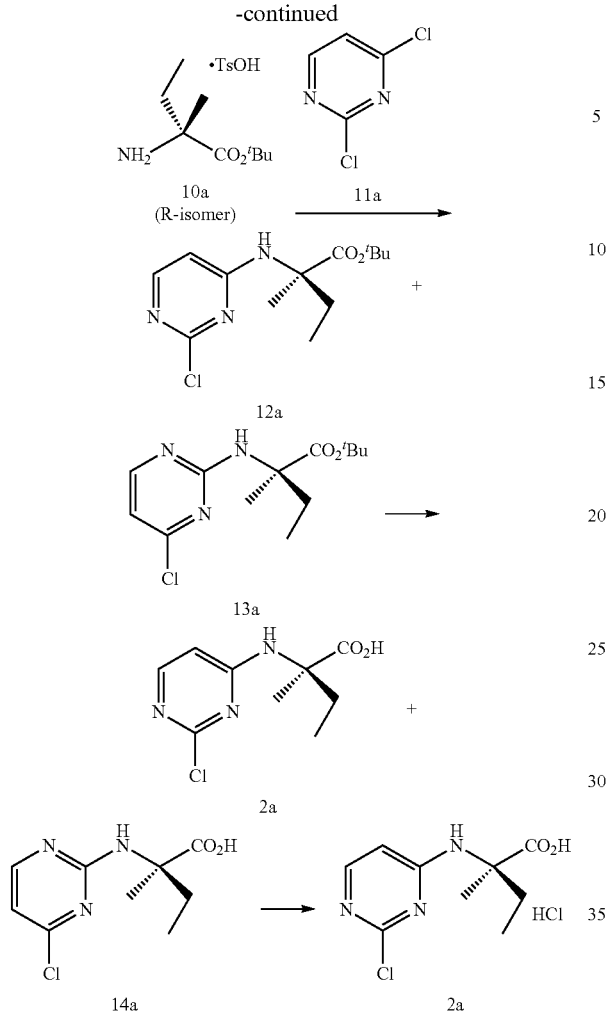

In another embodiment, the invention provides a process and intermediates to prepare a compound of Formula 1 as outlined below in Scheme II.

Scheme IIb:

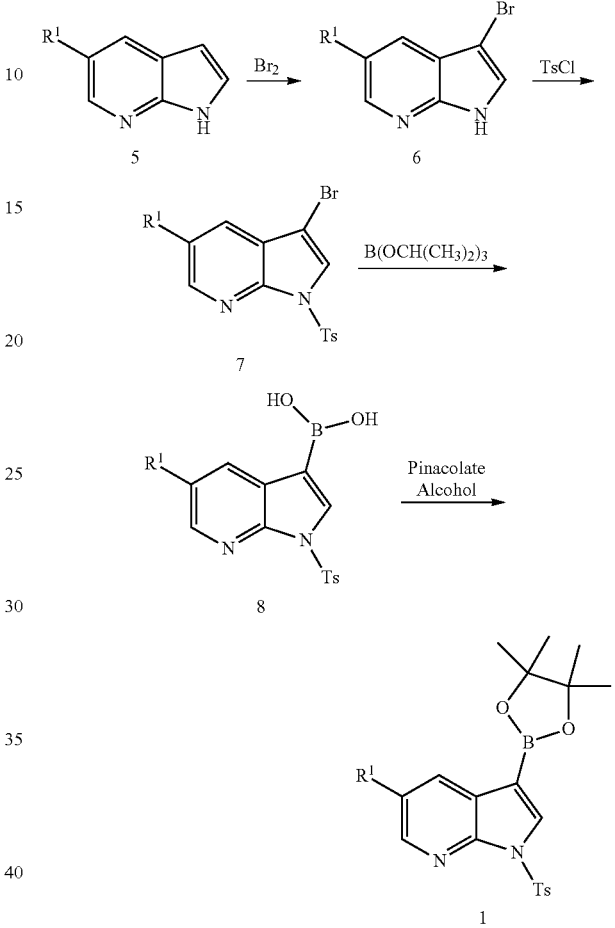

In Scheme Ic, a compound of Formula 10a is prepared by mixing a compound of Formula is (Nagase &Company, Ltd., made according to the process outlined in US2007/161624) in an organic solvent (e.g., ethyl acetate) with a solution of an inorganic base (e.g., an alkali metal base such as NaOH). Preparation of a mixture of (R)-tert-butyl 2-(2-chloropyrimidin-4-ylamino)-2-methylbutanoate (12a) and (R)-tert-butyl 2-(4-chloropyrimidin-2-ylamino)-2-methylbutanoate (13a) is achieved by reacting a compound of Formula 10a with a compound of Formula 11a in the presence of an organic base (e.g., diisopropylethylamine (DIEA)) in an organic solvent (e.g., isopropyl alcohol) at a suitable temperature (e.g., about 95° C.) for a suitable time period (e.g., for about 40 hours). (R)-2-(2-chloropyrimidin-4-ylamino)-2-methylbutanoic acid (2a) and (R)-2-(4-chloropyrimidin-2-ylamino)-2-methylbutanoic acid (14a) are prepared by adding inorganic acid (e.g., HCl) to a mixture of (R)-tert-butyl 2-(2-chloropyrimidin-4-ylamino)-2-methylbutanoate (12a) and (R)-tert-butyl 2-(4-chloropyrimidin-2-ylamino)-2-methylbutanoate (13a), adjusting the pH of the solution to a suitable value (e.g., pH 3), then adding additional inorganic acid (e.g., HCl) in a suitable organic solvent (e.g., ethyl acetate). (R)-2-(2-chloropyrimidin-4-ylamino)-2-methylbutanoic acid (2a) is purified by recrystallization of the mixture of (R)-2-(2-chloropyrimidin-4-ylamino)-2-methylbutanoic acid (2a) and (R)-2-(4-chloropyrimidin-2-ylamino)-2-methylbutanoic acid (14a) from an organic solvent (e.g., a mixture of ethyl acetate and isopropyl alcohol).

In Scheme II, a compound of Formula 6 is prepared by the addition of a mixture of a compound of Formula 5 in a solvent (e.g., DMF) to a mixture of $Br_2$ in a solvent (e.g., DMF) at a suitable temperature (e.g., about 0° C. to about 10° C.). Preparation of a compound of Formula 7 is achieved by mixing a compound of Formula 6 in an aprotic solvent (e.g., THF) with NaH while cooling to a suitable temperature (e.g., about 10° C. to about 20° C.) and then adding 4-methybenzenesulfonylchloride (TsCl) while maintaining the temperature at (e.g., about 10° C. to about 20° C.). A compound of Formula 8 is then prepared following Scheme II by mixing triisopropyl borate, a compound of Formula 7 and a strong lithium base (e.g., n-butyl lithium (n-BuLi)) in an organic solvent (e.g., THF) at a suitable temperature (e.g., about −90 to about −80° C.). Preparation of a compound of Formula 1 is achieved by adding pinacolate alcohol to a compound of Formula 8 in an organic solvent (e.g., dichloromethane) at a suitable temperature (e.g., about 20 to about 30° C.). In Scheme II, radical $R^1$ is as defined herein.

In another embodiment, the invention provides a process and intermediates to prepare a compound of Formula Ia as described below in Scheme IIa.

Scheme IIa:

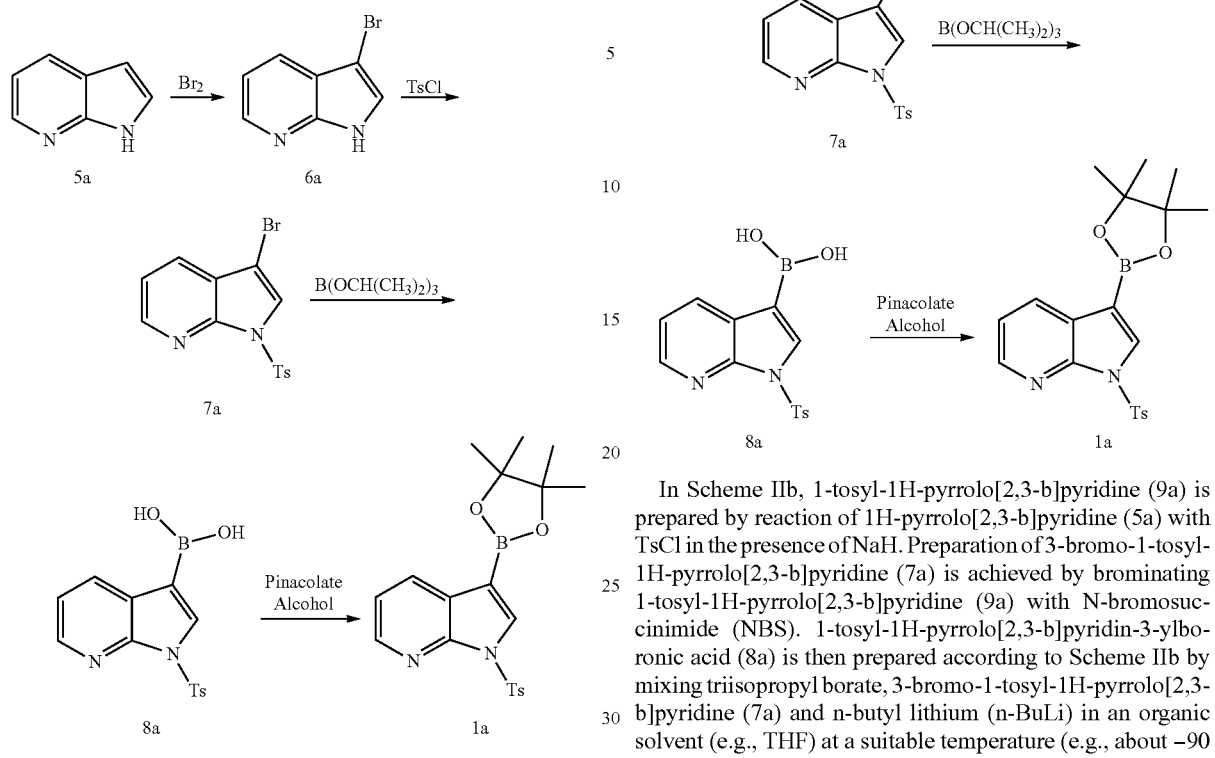

In Scheme IIa, 3-bromo-1H-pyrrolo[2,3-b]pyridine (6a) is prepared by the addition of a mixture of 1H-pyrrolo[2,3-b]pyridine (5a) in a solvent (e.g., DMF) to a mixture of Br₂ in a solvent (e.g., DMF) at a suitable temperature (e.g., about 0° C. to about 10° C.). Preparation of 3-bromo-1-tosyl-1H-pyrrolo[2,3-b]pyridine (7a) is achieved by mixing 3-bromo-1H-pyrrolo[2,3-b]pyridine (6a) in an aprotic solvent (e.g., THF) with NaH while cooling to a suitable temperature (e.g., about 10° C. to about 20° C.) and then adding p-toluenesulfonyl chloride while maintaining the temperature at a suitable temperature (e.g., about 10° C. to about 20° C.). 1-tosyl-1H-pyrrolo[2,3-b]pyridin-3-ylboronic acid (8a) is then prepared according to Scheme IIa by mixing triisopropyl borate, 3-bromo-1-tosyl-1H-pyrrolo[2,3-b]pyridine (7a) and n-butyl lithium (n-BuLi) in an organic solvent (e.g., THF) at a suitable temperature (e.g., about −90 to about −80° C.). Preparation of 3-(4,4,5,5-tetramethyl-1,3,2-dioxaborolan-2-yl)-1-tosyl-1H-pyrrolo[2,3-b]pyridine (1a) is achieved by adding pinacolate alcohol to 1-tosyl-1H-pyrrolo[2,3-b]pyridin-3-ylboronic acid (8a) in an organic solvent (e.g., dichloromethane) at a suitable temperature (e.g., about 20° C. to about 30° C.).

Scheme IIb:

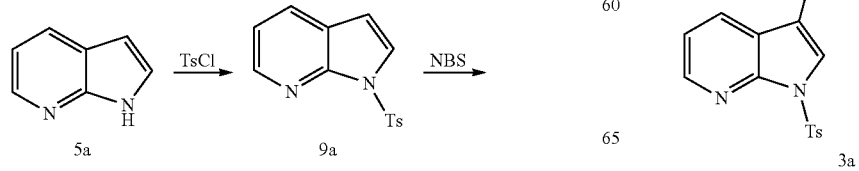

In Scheme IIb, 1-tosyl-1H-pyrrolo[2,3-b]pyridine (9a) is prepared by reaction of 1H-pyrrolo[2,3-b]pyridine (5a) with TsCl in the presence of NaH. Preparation of 3-bromo-1-tosyl-1H-pyrrolo[2,3-b]pyridine (7a) is achieved by brominating 1-tosyl-1H-pyrrolo[2,3-b]pyridine (9a) with N-bromosuccinimide (NBS). 1-tosyl-1H-pyrrolo[2,3-b]pyridin-3-ylboronic acid (8a) is then prepared according to Scheme IIb by mixing triisopropyl borate, 3-bromo-1-tosyl-1H-pyrrolo[2,3-b]pyridine (7a) and n-butyl lithium (n-BuLi) in an organic solvent (e.g., THF) at a suitable temperature (e.g., about −90 to about −80° C.). Preparation of 3-(4,4,5,5-tetramethyl-1,3,2-dioxaborolan-2-yl)-1-tosyl-1H-pyrrolo[2,3-b]pyridine (1a) is achieved by adding pinacolate alcohol to 1-tosyl-1H-pyrrolo[2,3-b]pyridin-3-ylboronic acid (8a) in an organic solvent (e.g., dichloromethane) at a suitable temperature (e.g., about 20° C. to about 30° C.).

Scheme IIc:

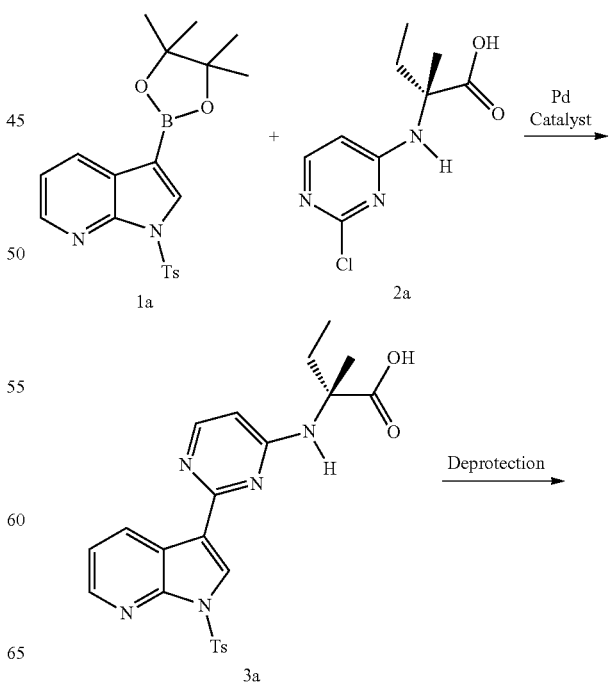

101

-continued

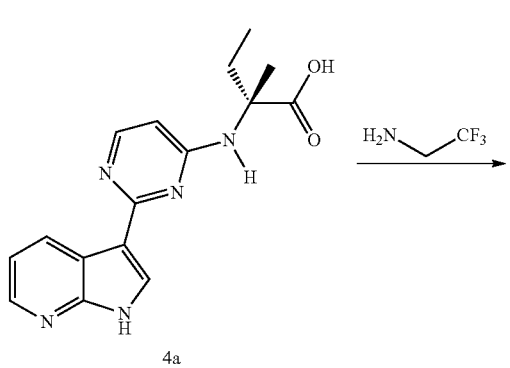

In Scheme IIc, Compound 1a is coupled with Compound 2a via a palladium catalyzed cross coupling reaction to generate Compound 3a. Compound 3a is deprotected (e.g., via treatment with a base) to generate Compound 4a. Compound 4a is then coupled with 2,2,2-trifluoroethylamine in the presence of a coupling reagent to generate Compound 1a.

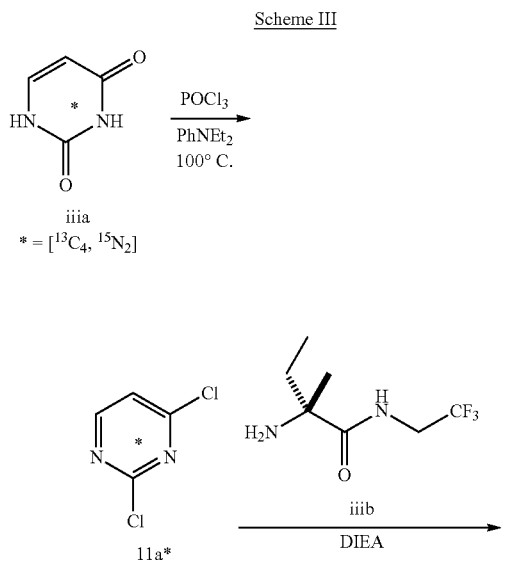

102

-continued

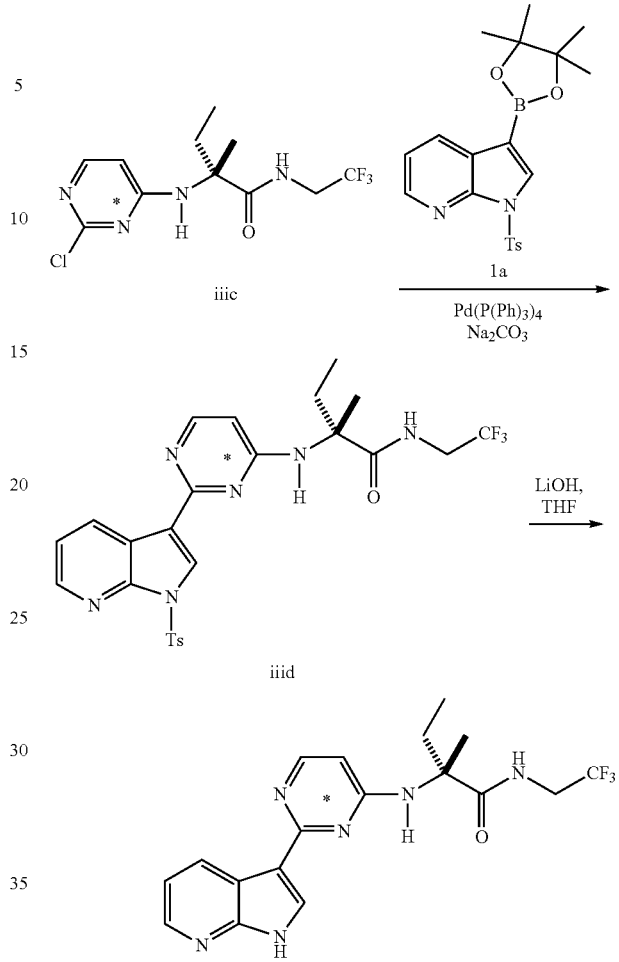

Scheme III is useful for preparing [$^{13}$C,$^{15}$N]-enriched compounds of Formula I. [$^{13}$C,$^{15}$N]-enriched pyrimidine-2,4(1H,3H)-dione (iiia) ([$^{13}$C,$^{15}$N]-enriched labeled uracil), is reacted with POCl$_3$ in the presence of a base, PhNEt$_2$, under heat to generate [$^{13}$C,$^{15}$N]-enriched 2,4-dichloropyrimidine (11a*). [$^{13}$C,$^{15}$N]-enriched 2,4-dichloropyrimidine (11a*) is coupled with 2-amino-2-methyl-N-(2,2,2-trifluoroethyl)propanamide (iiib) under basic conditions to generate [$^{13}$C,$^{15}$N]-enriched (R)-2-((2-chloropyrimidin-4-yl)amino)-2-methyl-N-(2,2,2-trifluoroethyl)butanamide (iiic). And, [$^{13}$C,$^{15}$N]-enriched (R)-2-((2-chloropyrimidin-4-yl)amino)-2-methyl-N-(2,2,2-trifluoroethyl)butanamide (iiic) is coupled with 3-(4,4,5,5-tetramethyl-1,3,2-dioxaborolan-2-yl)-1-tosyl-1H-pyrrolo[2,3-b]pyridine (1a) via a transition metal (i.e. Pd(P(Ph)$_3$)$_4$) catalyzed cross-coupling reaction to generate [$^{13}$C,$^{15}$N]-enriched (R)-2-methyl-2-((2-(1-tosyl-1H-pyrrolo[2,3-b]pyridin-3-yl)pyrimidin-4-yl)amino)-N-(2,2,2-trifluoroethyl)butanamide (iiid), and deprotecting [$^{13}$C,$^{15}$N]-enriched (R)-2-methyl-2-((2-(1-tosyl-1H-pyrrolo[2,3-b]pyridin-3-yl)pyrimidin-4-yl)amino)-N-(2,2,2-trifluoroethyl)butanamide (iiid) to generate [$^{13}$C,$^{15}$N]-enriched (R)-2-((2-(1H-pyrrolo[2,3-b]pyridin-3-yl)pyrimidin-4-yl)amino)-2-methyl-N-(2,2,2-trifluoroethyl)butanamide (Ia*).

Scheme IV:

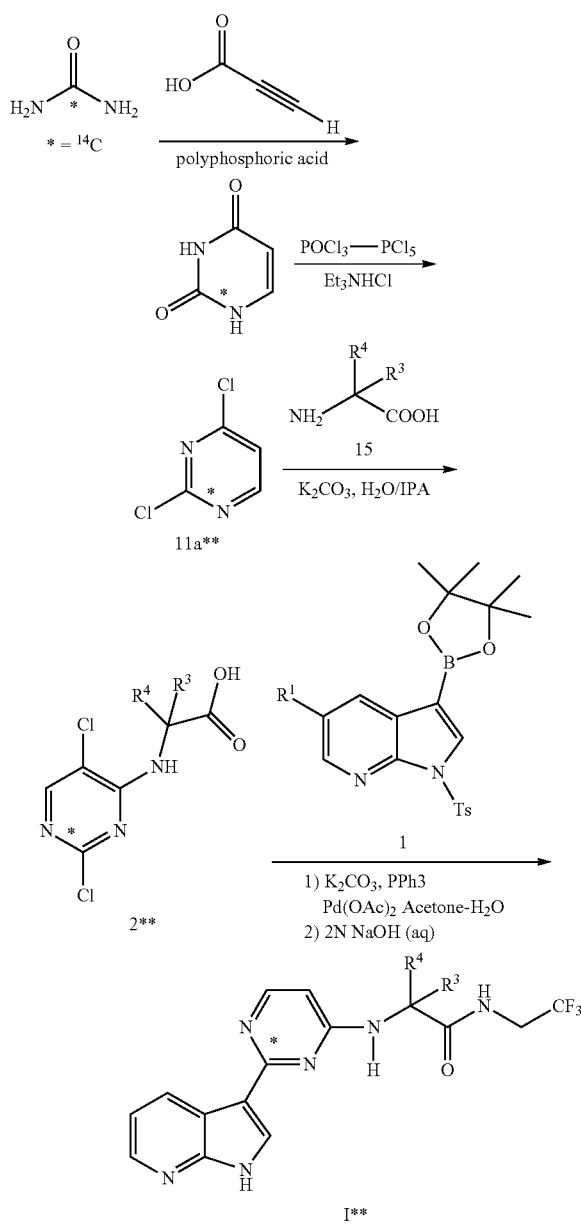

In Scheme IV, [$^{14}$C]-enriched urea is reacted with propiolic acid to generate [$^{14}$C]-enriched uracil, which is reacted with POCl$_3$ and PCl$_5$ to generate [$^{14}$C]-enriched 2,4-dichloropyrimidine (11a). [$^{14}$C]-enriched 2,4-dichloropyrimidine is coupled with the compound of Formula 15 to generate the [$^{14}$C]-enriched compound of Formula 2. And, the [$^{14}$C]-enriched compound of Formula 2 is reacted with the compound of Formula 1 to generate the compound of Formula I.

The schemes above are useful for generating novel intermediates that are useful for generating compounds of Formula I.

The present invention also provides a solid form of (R)-2-(2-(1H-pyrrolo[2,3-b]pyridin-3-yl)pyrimidin-4-ylamino)-2-methylbutanoic acid (4a) designated as Form E. In some embodiments, solid Form E is characterized by one or more peaks corresponding to 2-theta values measured in degrees of 7.1±0.2, 8.2±0.2, 23.9±0.2, and 24.8±0.2 in an X-ray powder diffraction pattern.

Referring to FIG. 1, in one embodiment, the solid Form E is characterized by an XRPD Pattern having the following peaks:

| 2-Theta | Relative Intensity (%) |
|---------|------------------------|
| 7.07    | >30%                   |
| 8.24    | >30%                   |
| 14.29   | >30%                   |
| 23.83   | >30%                   |
| 24.82   | >30 %                  |

In another embodiment, the solid Form E is characterized by an XRPD Pattern having the following peaks:

| 2-Theta | Relative Intensity (%) |
|---------|------------------------|
| 7.07    | >10%                   |
| 8.24    | >10%                   |
| 12.26   | >10%                   |
| 13.87   | >10%                   |
| 14.29   | >10%                   |
| 14.96   | >10%                   |
| 16.33   | >10%                   |
| 18.38   | >10%                   |
| 18.96   | >10%                   |
| 19.93   | >10%                   |
| 23.83   | >10%                   |
| 24.82   | >10%                   |
| 25.33   | >10%                   |
| 25.79   | >10%                   |
| 28.17   | >10%                   |
| 28.88   | >10%                   |
| 29.62   | >10%                   |
| 32.32   | >10%                   |
| 36.68   | >10%                   |
| 38.41   | >10%                   |

The present invention also provides a solid form of (R)-2-(2-(1H-pyrrolo[2,3-b]pyridin-3-yl)pyrimidin-4-ylamino)-2-methylbutanoic acid (4a) designated as Form B. In some embodiments, the solid Form B is characterized by one or more peaks corresponding to 2-theta values measured in degrees of 9.2±0.2, 18.1±0.2, 19.1±0.2, and 32.0±0.2 in an X-ray powder diffraction pattern. In other embodiments, solid Form B is further characterized by one or more peaks corresponding to 2-theta values measured in degrees of 21.4±0.2, 30.1±0.2, 29.9±0.2, and 26.1±0.2 in an X-ray powder diffraction pattern.

Figure 2:
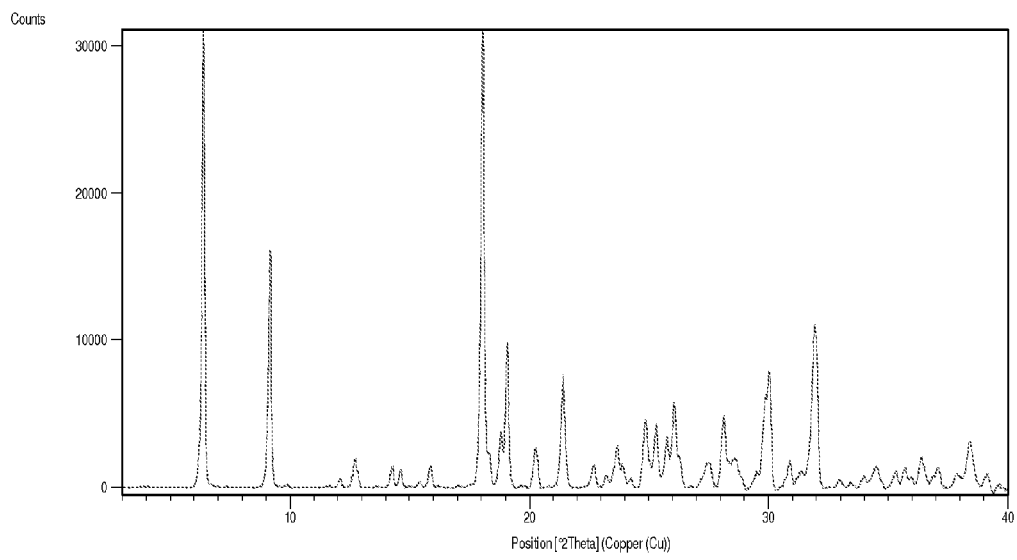
FIG. 2 is an XRPD pattern of Form B of Compound (4a).

Referring to FIG. 2, in one embodiment, the solid Form B is characterized by an XRPD Pattern having the following peaks:

| 2-Theta | Relative Intensity (%) |
|---------|------------------------|
| 6.40    | >30%                   |
| 9.12    | >30%                   |
| 18.07   | >30%                   |
| 19.09   | >30%                   |
| 21.42   | >30%                   |

In another embodiment, the solid Form B is characterized by an XRPD Pattern having the following peaks:

| 2-Theta | Relative Intensity (%) |
|---|---|
| 6.40 | >10% |
| 9.19 | >10% |
| 18.07 | >10% |
| 18.81 | >10% |
| 19.09 | >10% |
| 21.43 | >10% |
| 24.88 | >10% |
| 25.32 | >10% |
| 25.75 | >10% |
| 26.06 | >10% |
| 28.15 | >10% |
| 29.87 | >10% |
| 30.06 | >10% |
| 31.92 | >10% |
| 32.02 | >10% |

Figure 3:
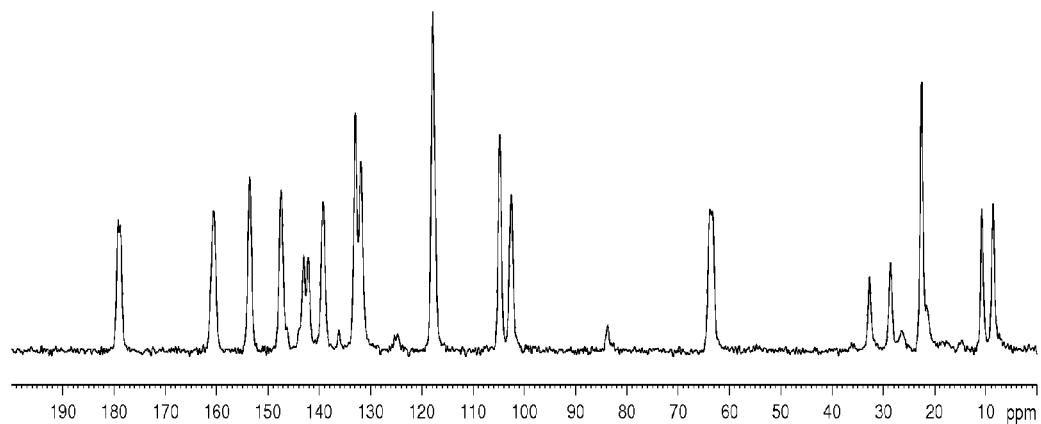
FIG. 3 is a solid state $^1$H NMR spectrum for Form B of Compound (4a) according to procedure (H).

In another embodiment, the solid Form B has the solid state $^1$H NMR spectrum presented in FIG. 3.

Figure 4:
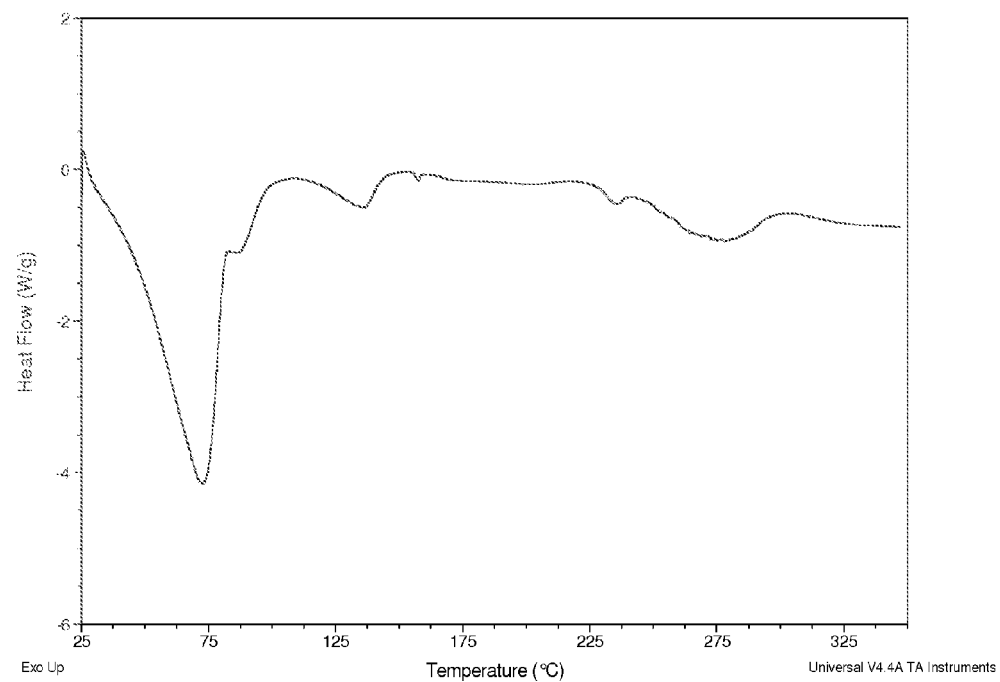
FIG. 4 is a DSC thermogram of Form B of Compound (4a).

Referring to FIG. 4, in another embodiment, the solid Form B is characterized by a dehydration temperature of about 73° C. In other examples, solid Form B is characterized by an onset temperature of about 40° C. And, in some examples, solid Form B is characterized by a dehydration heat of about 725 J/g. In another embodiment, solid Form B is characterized by a dehydration temperature of about 137° C. In other examples, solid Form B is characterized by an onset temperature of about 166° C. And, in some examples, solid Form B is characterized by dehydration heat of 42.0 J/g.

Figure 5:
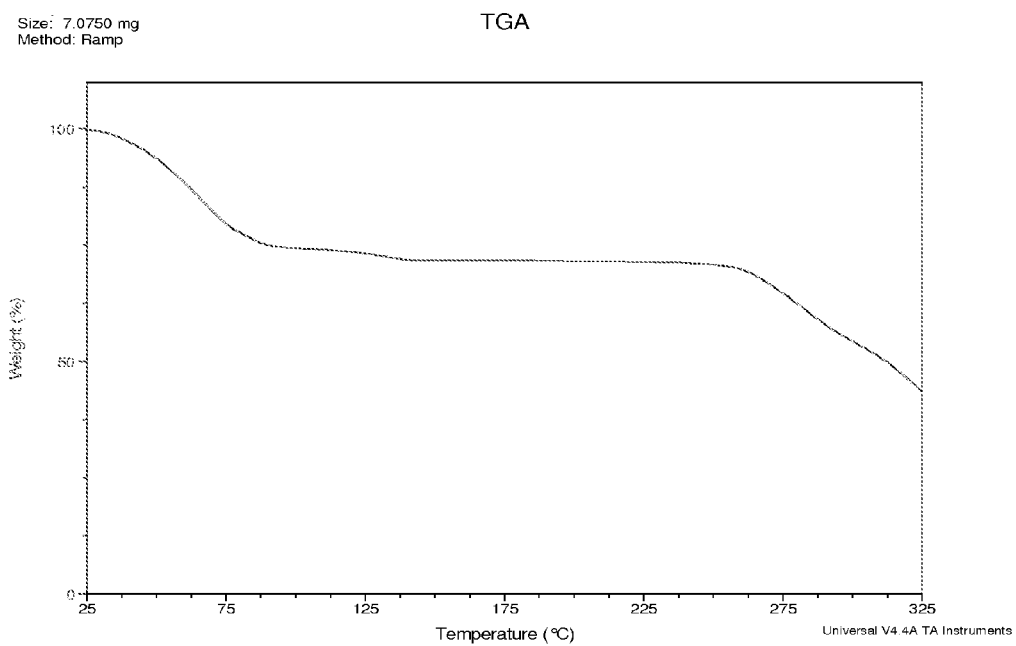
FIG. 5 is a thermogravimetric trace of Form B of Compound (4a).

Referring to FIG. 5, in another embodiment, the solid Form B undergoes a 25.6% weight loss from ambient temperature to 99.4° C. And, in some embodiments, the solid Form B undergoes a 2.6% weight loss from 99.4° C. to 157.7° C.

The present invention also provides a solid form of (R)-2-(2-(1H-pyrrolo[2,3-b]pyridin-3-yl)pyrimidin-4-ylamino)-2-methyl-N-(2,2,2-trifluoroethyl)butanamide (Ia) designated as Form A. In some embodiments, solid Form A is characterized by one or more peaks corresponding to 2-theta values measured in degrees of 23.7±0.2, 11.3±0.2, 19.3±0.2, and 15.4±0.2 in an X-ray powder diffraction pattern. In other embodiments, solid Form A is further characterized by one or more peaks corresponding to 2-theta values measured in degrees of 28.9±0.2 and 21.5±0.2 in an X-ray powder diffraction pattern.

Figure 6:
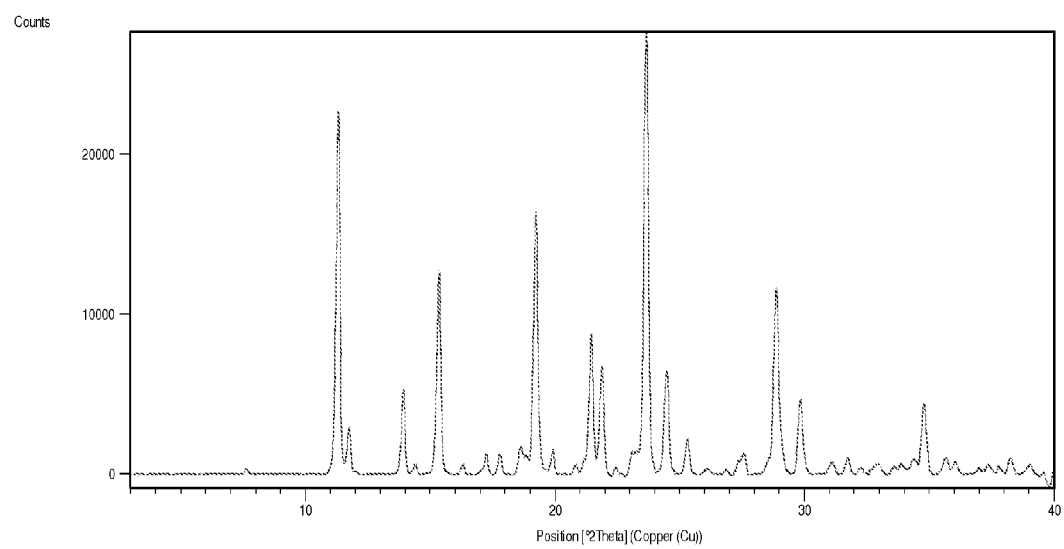
FIG. 6 is an XRPD pattern of Form A of Compound (Ia).

Referring to FIG. 6, in one embodiment, the solid Form A is characterized by an XRPD Pattern having the following peaks:

| 2-Theta | Relative Intensity (%) |
|---|---|
| 11.35 | >30% |
| 15.39 | >30% |
| 19.26 | >30% |
| 21.47 | >30% |
| 23.69 | >30% |
| 28.88 | >30% |

In another embodiment, the solid Form A is characterized by an XRPD Pattern having the following peaks:

| 2-Theta | Relative Intensity (%) |
|---|---|
| 11.3492 | >10% |
| 11.78 | >10% |
| 13.95 | >10% |
| 15.39 | >10% |
| 19.26 | >10% |
| 21.47 | >10% |
| 23.69 | >10% |
| 24.53 | >10% |
| 28.88 | >10% |
| 29.86 | >10% |
| 34.83 | >10% |

Figure 7:
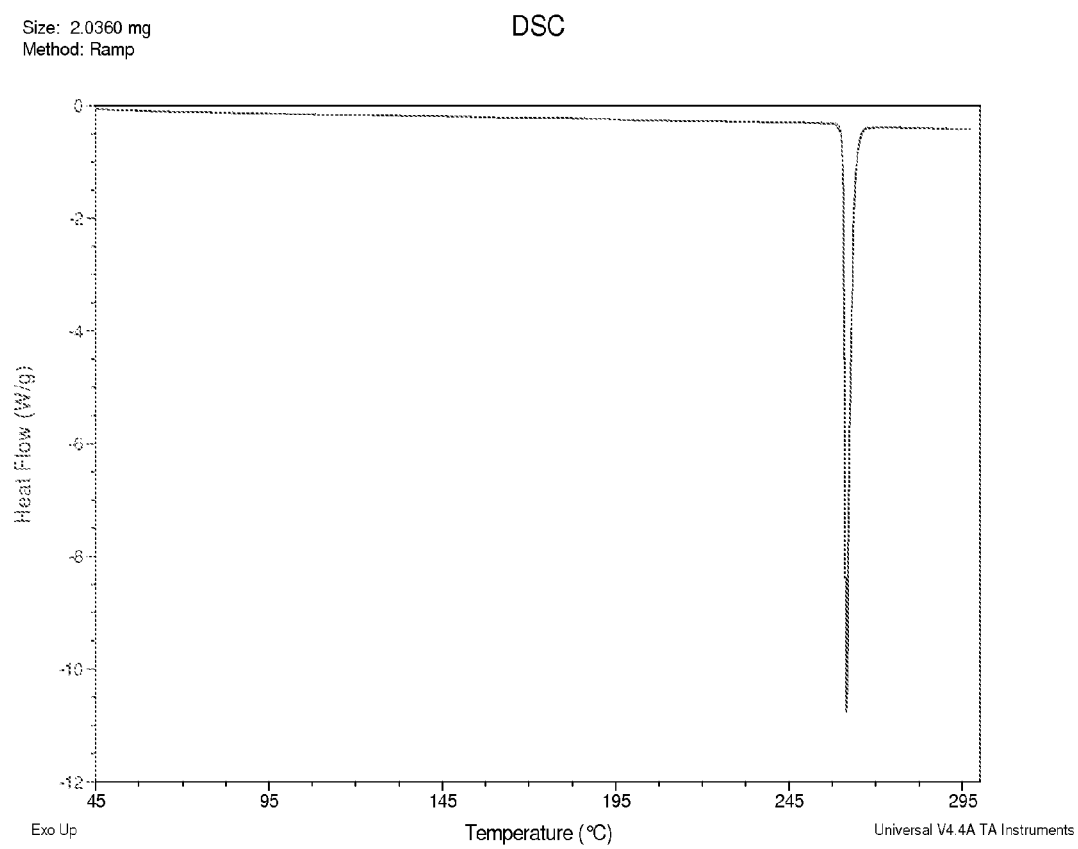
FIG. 7 is a DSC thermogram of Form A of Compound (Ia).

Referring to FIG. 7, in another embodiment, the solid Form A is characterized by a melting point of about 262° C. In other examples, solid Form A is characterized by onset temperature of about 260.8° C. And, in some examples, solid Form A is characterized by melting heat of about 140.5 J/g.

The following preparative examples are set forth in order that this invention is more fully understood. These examples are for the purpose of illustration only and are not to be construed as limiting the scope of the invention in any way.

Analytical Methods Used:

(A) HPLC on C18 column. Mobile phase was acetonitrile/water/TFA (60:40:0.1). Flow rate was 1.0 mL/min. Detection at wavelength of 230 nm. Run time was 25-26 minutes.

(B) HPLC on C18 column. Mobile phase was acetonitrile/water/TFA (90:10:0.1). Flow rate was 1.0 mL/min. Detection at wavelength of 230 nm.

(C) HPLC on a Waters XBridge Phenyl column, 4.6×150 mm, 3.5 µm. Mobile phase A was water/1M ammonium formate, pH 4.0 (99:1). Mobile phase B was acetonitrile/water/1M ammonium formate, pH 4.0 (90:9:1). Gradient 5% to 90% B in 15 minutes. Total run time 22 minutes. Flow rate 1.5 mL/min. Detection at UV, 245 nm. T=25° C.

(D) HPLC on a Waters XBridge Phenyl column, 4.6×150 mm, 3.5 p.m. Mobile phase A was water/1M ammonium formate, pH 4.0 (99:1). Mobile phase B was acetonitrile/water/1M ammonium formate, pH 4.0 (90:9:1). Gradient 15% to 90% B in 15 minutes. Total run time 22 minutes. Flow rate 1.5 mL/min. Detection at UV, 220 nm. T=35° C.

(E) XRPD Analysis: The XRPD patterns were acquired with either a Bruker D8 Discover or Bruker D8 Advance diffractometer.

Bruker D8 Advance System: The XRPD patterns were recorded at room temperature in reflection mode using a Bruker D8 Advance diffractometer equipped with a sealed tube Cu source and a Vantec PSD detector (Bruker AXS, Madison, Wis.). The X-ray generator was operating at a voltage of 40 kV and a current of 40 mA. The powder sample was placed in a silicon or PMM holder. The data were recorded in a q-q scanning mode over the range of 4°-45° 2q with a step size of 0.014° and a dwell time of is per step.

Bruker D8 Discover System: The XRPD patterns were acquired at room temperature in reflection mode using a Bruker D8 Discover diffractometer equipped with a sealed tube source and a Hi-Star area detector (Bruker AXS, Madison, Wis.). The X-Ray generator was operating at a voltage of 40 kV and a current of 35 mA. The powder sample was placed in a nickel holder. Two frames were registered with an exposure time of 120 s each. The data frames were subsequently integrated over the range of 4.5°-22.4° and 21.0°-39.0° 2q merged into one continuous pattern.

(F) Thermogravimetric Analysis (TGA): TGA was conducted on a TA Instruments model Q5000 thermogravimetric analyzer. Approximately 1-4 mg of solid sample was placed in a platinum sample pan and heated in a 90 mL/min nitrogen stream at 10° C./min to 300° C. All thermograms were analyzed using TA Instruments Universal Analysis 2000 software V4.4A.

(G) Differential Scanning calorimetry (DSC): DSC was conducted on a TA Instruments model Q2000 calorimetric analyzer. Approximately 1-4 mg of solid sample was placed in a crimped aluminum pinhole pan and heated in a 50 mL/min nitrogen stream at 10° C./min to 300° C. All data were analyzed using TA Instruments Universal Analysis 2000 software V4.4A.

(H) SSNMR Experimental: Solid state NMR spectra were acquired on the Bruker-Biospin 400 MHz Advance III widebore spectrometer equipped with Bruker-Biospin 4 mm HFX probe. Samples were packed into 4 mm $ZrO_2$ rotors (approximately 70 mg or less, depending on sample availability). Magic angle spinning (MAS) speed of typically 12.5 kHz was applied. The temperature of the probe head was set to 275K to minimize the effect of frictional heating during spinning. The proton relaxation time was measured using $^1H$ MAS $T_1$ saturation recovery relaxation experiment in order to set up proper recycle delay of the $^{13}C$ cross-polarization (CP) MAS experiment. The recycle delay of $^{13}C$ CPMAS experiment was adjusted to be at least 1.2 times longer than the measured $^1H$ $T_1$ relaxation time in order to maximize the carbon spectrum signal-to-noise ratio. The CP contact time of $^{13}C$ CPMAS experiment was set to 2 ms. A CP proton pulse with linear ramp (from 50% to 100%) was employed. The Hartmann-Hahn match was optimized on external reference sample (glycine). SPINAL 64 decoupling was used with the field strength of approximately 100 kHz. The chemical shift was referenced against external standard of adamantane with its upfield resonance set to 29.5 ppm.

The following preparative examples are set forth in order that this invention is more fully understood. These examples are for the purpose of illustration only and are not to be construed as limiting the scope of the invention in any way.

Example 1

3-(4,4,5,5-tetramethyl-1,3,2-dioxaborolan-2-yl)-1-tosyl-1H-pyrrolo[2,3-b]pyridine (1a)

EXAMPLE 1a 3-bromo-1H-pyrrolo[2,3-b]pyridine (6a)

7-azaindole (5a) (6.9 kg, 58.4 moles) was added to a 200 L glass-lined reactor containing 52.6 kg DMF. A solution of $Br_2$ in DMF (9.7 kg $Br_2$ in 14.7 kg DMF) was added drop wise to maintain the mixture temperature of about 0-10° C. After the addition was complete, the temperature was maintained at about 0-10° C. The completeness of the reaction was measured by HPLC (method A) with sample aliquots after 30 minutes. The reaction was considered complete when the 7-azaindole was less than 3% (after about 2 hours and 40 minutes).

The reaction was quenched with 10% aqueous solution of $NaHSO_3$ (17.5 kg) while maintaining the temperature below 15° C. A saturated aqueous solution of $NaHCO_3$ (61.6 kg) below 25° C. was added to adjust the pH to about 7 to 8. After neutralization, the mixture was transferred into a 50 L vacuum filter and filtered. The resultant cake was washed with water (18 kg) and then petroleum ether (12 kg). The cake was dried in a tray dryer at about 50-60° C. until the water content detected by KF (Karl Fisher reaction) was less than 0.8%. A yellow solid resulted (10.3 kg, 99.1% purity as measured by HPLC (method A), 89.6% yield of 3-bromo-1H-pyrrolo[2,3-b]pyridine (6a)).

EXAMPLE 1b 3-bromo-1-tosyl-1H-pyrrolo[2,3-b]pyridine (7a)

3-bromo-1H-pyrrolo[2,3-b]pyridine (6a) (10.7 kg, 54.3 moles) was added to 94.3 kg of THF in a 200 L glass-lined reactor. The solid was dissolved completely by stifling. After the mixture was cooled to about 10-15° C., NaH (3.4 kg, 85 moles) was added in portions (about 200-250 g each portion) every 3 to 5 minutes while venting any $H_2$ gas released by the reaction. After the addition of NaH, the mixture was stirred for one hour while maintaining the temperature of about 10-20° C. 4-methylbenzenesulfonylchloride (12.4 kg, 65.0 moles) was added at a rate of 0.5 kg/10 minutes at about 10-20° C. After the addition was complete, the temperature was maintained at about 10-20° C. The completeness of the reaction was measured by HPLC (method A) with sample aliquots after 30 minutes. The reaction was considered complete when the peak area of 3-bromo-1H-pyrrolo[2,3-b]pyridine (6a) was less than 1% (after about 1.5 hours).

The reaction was quenched with water (10.7 kg) while maintaining the temperature below 20° C. Dichloromethane (41.3 kg) was added to the mixture. Then 3% HCl (42.8 kg) was added into the mixture while maintaining the temperature below 25° C. After the addition, the phases were allowed to separate for 0.5 hour. The aqueous phase was extracted twice with dichloromethane. During each extraction, the mixture was stirred for 15 minutes and then held for 15 minutes. All the organic phases were combined. The combined organic phases were washed with 3% HCl (33.4 kg) and water (40 kg). During each wash, the mixture was stirred for 15 minutes and then held for 30 minutes.

The mixture was transferred into a 50 L vacuum filter and filtered through silica gel (3 kg). The cake was washed with dichloromethane (35 kg) twice. The filtrate and washings were combined. The organic phase was concentrated below 40° C. under vacuum of a pressure less than −0.085 MPa until 10 L mixture remained. Petroleum ether (9 kg) was added into the residue. The mixture was stirred until it was homogeneous. The slurry was transferred into a 50 L vacuum filter and filtered. The cake was washed with petroleum ether (9 kg). A light brown solid resulted (17 kg, 99.7% purity as measured by HPLC analysis (method A), 94% yield of 3-bromo-1-tosyl-1H-pyrrolo[2,3-b]pyridine (7a)).

EXAMPLE 1c 1-tosyl-1H-pyrrolo[2,3-b]pyridin-3-ylboronic acid (8a)

THF (28.5 kg) and 3-bromo-1-tosyl-1H-pyrrolo[2,3-b]pyridine (7a) (4 kg) were added to a 72 L flask. The mixture was stirred until the solid dissolved completely. Triisopropyl borate (3.2 kg) was added and the mixture was cooled to below −80° C. n-BuLi (4.65 kg) was added drop wise at a rate of about 0.6-0.9 kg/hour maintaining the temperature of about −80 to −90° C. After the addition, the temperature was maintained at −80 to −90° C. The completeness of the reaction was measured by HPLC (method A) with sample aliquots after 30 minutes. The reaction was considered complete when the peak area of 3-bromo-1-tosyl-1H-pyrrolo[2,3-b]pyridine (7a) was less than 4%.

Water (2 kg) was slowly added to the mixture to quench the reaction. The mixture temperature returned to about 15-25° C. The mixture was transferred to a 50 L reactor to be concentrated below 40° C. under vacuum of a pressure less than −0.08 MPa until no THF distilled out. The residue was dissolved into water (25 kg) and 10% aqueous NaOH solution (26 kg). The mixture was stirred until the solid dissolved completely. The mixture was transferred into a vacuum filter and filtered. The filtrate was extracted twice with MTBE (21 kg each) at about 20-30° C. During each extraction, the mixture was stirred 15 minutes and held 15 minutes. HCl (28 L) was added into the aqueous phase to adjust the pH to between 3 and 4 while maintaining the temperature of about 10-20° C. The mixture was stirred at about 10-15° C. for 1 hour. The mixture was transferred into a centrifuge and filtered. The resultant cake after filtering was washed with water (5 kg) and petroleum ether (5 kg). The cake was dried at 35-45° C. until the LOD (loss on drying) was less than 3%. An off-white solid resulted (2.5 kg and 98.8% purity as measured by HPLC analysis (method A), 69.4% yield of 1-tosyl-1H-pyrrolo[2,3-b]pyridin-3-ylboronic acid (8a)).

EXAMPLE 1d 3-(4,4,5,5-tetramethyl-1,3,2-dioxaborolan-2-yl)-1-tosyl-1H-pyrrolo[2,3-b]pyridine (1a)

Dichloromethane (165.6 kg) and pinacolate alcohol (3.54 kg) were added to a 200 L glass-lined reactor. The mixture was stirred until the solid dissolved completely. Then, 1-tosyl-1H-pyrrolo[2,3-b]pyridin-3-ylboronic acid (8a) (8.65 kg) was added in portions (2 kg every 5 minutes) while maintaining the temperature of about 20-30° C. After the addition, the temperature was maintained at about 20-30° C. while stirring. The completeness of the reaction was measured by HPLC (method B) with sample aliquots every 60 minutes. The reaction was considered complete when the peak area of 1-tosyl-1H-pyrrolo[2,3-b]pyridin-3-ylboronic acid (8a) was less than 1%.

The mixture was filtered through silica gel (3 kg). The cake was rinsed twice with dichloromethane (15 kg each rinse). The filtrate was combined with the washing liquids, and then concentrated below 30° C. under vacuum at a pressure less than −0.08 MPa until no fraction distilled out. Solvent was continued to be removed by vacuum for 2 hours. Isopropanol (17.2 kg) was added to the residue. The mixture was heated to reflux at about 80-85° C. The mixture refluxed for 30 minutes until the solid dissolved completely. The mixture was cooled below 35° C., and then to about 0-10° C. The mixture crystallized at 0-10° C. for 2 hours and was then filtered. After filtration, the resultant cake was dried at about 35-45° C. until the water content detected by KF (Karl Fisher reaction) was less than 0.5% and the LOD (loss on drying) was less than 0.5%. An off-white solid resulted (8.8 kg and 99.7% purity as measured by HPLC analysis (method B) of 3-(4,4,5,5-tetramethyl-1,3,2-dioxaborolan-2-yl)-1-tosyl-1H-pyrrolo[2,3-b]pyridine (1a)).

EXAMPLE 2a

Preparation of (R)-2-methyl-2-(2-(1-tosyl-1H-pyrrolo[2,3-b]pyridin-3-yl)pyrimidin-4-ylamino)butanoic acid (3a)

Tripotassium phosphate ($K_3PO_4$) (7.20 kg, 3 equiv.) was mixed with three volumes of water (9.0 kg). The mixture was agitated for at least 20 minutes, cooled to a temperature of ≤30° C. and added to acetonitrile (16.8 g, 7 volumes) into a 120 L reactor. The resultant mixture was agitated. 3.0 kg (11.3 moles, 1.0 equiv.) of (R)-2-(2-chloropyrimidin-4-ylamino)-2-methylbutanoic acid hydrochloride (2a) were added to the reaction mixture in the reactor while maintaining a temperature ≤30° C. The mixture was agitated for at least 20 minutes. 5.16 kg (13.0 moles, 1.15 equiv.) of 3-(4,4,5,5-tetramethyl-1,3,2-dioxaborolan-2-yl)-1-tosyl-1H-pyrrolo[2,3-b]pyridine (1a) were then added to the reactor. The reaction mixture was agitated and de-gassed with $N_2$ sparging for at least 30 minutes. The mixture was heated to 65±5° C.

In a separate vessel, 0.075 kg (0.03 equiv.) of palladium(II) acetate was mixed with 4.80 kg (2 volumes) of de-gassed acetonitrile ($CH_3CN$). This mixture was agitated until homogenous. 0.267 kg (1.02 moles, 0.09 equiv.) of triphenylphosphine ($PPh_3$) was added and the resultant mixture was agitated for at least 30 minutes at 20±5° C. The palladium (II) acetate/$PPh_3$/$CH_3CN$ mixture was then added to the reactor above while maintaining the nitrogen purge. The reactor contents were heated to 75±5° C. for at least 17 hours under nitrogen purge. After 5 hours the conversion was shown to be about 86% complete as measured by HPLC analysis (method C) of a 1.0 mL aliquot. Additional catalyst and compound of Formula Ia (900 g, 2.26 moles, 0.2 equiv.) were then added to the reaction mixture and the mixture was stirred. After an additional 12 hours, the reaction was shown to be 99.7% complete as measured by HPLC analysis (method C) of a 1.0 mL aliquot. The additional catalyst added above was prepared by dissolving 37.5 g palladium(II) acetate in 1 volume of acetonitrile (which was de-gassed for 20 minutes), and then adding 133.5 g of triphenylphosphine.

EXAMPLE 2b (R)-2-methyl-2-(2-(1-tosyl-1H-pyrrolo[2,3-b]pyridin-3-yl)pyrimidin-4-ylamino)butanoic acid (3a)

To (R)-2-(2-chloropyrimidin-4-ylamino)-2-methylbutanoic acid hydrochloride (2a) (limiting reagent) and 3-(4,4,5,5-tetramethyl-1,3,2-dioxaborolan-2-yl)-1-tosyl-1H-pyrrolo[2,3-b]pyridine (1.15 eq) add 2-propanol (0.6 vol) and begin degassing with nitrogen. Add 6N aqueous NaOH (3.2 eq) and continue degassing. Charge $PdCl_2(Amphos)_2$ (0.0014 eq) as a slurry in 2-propanol (0.06 vol). Continue the degassing for at least 30 minutes then warm the mixture to a temperature of between 70-75° C. to generate the compound of Formula (3a). The reaction is deemed complete when HPLC analysis shows <1.0% of (R)-2-(2-chloropyrimidin-4-ylamino)-2-methylbutanoic acid hydrochloride (2a) remaining.

EXAMPLE 3a (R)-2-(2-(1H-pyrrolo[2,3-b]pyridin-3-yl)pyrimidin-4-ylamino)-2-methylbutanoic acid (4a)

A solution of 4N aqueous KOH, which was previously prepared with 6.0 kg of KOH in 27.0 kg of water at a rate to control the temperature rise, was added to the reactor above and the reaction was heated to 75±5° C. for at least 5 hours while agitating the mixture. An aliquot of about 1.0 mL was removed from the reaction mixture and analyzed by HPLC (method C) to show 98.6% compound of Formula 4a and 1.4% compound of Formula 3a.

15.0 kg (5 volumes) of water was added to the reactor. The reaction mixture was cooled to 35±5° C. Isopropyl acetate (7.8 g, 3 volumes) was added, and the reaction mixture was agitated for at least 5 minutes. The reaction mixture was filtered through a 4-cm pad of celite in an 18-inch Nutsche filter. The reactor was rinsed with 9.0 kg of water and the water was then used to rinse the celite pad. The aqueous and organic phases were separated. 0.9 kg of Darco G-60 activated carbon (30% w/w) was added to the aqueous phase in a 120-liter reactor. The pH of the mixture was adjusted to less than 1.0 with concentrated HCl solution at 25±10° C. and held for at least 4 hours. If necessary, the pH was readjusted with 6N NaOH. The mixture was then filtered through a Nutshce filter, which was equipped with a filter cloth, and the solids were rinsed with 6.0 kg (2 volumes) of 1N HCl. The filter cake was maintained under positive pressure of nitrogen for at least 30 minutes. The HCl filtrate was agitated and heated to 25±5° C. 0.9 kg of Darco G-60 activated carbon was added to the HCl filtrate and the mixture was stirred for at least 4 hours. The mixture was then filtered through a Nutshce filter, which was equipped with a filter cloth, and the solids were washed with 6.0 kg (2 volumes) of 1N HCl. The second filter cake was maintained under positive pressure of nitrogen for at least 30 minutes.

The HCl filtrate was again agitated and heated, charcoal was added and filtering step was repeated with a Nutshce filter, which was equipped with a 0.45 µm in-line filter between the Nutsche filter and the receiver flask, to yield a third filter cake and a final filtrate. The solids were washed with 6.0 kg of 1N HCl. The third filter cake was maintained under positive pressure of nitrogen for at least 30 minutes.

The pH of the final filtrate was adjusted to between 4.5 and 5.0 using 6N NaOH while the temperature was maintained between 25±5° C. If necessary, the pH was readjusted using 1N HCl. The final filtrate was then cooled to 5±5° C. and agitated for at least 2 hours. The mixture was filtered was filtered with a Nutshce filter, which was equipped with a filter cloth. The solids were rinsed with 6.0 kg (2 volumes) of water. The final filter cake was maintained under positive pressure of nitrogen for at least 30 minutes.

The wet solids (i.e., filter cakes) were dried in a drying oven at ≤60° C. under vacuum, with a nitrogen purge, over 5 days to yield 3.561 kg of (R)-2-(2-(1H-pyrrolo[2,3-b]pyridin-3-yl)pyrimidin-4-ylamino)-2-methylbutanoic acid (4a).

The (R)-2-(2-(1H-pyrrolo[2,3-b]pyridin-3-yl)pyrimidin-4-ylamino)-2-methylbutanoic acid (4a) generated above is designated as Forms B and E. These solid forms were subject to XRPD, solid state $^1$H NMR, and TSG analyses described under (E) and (F), above. The results from these analyses are presented in FIGS. 1-4.

EXAMPLE 3b (R)-2-(2-(1H-pyrrolo[2,3-b]pyridin-3-yl)pyrimidin-4-ylamino)-2-methylbutanoic acid (4a)

To the reaction mixture in Example 2b, charge a solution of KOH (8.8 eq) in water (7.3 vol) and agitate the batch at a temperature of from 70-75° C. until HPLC analysis shows conversion from the intermediate to (R)-2-(2-(1H-pyrrolo[2,3-b]pyridin-3-yl)pyrimidin-4-ylamino)-2-methylbutanoic acid (4a) reaches >99%. Cool the batch to 20-25° C. then charge Darco G-60 activated carbon (30 wt % based on the compound of Formula (2a)) and agitate the batch for 12-24 hrs at 20-25° C. Filter the slurry, rinsing the solids with water (2×1 vol). Cool the batch to 15-20° C. then adjust the pH of the batch to <5 with conc. HCl while maintaining a batch temperature no more than 20-25° C. Perform fine adjustment of pH back to 5.5-6 (target pH 6) via 6M NaOH. Adjust the batch temperature to 20-25° C. then seed with the compound of Formula (2a) (0.4 wt % dry seed). Stir the slurry for no less than 2 hrs. Charge water (12 vol) over 8 hrs then stir the slurry for no less than 4 hrs. Filter the batch and rinse the cake with water (2×2 vol) then n-heptane (2 vol). Dry the solids at 80° C. to give (R)-2-(2-(1H-pyrrolo[2,3-b]pyridin-3-yl)pyrimidin-4-ylamino)-2-methylbutanoic acid (4a).

EXAMPLE 3c (R)-2-(2-(1H-pyrrolo[2,3-b]pyridin-3-yl)pyrimidin-4-ylamino)-2-methylbutanoic acid (4a)

To the reaction mixture in Example 2b, charge a solution of KOH (8.8 eq) in water (7.3 vol) and agitate the batch at a temperature of from 70-75° C. until HPLC analysis shows conversion from the intermediate to (R)-2-(2-(1H-pyrrolo[2,3-b]pyridin-3-yl)pyrimidin-4-ylamino)-2-methylbutanoic acid (4a) reaches >99%. Cool the batch to 15-25° C. and adjust the pH to <5 with conc. HCl. Perform a fine adjustment of the pH to 5.5-6 using 6M NaOH. Adjust the batch temperature to 20-25° C., and seed the seed with the compound of Formula (2a) (0.4 wt % dry seed). Stir the slurry for not less than 2 hrs. Charge water (12 vol) over 8 hrs then stir the slurry for not less than 4 hrs. Filter the batch and rinse the cake with water (2×2 vol) then n-heptane (2 vol). Dry the solids at 80° C. to give (R)-2-(2-(1H-pyrrolo[2,3-b]pyridin-3-yl)pyrimidin-4-ylamino)-2-methylbutanoic acid (4a).

EXAMPLE 4a

Preparation of (R)-2-(2-(1H-pyrrolo[2,3-b]pyridin-3-yl)pyrimidin-4-ylamino)-2-methyl-N-(2,2,2-trifluoroethyl)butanamide (1a)

Diisopropylethylamine (DIEA) (3.61 kg, 28.1 moles, 2.5 equiv.) was added to (R)-2-(2-(1H-pyrrolo[2,3-b]pyridin-3-yl)pyrimidin-4-ylamino)-2-methylbutanoic acid (4a) (3.5 kg, 11.24 moles, 1.0 equiv.) in 7 volumes (32.6 kg) of dichloromethane ($CH_2Cl_2$ or DCM) while keeping the temperature at ≤30° C. Water (0.103 kg) was added to make 5.5±0.5% total water content for the reaction system, and the mixture was stirred at ≤30° C. for at least 30 minutes. The reaction mixture was cooled to 0±5° C. Propylphosphonic anhydride solution (17.9 kg, 28.1 moles, 2.5 equiv.) was added to the mixture while maintaining the temperature below 20° C. The mixture was agitated for at least an hour keeping the temperature at 20±5° C., then 2,2,2-trifluoroethylamine (1.68 kg, 16.86 moles, 1.5 equiv.) was added while maintaining the temperature below 20° C. The reaction mixture was warmed to 25±5° C. and agitated for 5 hours while holding the temperature. A 1.0 mL aliquot was removed and the reaction was determined to be 100% complete. Water (17.5 kg, 5 volumes) was added to the reaction mixture, and the resultant mixture was agitated for at least 30 minutes while maintaining the temperature below 30° C.

The mixture was concentrated under vacuum with a rotary evaporator at a temperature ≤45° C. Isopropylacetate (1.55 kg, 0.5 volumes) was added to the concentrated aqueous solution, and the pH of the solution was adjusted to 7.5-8.0 using 6N NaOH solution at ≤35° C. The mixture was cooled to 10±5° C. and stirred at for at least one hour. If necessary, 6N HCl was added to readjust the pH of mixture to 7.5-8.0. The resultant slurry was filtered and washed with water (10.5 kg, 3 volumes). The filter cake was maintained under positive pressure of nitrogen for at least 30 minutes. The wet cake was dissolved in methanol (44.7 kg, 12 volumes) by agitation, and the solution was treated with PL-BnSH MP-Resin (BN-SHMP) polymer resin (0.235 kg of 5% wt of resin) at 25±5° C. After agitating at 25±5° C. for at least 12 hours, the mixture was filtered. The solids were washed with methanol (2.77 kg, 1 volume). The filtrate was concentrated under vacuum in a rotary evaporator at a temperature ≤50° C. The filtrate was not concentrated to dryness. The concentrated filtrate was allowed to sit at room temperature for about 2.5 days. The mixture was then stirred until homogeneous and heated to 40° C., followed by slow addition of pre-heated water (56.1 kg at 45° C.) while maintaining a temperature of 45±5° C. After the mixture was spun for 1 hour, the remaining methanol was concentrated further, but not concentrated to dryness. The resultant mixture was cooled down to at least 5±5° C. and agitated for at least 2 hours. The product was filtered, and the solids were washed with water (10.5 kg, 3 volumes). The filter cake was maintained under positive pressure of nitrogen for at least 30 minutes. The isolated product was dried to a constant weight under vacuum in a drying oven at a temperature of ≤70° C. with a nitrogen purge to yield (R)-2-(2-(1H-pyrrolo[2,3-b]pyridin-3-yl)pyrimidin-4-ylamino)-2-methyl-N-(2,2,2-trifluoroethyl)butanamide (Ia) (4.182 kg, white powder, 0.18% water content, 98.6% AUC using HPLC (method D)).

The solid state (R)-2-(2-(1H-pyrrolo[2,3-b]pyridin-3-yl)pyrimidin-4-ylamino)-2-methyl-N-(2,2,2-trifluoroethyl)butanamide (Ia) generated above, is designated as Form A. This compound was subject to XRPD, TGS, and DSC analyses described under (E) and (F), above. The results from these analyses are presented in FIGS. 5-7.

EXAMPLE 4b

Preparation of (R)-2-(2-(1H-pyrrolo[2,3-b]pyridin-3-yl)pyrimidin-4-ylamino)-2-methyl-N-(2,2,2-trifluoroethyl)butanamide (Ia)

To (R)-2-(2-(1H-pyrrolo[2,3-b]pyridin-3-yl)pyrimidin-4-ylamino)-2-methylbutanoic acid (4a) (limiting reagent) charge 2-methylTHF (7.5 vol), then charge $T_3P$® (2.0 eq, 50% w/w in 2-MeTHF). Heat the mixture to 60-65° C. and maintain this temperature for no less than 3 hrs and the solids are completely dissolved. Cool to 20-25° C. then charge 2,2,2-trifluoroethylamine (2.0 eq). Continue agitation for no less than 6 hrs at 20-25° C. and until HPLC analysis showed <1.0% of (R)-2-(2-(1H-pyrrolo[2,3-b]pyridin-3-yl)pyrimidin-4-ylamino)-2-methylbutanoic acid (4a). Slowly charge a $Na_2CO_3$ solution (15 vol, 1.165M) while maintaining a batch temperature <30° C. Stir the mixture for 30 min then separate the phases. Wash the organic phase with water (4 vol). Emulsions have been observed at this point and can be addressed through addition of NaCl solution. Charge methanol (7 vol) then distill to 4 vol. Repeat 3 times. Prior to crystallization, adjust the total volume to approximately 11 vol. Heat the mixture to 50-55° C. then add water (2.45 vol, final solvent composition 22% water in methanol) over 30 min. Seed the batch with (R)-2-(2-(1H-pyrrolo[2,3-b]pyridin-3-yl)pyrimidin-4-ylamino)-2-methyl-N-(2,2,2-trifluoroethyl)butanamide (Ia) (1 wt % seed based on the compound of Formula (4a)). Stir for 4 hrs at 50-55° C. then add water over 24 h until the mixture is approximately 58 wt % water in methanol. Cool to 20-25° C., stir 1 h, then filter. Wash the cake with water (2 vol). Dry the solids at 60-65° C. to give (R)-2-(2-(1H-pyrrolo[2,3-b]pyridin-3-yl)pyrimidin-4-ylamino)-2-methyl-N-(2,2,2-trifluoroethyl)butanamide (Ia).

EXAMPLE 5

Preparation of (R)-2-(2-chloropyrimidin-4-ylamino)-2-methylbutanoic acid hydrochloride (2a)

To a solution of $K_2CO_3$ (2 eq.) in water (3 vol) was added D-isovaline.HCl (1.0 eq.). The resulting solution was stirred for 20 min. then 2,4-dichloropyrimidine (1.1 eq.) and IPA (7 vol) were added to the reaction mixture consecutively. The resulting mixture was heated to reflux (~82° C.). After checking completion of the reaction by HPLC analysis (NMT 3.0% (AUC) of 2,4-dichloropyrimidine, ca. 5-6 h), the solution was concentrated to 4 vol. Water (4 vol) and IPAC (4 vol) were added and the mixture was stirred and acidified to pH=1.2-1.4 using 6N HCl aqueous solution. After stirring no less than 20 min, the layers were separated. IPAC (6 vol) was added to the aqueous layer and the pH of the mixture was adjusted to 3.0-3.5 with 50% aqueous NaOH. After stifling no less than 20 min., the layers were separated. The aqueous layer was extracted with IPAC (3 vol). The combined IPAC layers were dried ($Na_2SO_4$) and filtered. IPA (1 vol) was added to the filtrate. 5-6N HCl/IPA (0.85 eq.) was added dropwise. The mixture was seeded with (R)-2-(2-chloropyrimidin-4-ylamino)-2-methylbutanoic acid hydrochloride (0.01 wt. eq.) to crystallize the product with vigorous stifling. After stirring no less than 4 h, the product was collected by filtration, washed (4:1 IPAC/IPA, 2×1.2 vol), and dried in a vacuum oven at 50° C. with a $N_2$ bleed to constant weight to afford (R)-2-(2-chloropyrimidin-4-ylamino)-2-methylbutanoic acid hydrochloride (2a) as an off-white solid.

EXAMPLE 6

Preparation of (R)-2-(2-(1H-pyrrolo[2,3-b]pyridin-3-yl)pyrimidin-4-ylamino)-2-methylbutanoic acid (4a)

(R)-2-(2-chloropyrimidin-4-ylamino)-2-methylbutanoic acid (2a) (10.00 g, 37.58 mmol) and 3-(4,4,5,5-tetramethyl-1,3,2-dioxaborolan-2-yl)-1-tosyl-1H-pyrrolo[2,3-b]pyridine (1a) (17.21 g, 43.22 mmol) were charged into a 250 mL reactor and purged with nitrogen gas. Under nitrogen gas degassing and stifling, 52.00 mL of IPA was charged into the reactor followed by 6M NaOH (20.05 mL). After degassing the stirring mixture for 15 min, 4-ditert-butylphosphanyl-N,N-dimethyl-aniline palladium(II)dichloride (37.25 mg, 0.05261 mmol) was charged into the reactor as a slurry with 2.00 mL of IPA. The resulting mixture was further degassed for another 20 min. Under positive nitrogen pressure, the reaction mixture was heated to 74° C. until the HPLC samples confirmed that the reaction was complete. Once the reaction was complete, 6M NaOH (6.263 mL) was charged into the reactor as a solution in water (74.00 mL) and the reaction was maintained at 74° C. until HPLC showed complete de-tosylation of the product.

The reaction mixture was cooled to 25° C. and adjusted to have a pH of 0.4-0.6 using 11M HCl (3.146 mL). Activated charcoal (0.3 g, 30 wt %) was charged into the reactor, and the resulting mixture was stirred for >12 Hr. The reaction mixture was filtered to remove the charcoal, and water (50 mL) was added to the filtrate after returning it to the cleaned reactor. The pH of the reaction mixture was adjusted to 5.5-6.0 using 6M NaOH (6.263 mL). The reaction mixture was heated to 64° C. under stifling. The reaction mixture was maintained under stirring at 64° C. for a period of 60 min. after the formation of a solution. The reactor was cooled at a rate of 20° C./hr until reaching a temperature of 25° C. The reaction mixture was continuously stirred at 25° C. for at least 4 hr. The batch was then filtered and washed with water (10 mL) followed by heptane (20 mL). The solids were collected at dried under vacuum at 60° C.

EXAMPLE 7

Preparation of Deuterated (R)-2-(2-(1H-pyrrolo[2,3-b]pyridin-3-yl)pyrimidin-4-ylamino)-2-methyl-N-(2,2,2-trifluoroethyl)butanamide (Ia-D)

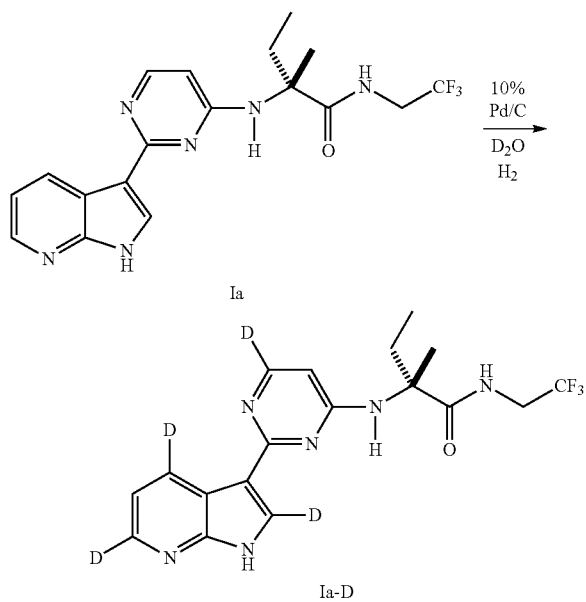

To a mixture of (R)-2-(2-(1H-pyrrolo[2,3-b]pyridin-3-yl)pyrimidin-4-ylamino)-2-methyl-N-(2,2,2-trifluoroethyl)butanamide (Ia) (85 mg, 0.2166 mmol) in $D_2O$ (20 ml) was added 10% Pd/C (15 mg). The resulting mixture was hydrogenated via balloon at reflux in a 160° C. bath for 20 hours. After 20 hours, the mixture was cooled and concentrated to ⅓ volume. Another 20 ml $D_2O$ was added to the mixture and refluxed under a balloon of $H_2$. The mixture was cool filter washed with MeOH and ETOAc, and concentrated to dryness, generating an off white solid. CMS shows D incorporation but probably not in the alkyl side chains. NMR shows partial addition of $D_2$ at 5 aromatic sites.

This off white solid was taken up in $D_2O$ (20 ml) was added fresh 10% Pd/C (15 mg) and placed on a hydrogenation apparatus. The reaction was evacuated and pressurized with $H_2$ up to 40 psi 3× times over 10 min. The pressure was released and the flask was swept with $H_2$ as the flask was reclosed. This sealed flask was then put in a 160° C. bath behind a blast shield and heated at 160° C. for 16 hours.

The reaction mixture was cooled and diluted with ETOAC, washed with water, brine dry over sodium sulfate filter and concentrated. The product was purified by flash chromatography with the following mobile phase: 0 MDC to 10% MeOH/MDC.

$^1$H-NMR showed that most $^1$H atoms on the aromatic rings were replaced with deuterium atoms.

EXAMPLE 8

Preparation of [$^{13}C,^{15}N$]-enriched (R)-2-(2-(1H-pyrrolo[2,3-b]pyridin-3-yl)pyrimidin-4-yl)amino)-2-methyl-N-(2,2,2-trifluoroethyl)butanamide (Ia*)

205 mg (1.73 mmol) of [$^{13}C,^{15}N$]-enriched uracil was mixed with 5 ml $POCl_3$ and 2 drops of $PhNEt_2$ and heated to 100° C. for about 12 hrs. The solvent was evaporated, ethyl acetate was added, and the resulting mixture was stirred for 2 hrs, transferred, and the solvent was evaporated to generate [$^{13}C,^{15}N$]-enriched 2,4-dichloropyrimidine (11a*) (260 mg of white solid).

The [$^{13}C,^{15}N$]-enriched 2,4-dichloropyrimidine (260 mg) was mixed with 2-amino-2-methyl-N-(2,2,2-trifluoroethyl)propanamide (267 mg, 0.8 eq) and DIEA (1.47 mL) in 2 mL of isopropyl alcohol. The mixture was heated to 100° C. for about 11 hours, the solvent was evaporated and ethyl acetate was added to the reaction mixture. The reaction mixture was further washed with 1N HCl and brine and dried on $Na_2SO_4$ to generate 58 mg of [$^{13}C,^{15}N$]-enriched (R)-2-((2-chloropyrimidin-4-yl)amino)-2-methyl-N-(2,2,2-trifluoroethyl)butanamide (iiic). $ES^+$=317.1, $ES^-$=315.2.

[$^{13}C,^{15}N$]-enriched (R)-2-((2-chloropyrimidin-4-yl)amino)-2-methyl-N-(2,2,2-trifluoroethyl)butanamide (iiic) (58 mg) is mixed with 3-(4,4,5,5-tetramethyl-1,3,2-dioxaborolan-2-yl)-1-tosyl-1H-pyrrolo[2,3-b]pyridine (1a) (80 mg), 2N $Na_2CO_3$ (275 µL), DME (2 mL), and $Pd(PPh_3)_4$ (10 mg). The reaction mixture is stirred at 90° C. for about 12 hr. The solvent was evaporated and ethyl acetate was added to the reaction mixture. The reaction mixture was then filtered over $SiO_2$ and eluted with ethyl acetate to generate 126 mg of crude [$^{13}C,^{15}N$]-enriched (R)-2-methyl-2-((2-(1-tosyl-1H-pyrrolo[2,3-b]pyridin-3-yl)pyrimidin-4-yl)amino)-N-(2,2,2-trifluoroethyl)butanamide (iiid). $ES^+$=553.2, $ES^-$=551.5.

120 mg of [$^{13}C,^{15}N$]-enriched (R)-2-methyl-2-(2-(1-tosyl-1H-pyrrolo[2,3-b]pyridin-3-yl)pyrimidin-4-yl)amino)-N-(2,2,2-trifluoroethyl)butanamide (iiid) was treated with LiOH (800 µL, 1N) in 2 mL of THF. The reaction mixture was heated to 80° C. for about 10 hrs, and the solvent was evaporated. The reaction mixture was extracted with ethyl acetate, filtered over $SiO_2$, and eluted with ethyl acetate to generate 19.3 mg of [$^{13}C,^{15}N$]-enriched (R)-2-((2-(1H-pyrrolo[2,3-b]pyridin-3-yl)pyrimidin-4-yl)amino)-2-methyl-N-(2,2,2-trifluoroethyl)butanamide (Ia*). $ES^+$=399.1, $ES^-$=397.6.

EXAMPLE 9

Preparation of [$^{14}C$]-enriched (R)-2-(2-(1H-pyrrolo[2,3-b]pyridin-3-yl)pyrimidin-4-yl)amino)-2-methyl-N-(2,2,2-trifluoroethyl)butanamide (Ia**)

Propiolic acid (0.393 g, 5.63 mmol) was added dropwise to a suspension of [$^{14}C$]-enriched urea (200 mCi, 55 mCi/mmol, 218.57 mg, 3.52 mmol) in polyphosphoric acid (4.3 g) and this suspension was heated at 85° C. for 8 hours. It was diluted with water (11 mL) at 0° C. then neutralized with $NH_4OH$ (aq, 28-30%) in an ice-water bath. The residue was dissolved and suspended with $NH_4OH$ (aq, 28-30%, 43 mL) and methanol (43 mL). The resulting solids were removed by filtration, and the filtrate was evaporated. A silica gel column chromatography (MeOH(10): DCM(90) to MeOH(20): DCM(80)) provided a crude compound (85% radiochemical purity, 142.2 mCi. 142.2×0.85=120.9 mCi).

To a solution of triethylamine (10 g, 98.8 mmol) in ethyl acetate (100 mL) was added 1N HCl etherate (119 mL, 119 mmol) at 0° C. The resulting suspension was stirred for 3 hours at 0° C. to water bath temperature under argon. The white suspension was filtered and the obtained solid was washed with ethyl acetate (80 mL). The solid was dried under vacuum overnight.

A mixture of [$^{14}C$]-enriched uracil (crude 142 mCi, 2.73 mmol) and $Et_3NHCl$ (75 mg, 0.546 mmol) in $POCl_3$ (0.75 mL, 8.19 mmol) was heated slowly at 130-140° C. in an oil bath for 2 hours. The resulting reaction mixture was cooled to 50-60° C. then added PCl$_5$ (1.14 g, 5.46 mmol) and POCl$_3$ (0.6 mL, 6.56 mmol) then stirred additional 1 hour at 50-60° C. The POCl$_3$ was removed by rotavap at 45° C. Silica gel column chromatography (ethyl acetate:hexanes (1:9) to ethyl acetate hexanes (3:7)) provided 0.261 g (90 mCi) of [$^{14}$C]-2, 4-DCP with 99.9% radiochemical purity by instant imager.

To a solution of K$_2$CO$_3$ (526.2 mg, 3.80 mmol) in water (1.6 mL, 6 volume) was added isovaline-HCl (292.4 mg, 1.90 mmol). The resulting solution was stirred for 10 minutes. A solution of [$^{14}$C]-enriched 2,4-dichloropyrimidine (11a) (0.261 g, 90 mCi) in isopropanol (5.2 mL, 20 volume) was added dropwise at room temperature, and the resulting mixture was heated at 85-90° C. for 18 hours. The mixture was then concentrated to 4 volumes, then 1N NaOH (6 mL) and isopropyl acetate (6 mL) were added. The aqueous phase was separated and the organic phase was extracted with 1N NaOH (6 mL×2). The combined aqueous layer was acidified to pH=3.0-3.5 using 6N HCl (aq). The resulting solution was extracted with isopropyl acetate (15 mL×3). The collected organic layer was concentrated to 3-4 volumes, then 1N HCl etherate (1.73 mL, 1.73 mmol) was added drop wise at 0° C. and stirred for 15 minutes. The organic solvent was decanted and the solid was washed with isopropyl acetate (5 mL×2). The solid was dried under vacuum and obtained 360 mg of (R)-2-(2-chloropyrimidin-4-ylamino)-2-methylbutanoic acid (2a) with 70% radiochemical purity by instant imager to provide (R)-2-(2-chloropyrimidin-4-ylamino)-2-methylbutanoic acid (2a**).

To a solution of K$_2$CO$_3$ (0.557 g, 4.02 mmol) and (R)-2-(2-chloropyrimidin-4-ylamino)-2-methylbutanoic acid (2a) in water (2.19 mL) was added acetone (4.38 mL), and the resulting mixture was stirred for 5 minutes. The (0.641 g, 1.61 mmol), PPh$_3$ (31.6 mg, 0.12 mmol) were added then acetone (4.38 mL) was added again. The reaction vessel was purged with nitrogen then Pd(OAc)$_2$ (9.8 mg, 0.04 mmol) was added, all at once. The vessel was charged with nitrogen and the lid was closed tightly with sealed reactor. The resulting reaction mixture was stirred at 75-80° C. oil bath for overnight. A half amount of solvent was removed by nitrogen streaming at oil bath then added 2N NaOH (5.5 mL). The lid was closed tightly and the mixture was stirred for 3 hours at 80° C. The solvent was removed then added 1N NaOH (3 mL) to dissolve the solids in the reaction mixture. 6N HCl was added until a pH of 4.5-5.0 was obtained. The resulting reaction mixture was filtered on Sep-pak® vac 20 cc (5 g)-C18 cartridge and washed with acetonitrile (50):water (50). After purification, 0.884 g (58.8 mCi) of [$^{14}$C]-enriched (R)-2-methyl-2-(2-(1-tosyl-1H-pyrrolo[2,3-b]pyridin-3-yl)pyrimidin-4-ylamino)butanoic acid (3a) was obtained with 85% radiochemical purity as measured by instant imager.

To a solution of [$^{14}$C]-enriched (R)-2-methyl-2-(2-(1-tosyl-1H-pyrrolo[2,3-b]pyridin-3-yl)pyrimidin-4-ylamino)butanoic acid (3a) (784 mg, 1.0 mmol, 52.13 mCi) in dichloromethane (16 mL) was added N,N-diisopropylethylamine (0.697 mL, 4.0 mmol). The resulting solution was cooled to 0° C., then T3P (50% wt in ethyl acetate, 0.656 mL, 1.1 mmol) was added. After 5 minutes, trifluoroethylamine (0.381 mL, 5.0 mmol) was added drop wise. The resulting mixture was stirred overnight at water bath temperature. Water (7 mL), 6N NaOH (8 mL) were added and the reaction was stirred for 5 minutes. The organic layer was separated and the aqueous layer was extracted with dichloromethane (30 mL×3), dried over Na$_2$SO$_4$, concentrated, and purified by silica gel column chromatography (MeOH (50) DCM (50) to MeOH (10): DCM(90)). It was dissolved in methanol (3 mL) and added PL-BnSH MP-Resin (44 mg). The resulting mixture was agitated for 24 hours at room temperature. It was filtered and rinsed the solid with methanol (1 ml) and evaporated the solvent until dry. The white solid (around 140 mg) was dissolved in 1N HCl (3 mL) and adjusted the pH 7.5-8.0 using 6N NaOH at room temperature. The resulting suspension was stirred for 2 hours at 5° C. and obtained the white solid was rinsed with water (0.4 mL×3). Drying under vacuum provided 140 mg (19.5 mCi) of [$^{14}$C]-enriched (R)-2-(2-(1H-pyrrolo[2,3-b]pyridin-3-yl)pyrimidin-4-ylamino)-2-methyl-N-(2,2,2-trifluoroethyl)butanamide (Ia).

EXAMPLE 10a

Preparation of Methyl 2-amino-2-methylbutanoate 2-amino-2-methylbutanoic acid HCl salt (20 g, 130.2 mmol) was suspended in 150 mL methanol. A solution of HCL (4M in dioxane was added and the mixture heated to 50° C. overnight. The mixture was cooled to room temperature and evaporated to dryness under vacuum. The resulting isovaline methyl ester (20 g) was used without further purification. $^1$H NMR (300 MHz, DMSO) δ 3.78-3.64 (m, 1H), 3.61 (s, 3H), 3.54-3.41 (m, 1H), 2.50 (d, J=1.6 Hz, 1H), 1.76 (s, 2H), 1.66-1.35 (m, 2H), 1.17 (s, 3H), 0.77 (t, J=7.5 Hz, 3H).

EXAMPLE 10b

Preparation of Methyl 2-((2-chloropyrimidin-4-yl)amino)-2-methylbutanoate

A 250 mL flask was charged with methyl 2-amino-2-methylbutanoate (8.4 g, 54.4 mmol), 2,4-dichloropyrimidine (8.9 g, 59.8 mmol), TEA (5.5 g, 54.4 mmol) and 80 mL NMP. The reaction mixture was heated to 80° C. for ~18 hours. After cooling, water (300 mL) was added and the mixture extracted with MTBE. The organic extracts were washed with water and dried over sodium sulfate. Filtration and evaporation under vacuum afforded 13 g of an orange oil which was purified by flash chromatography, (0-100% ethyl acetate-hexane affording 4.6 g (34%) methyl 2-((2-chloropyrimidin-4-yl)amino)-2-methylbutanoate as an oil. $^1$H NMR: (CDCl$_3$) δ 8.05-7.88 (m, 1H), 6.28 (δ, 1H), 5.95 (δ, 1H), 4.2-4.0 (μ, 1H), 3.86 (m, 1H), 2.46 (m, 1H), 2.10 (m, 1H), 2.01 (m, 1H), 1.72 (m, 3H), 0.89 (m, 3H). m/e, m+1 244.1

EXAMPLE 10c

Preparation of Methyl 2-methyl-2-((2-(1-tosyl-1H-pyrrolo[2,3-b]pyridin-3-yl)pyrimidin-4-yl)amino)butanoate A 500 mL pressure vessel was charged with 80 mL DME, 1-(p-tolylsulfonyl)-3-(4,4,5,5-tetramethyl-1,3,2-dioxaborolan-2-yl)pyrrolo[2,3-b]pyridine (4.4 g, 11.05 mmol), methyl 2-((2-chloropyrimidin-4-yl)amino)-2-methylbutanoate, (2.44 g, 10.05 mmol), sodium carbonate (10 mL of 2M aq solution, 20 mmol) and degassed the mixture with a nitrogen stream for 30 min. Then, Pd(dppf)Cl$_2$ was added, the flask sealed and heated to 90° C. for 15 hours. The mixture was cooled and filtered through Florisil. Evaporation under vacuum gave 7.8 g of a brown residue which was purified by flash chromatography, (0-80% ethyl acetate-hexane affording 3.9 g (81%) methyl 2-methyl-2-((2-(1-tosyl-1H-pyrrolo[2,3-b]pyridin-3-yl)pyrimidin-4-yl)amino)butanoate. $^1$H NMR (CDCl$_3$) 8.83 (dd, 1H), 8.52 (s, 1H), 8.44 (dd, 1H), 7.28 (dd, 4H), 6.27 (d, 1H), 5.29 (s, 1H), 3.74 (d, 3H), 2.38 (s, 3H), 2.34-2.15 (m, 1H), 2.18-2.00 (m, 2H), 1.98 (s, 2H), 1.74 (s, 3H), 1.34-1.17 (m, 15H), 1.03 (m, 3H). m/e m+1 480.25

EXAMPLE 10d

Preparation of 2-((2-(1H-pyrrolo[2,3-b]pyridin-3-yl)pyrimidin-4-yl)amino)-2-methylbutanoic acid Lithium hydroxide hydrate (1.9 g, 45 mmol) was added to 50 mL THF and 15 mL water. Then 2-methyl-2-((2-(1-tosyl-1H-pyrrolo[2,3-b]pyridin-3-yl)pyrimidin-4-yl)amino)butanoate was added and the mixture was heated to reflux for 18 hours. The reaction was cooled to rt and 50 mL 1M citric acid solution was added. The mixture was extracted with 3×100 mL ethyl acetate where upon a white precipitate formed in the aqueous layer. The product was then filtered from the aqueous layer and dried under vacuum affording 1.6 g (68%) 2-((2-(1H-pyrrolo[2,3-b]pyridin-3-yl)pyrimidin-4-yl)amino)-2-methylbutanoic acid as white solid. $^1$H NMR (300 MHz, MeOD) 8.87 (dd, 1H), 8.32 (m, 2H), 7.94 (d, 1H), 3.31 (m, 3H), 2.80 (q, 1H), 2.29-1.95 (m, 2H), 1.68 (s, 3H), 0.96 (t, 3H). m/e m+1=312.22.

EXAMPLE 10e

Preparation of 2-(2-(1H-pyrrolo[2,3-b]pyridin-3-yl)pyrimidin-4-yl)amino)-2-methyl-N-(2,2,2-trifluoroethyl)butanamide A 100 mL flask was charged with 2-((2-(1H-pyrrolo[2,3-b]pyridin-3-yl)pyrimidin-4-yl)amino)-2-methylbutanoic acid (1.6 g, 5.14 mmol), 20 mL DMF, HOBt (243.1 mg, 1.8 mmol), EDC (1.18 g, 6.17 mmol) and 2,2,2-trifluoroethanamine (450 µL, 5.65 mmol). Stir at rt ~18 hours. 75 mL water was added and the mixture extracted with 3×100 mL MTBE. The combined organics were washed with water, brine and dried over sodium sulfate. The solution was filtered and evaporated under vacuum affording 1.1 g (54%) of a pale yellow solid which was pure racemic 2-((2-(1H-pyrrolo[2,3-b]pyridin-3-yl)pyrimidin-4-yl)amino)-2-methyl-N-(2,2,2-trifluoroethyl)butanamide.

EXAMPLE 10f

Preparation of (2s)-2-methyl-2-[[2-(1H-pyrrolo[5,4-b]pyridine-3-yl]amino]-N-(2,2,2-trifluoroethyl)butanamide The racemic mixture of 2-((2-(1H-pyrrolo[2,3-b]pyridin-3-yl)pyrimidin-4-yl)amino)-2-methyl-N-(2,2,2-trifluoroethyl)butanamide from the previous step was separated into the two component enantiomers using SFC chromatography to give as the pure enantiomer, VRT-1071001-1; (2s)-2-methyl-2-[[2-(1H-pyrrolo[5,4-b]pyridine-3-yl]amino]-N-(2,2,2-trifluoroethyl) butanamide. 186.7 mg (16.7%). $^1$H NMR (300 MHz, MeOD) δ 8.82 (dd, J=8.0, 1.3 Hz, 1H), 8.22 (dd, J=4.7, 1.3 Hz, 1H), 8.19-8.04 (m, 2H), 7.22 (dd, J=8.0, 4.8 Hz, 1H), 6.42 (d, J=5.9 Hz, 1H), 3.98-3.59 (m, 2H), 3.38-3.24 (m, 3H), 2.22 (dq, J=15.0, 7.5 Hz, 1H), 2.03-1.80 (m, 1H), 1.62 (s, 3H), 1.01-0.82 (m, 3H). m/e m+1=393.36

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A process for preparing a compound of Formula 1:

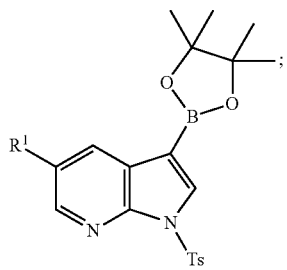

or a pharmaceutically acceptable salt thereof, wherein $R_1$ is —H, —Cl or —F; comprising the steps of:

iva) reacting a compound of Formula 5 with bromine in an organic solvent to generate a compound of Formula 6:

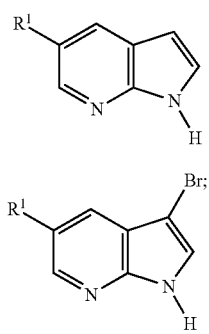

va) reacting the compound of Formula 6 with p-toluenesulfonyl chloride to generate a compound of Formula 7:

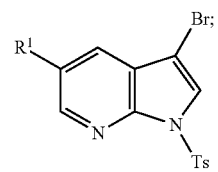

vi) reacting the compound of Formula 7 with triisopropyl borate, in the presence of an organic solvent and a strong lithium base to generate a compound of Formula 8:

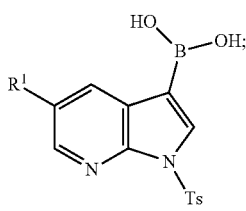

and vii) esterifying the compound of Formula 8 with pinacolate alcohol in an organic solvent to generate a compound of Formula 1.

2. The process of claim 1, wherein the organic solvent in step iva) is an aprotic solvent.

3. The process of claim 2, wherein the aprotic solvent is dimethylformamide.

4. The process of claim 1, wherein the reaction in step iva) is performed at a temperature of about −5 °C. to about 30 °C.

5. The process of claim 4, wherein the reaction of step iva) is performed at a temperature of about 0 °C. to about 10 °C.

6. The process of claim 1, wherein the reaction of step va) is performed in the presence of sodium hydride.

7. The process of claim 6, wherein the reaction of step va) is performed at a temperature of about 0 °C. to about 30 °C.

8. The process of claim 7, wherein the reaction of step va) is performed at a temperature of about 5 °C. to about 25 °C.

9. The process of claim 1, wherein the strong lithium base of step vi) is n-butyl lithium.

10. The process of claim 1, wherein the reaction of step vi) is performed at a temperature of about −100 °C. to about −70 °C.

11. The process of claim 1, wherein the organic solvent of step vii) is a halogenated hydrocarbon.

12. The process of claim 11, wherein the halogenated hydrocarbon is dichloromethane or dichloroethane.

13. The process of claim 1, wherein the esterification reaction of step vii) is performed at a temperature of about 0 °C. to about 60 °C.

14. The process of claim 13, wherein the esterification reaction of step vii) is performed at a temperature of about 10 °C. to about 40 °C.

15. A process for preparing a compound of Formula 1:

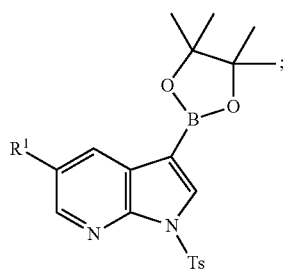

or a pharmaceutically acceptable salt thereof, wherein $R^1$ is —H, —Cl or —F; comprising the steps of:

ivb) reacting a compound of Formula 5 with p-toluenesulfonyl chloride to generate a compound of Formula 9:

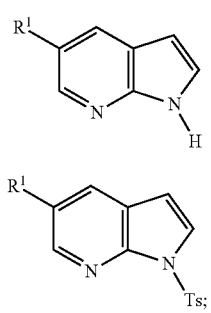

vb) reacting the compound of Formula 9 with N-bromosuccinimide to generate a compound of Formula 7

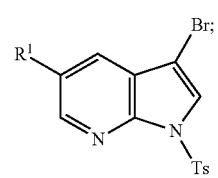

vi) reacting the compound of Formula 7 with triisopropyl borate, in the presence of an organic solvent and a strong lithium base to generate a compound of Formula 8:

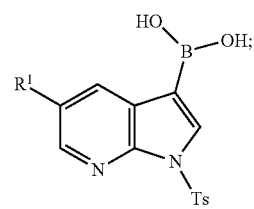

and vii) esterifying the compound of Formula 8 with pinacolate alcohol in an organic solvent to generate a compound of Formula 1.

16. The process of claim 15, wherein the reaction of step ivb) is performed in the presence of sodium hydride.

17. The process of claim 15, wherein the strong lithium base of step vi) is n-butyl lithium.

18. The process of claim 15, wherein the reaction of step vi) is performed at a temperature of about −100 °C. to about −70 °C.

19. The process of claim 15, wherein the organic solvent of step vii) is a halogenated hydrocarbon.

20. The process of claim 19, wherein the halogenated hydrocarbon is dichloromethane or dichloroethane.

21. The process of claim 15, wherein the esterification reaction in step vii) is performed at a temperature of about 0 °C. to about 60 °C.

22. The process of claim 21, wherein the esterification reaction in step vii) is performed at a temperature of about 10 °C. to about 40 °C.

* * * * *